US006045515A

United States Patent [19]
Lawton

[11] Patent Number: 6,045,515
[45] Date of Patent: Apr. 4, 2000

[54] METHODS AND APPARATUS FOR DIAGNOSING AND REMEDIATING READING DISORDERS

[76] Inventor: Teri A. Lawton, 20220-Q Paradise La., Topanga, Calif. 90290

[21] Appl. No.: 09/056,839

[22] Filed: Apr. 7, 1998

Related U.S. Application Data

[60] Provisional application No. 60/041,916, Apr. 7, 1997.

[51] Int. Cl.[7] .................................................. A61B 13/00
[52] U.S. Cl. .......................... 600/558; 351/223; 351/239
[58] Field of Search ........................... 600/558; 351/211, 351/223, 239, 243

[56] References Cited

U.S. PATENT DOCUMENTS

| | | | |
|---|---|---|---|
| 3,842,822 | 10/1974 | Levinson et al. | 600/558 |
| 4,493,539 | 1/1985 | Cannon, Jr. | 600/558 |
| 4,526,452 | 7/1985 | Hirsch | 351/243 |
| 4,706,686 | 11/1987 | Levinson | 600/558 |
| 4,889,422 | 12/1989 | Pavlidis | 351/210 |
| 5,176,147 | 1/1993 | Bodis-Wollner | 600/558 |
| 5,474,081 | 12/1995 | Livingstone et al. | 600/558 |
| 5,539,482 | 7/1996 | James et al. | 600/558 |
| 5,589,897 | 12/1996 | Sinclair et al. | 351/223 |
| 5,694,199 | 12/1997 | Rodriguez | 351/223 |

OTHER PUBLICATIONS

Aboitiz, F., Scheibel, A.B., Fisher, R.S., Zaidel, E., Fiber Composition of the Human Corpus Callosum, *Brain Research*, vol. 598, 1992: pp 143–153.

Allman, J., Miezin, F., McGuinness, E., Stimulus Specific Responses from Beyond the Classical Receptive Field: Neurophysiological Mechanisms for Local–Global Comparisons in Visual Neurons, *Ann. Rev. Neurosci.* vol. 8, pp 407–430.; 1985.

Atkinson, J., Braddick, O.J., The Developmental Course of Cortical Processing Streams in the Human Infant: pp 247–253.

Atkinson, J., Review of Human Visual Development: Crowding and Dyslexia, *Vision and Visual Dyslexia*, pp 44–57.

Barlow, H.B., and Levick W.R., The Mechanism of Directionally Selective Units in Rabbit's Retina, *J. Physiol*, vol. 178, 1965: pp 477–504.

Boder, E., Developmental Dyslexia: a Diagnostic Approach Based on Three Atypical Reading–spelling Patterns, *Develop. Med. Child. Neurol.*, vol. 15, 1973: 663–687.

Borsting, E., Ridder, W.H., Dudeck, K., Kelley, C., Matsui, L., Motoyama, J., The Presence of a Magnocellular Defect Depends on the Type of Dyslexia, *Vision Res.*, vol. 36, No. 7, 1996: pp 1047–1053.

(List continued on next page.)

*Primary Examiner*—Cary O'Connor
*Assistant Examiner*—Charles Marmor, II
*Attorney, Agent, or Firm*—Oppenheimer Wolff & Donnelly LLP

[57] ABSTRACT

Reading disorders are diagnosed and remediated in a subject by respectively measuring and improving contrast sensitivity for motion discrimination of the subject. A background is displayed on a monitor with a contrast and a spatial frequency. A test window is superimposed over the background and includes a test pattern with a contrast and a spatial frequency. The contrasts and the spatial frequencies are within respective ranges which stimulate the visual cortical movement system of the subject. The test pattern is then moved within the test window. The subject provides a signal indicative of the direction the subject believes the test pattern moved. In response to this signal, the contrast of the test pattern, the spatial frequency of the background, or the spatial frequency of the test pattern is modified, either by increasing or decreasing its respective value. This process is then repeated a number of times, cycling through predetermined combinations of test patterns and backgrounds. Contrast sensitivity may be measured to determine whether a child is dyslexic. Repeated stimulation by the methods and apparatus of the invention improves contrast sensitivity, thereby remediating dyslexia and improving reading ability.

86 Claims, 37 Drawing Sheets

OTHER PUBLICATIONS

Breitmeyer, B.G., Unmasking Visual Masking: A Look at the "Why" Behind the Veil of the "How," *Psychological Review,* vol. 87, No. 1, 1980: pp 52–69.

Burr, D., Morrone, C., Maffei, L., Intra–cortical Inhibition Prevents Simple Cells from Responding to Textured Visual Patterns, *Exp. Brain Res.,* vol. 43, 1981: pp 455–458.

Burr, D.C., Morrone, M.C., Inhibitory Interactions in the Human Vision System Revealed in Pattern–evoked Potentials, *J. Physiol.,* vol. 389, 1987: pp 1–21.

Burr, D.C., Morrone, M.C., Ross, J., Selective Suppression of the Magnocellular Visual Pathway During Saccadic Eye Movements, *Nature,* vol. 371, 1994: pp 511–513.

Burr, D.C., Sensitivity to Spatial Phase, *Vision Research,* vol. 20, 1980: pp 391–396.

Castleman, K.C., *Digital Image Processing,* Prentice–Hall, Inc, Simon & Schuster Company, Upper Saddle River, NJ, 1996, pp 1–650.

Cavanagh, P., Tyler, C.W., Favreau, O.E., Perceived Velocity of Moving Chromatic Gratings, *J. Opt, Soc. Am. A.,* vol. 1, No. 8, 1984: pp 893–899.

Christenson, G.N., Griffin, J.R., Deland, P.N., Validity of the Dyslexia Screener, *Optometry and Vision Science,* 1991: pp 275–281.

Cornelissen, P., Richardson, A., Mason, A., Fowler, S., Contrast Sensitivity and Coherent Motion Detection Measured at Photopic Luminance Levels in Dyslexics and Controls, *Vision Res.* vol. 35, No. 10, 1995: pp 1483–1494.

DeValois, K.K., Tootell, R.B.H., Spatial–frequency–specific Inhibition in Cat Striate Cortex Cells, *J. Physiol,* vol. 333, 1983: pp 359–376.

DeYoe, E.A., VanEssen, D.C., Concurrent processing streams in monkey visual cortex, *TINS,* vol. 11, No. 5, 1988: pp 219–226.

Dow, B.M., Functional Classes of Cells and Their Laminar Distribution in Monkey Visual Cortex, *National Eye Institute,* 1973: pp 927–946.

Eden, G.F., VanMeter, J.W., Rumsey, J.M., Maisog, J.M., Woods, R.P., Zeffiro, T.A., Abnormal Processing of Visual Motion in Dyslexia Revealed by Functional Brain Imaging, *Nature,* vol. 382, 1996: pp 66–69.

Farmer, M.E., Klein, R.M., The Evidence For A Temporal Processing Deficit Linked To Dyslexia: A Review, *Psychonomic Bulletin & Review,* 1995: pp 460–493.

Fischer, B., Webber, H., Saccadic Reaction Times Of Dyslexic And Age–Matched Normal Subjects, *Perception,* vol. 19, 1990: pp 805–818.

Galaburda, A., Livingstone, M., Evidence for a Magnocellular Defect in Developmental Dyslexia, *Annals NY Acad of Science:* pp 70–82.

Geiger, G., Lettvin, J.Y., Dyslexia and Reading as Examples of Alternative Visual Strategies, *Brain and Reading:* pp 331–343.

Geiger, G., Lettvin, J.Y., Fahle, M., Dyslexic Children Learn a New Visual Strategy for Reading: a Controlled Experiment, *Vision Res.,* vol. 34, No. 9, 1994: pp 1223–1233.

Gilbert, C.D., Das, A., Ito, M., Kapadia, M., Westheimer, G., Spatial Integration and Cortical Dynamics, *Proc. Natl. Acad. Sci. USA,* vol. 93, 1996: pp 615–622.

Guerin, D.W., Griffin, J.R., Gottfried, A.W., Christenson, G.N., Concurrent Validity and Screening Efficiency of the Dyslexia Screener, *Psy Assessment,* vol. 5, No. 3, 1993: pp 369–373.

Hari, R., Kiesila, P., Deficit of Temporal Auditory Processing in Dyslexic Adults, *Neuroscience Letters,* vol. 205, 1996: pp 138–140.

Higgins, K.E., Jaffe, M.J., Coletta, N.J., Caruso, R.C., deMonasterio, F.M., Spatial Contrast Sensitivity, *Arch Ophthalmol,* vol. 102, 1984: pp 1035–1041.

Hogben, J.H., Rodino, I.S., Clark, C.D., Pratt, C., A Comparison of Temporal Integration in Children with a Specific Reading Disability and Normal Readers, *Vision Res.,* vol. 35, No. 14, 1995: pp 2067–2074.

Innocenti, G. M., General Organization of Callosal Connections in the Cerebral Cortex,: pp 291–353.

Lawton, T., Developing Magnocellular Pathways in Children Show Reduced Sensitivity to Movement Discrimination, V. Lakshminarayanan (ed.), *Basic and Clinical Applications of Vision Science,* 1997: pp 159–164.

Lawton, T.A., Sebag, J., Sadun, A.A., Castleman, K.R., Image Enhancement Improves Reading Performance in Age–related Macular Degeneration Patients, *Vision res.,* vol. 38, No. 1, 1998: pp 153–162.

Lawton, T.B., Improved Reading Performance Using Individualized Compensation Filters for Observers with Losses in Central Vision, *Ophthalmology,* vol. 96, No. 1, 1989: pp 115–126.

Lawton, T.B., Image Enhancement Filters Significantly Improve Reading Performance for Low Vision Observers, *Ophthal. Physiol. Opt.,* vol. 12, 1992: pp 193–200.

Lawton, T.B., Improved Word Recogition for Observers with Age–related Maculopathies Using Compensation Filters, *Clin. Vision. Sci.* vol. 3, No. 2, 1988: pp 125–135.

Lawton, T.B., Outputs of Paired Gabor Filers Summed Across the Background Frame of Reference Predict the DirectIon of Movement, *IEEE,* vol. 36, No. 1, 1989: pp 130–139.

Lawton, T.B., Spatial–frequency Spectrum of Patterns Changes the Visibility of Spatial–phase Differences, *Opt. Soc. Am. A,* vol. 2, No. 7, 1985: pp 1140–1152.

Lawton, T.B., The Effect of Phase Structures on Spatial Phase Discrimination, *Vision Res.* vol. 24, No. 2, 1984: pp. 139–148.

Livingstone, M., Hubel, D., Segregation of Form, Color, Movement, and Depth: Anatomy, Physiology, and Perception, *Science,* vol. 240, 1988: pp 740–749.

Livingstone, M.S., Rosen, G.D., Drislane, F.W., Galaburda, A.M., Physiological and Anatomical Evidence for a Magnocellular Defect in Developmental Dyslexia, *Proc. Natl. Acad. Sci, USA,* vol. 88, 1991: pp 7943–7947.

Lovegrove, W.J., Bowling, A., Badcock, D., Blackwood M., Specific Reading Disability: Differences in Contrast Sensitivity as a Function of Spatial Frequency, *Science,* vol. 210, 1980: pp 439–440.

Lund, J.S., Lund, R.V., Hendrickson, A.E., Bunt, A.H., Fuchs, A.F, The origin of Efferent Pathways from the Primary Visual Cortex, Area 17, of the Macaque Monkey as Shown by Retrograde Transport of Horseradish Peroxidase, *Comp. Neur,* vol. 164: pp 287–304.

Merigan W.H. Maunsell, J.H.R., Macaque Vision After Magnocellular Lateral Geniculate Lesions, *Dept of Ophthalmology and Physionlogy and Center for Visual Science,* Univ of Rochester, 1990: pp 347–352.

Merzenich, M.M., Jenkins, W.M., Johnston, P., Schreiner, C., Miller, S.L., Tallal, P., Temporal Processing Deficits of Language–Learning Imparied Children Ameliorated by Training, *Science,* vol. 271, 1996: pp 77–80.

Ohzawa, I., DeAngelis, G.C., Freeman, R.D., Stereoscopic Depth Discrimination in the Visual Cortex: Neurons Ideally Suited as Disparity Detectors, *Reports,* 1990: pp 1037–1041.

Pandya, D.N., Seltzer, B., The Topography of Commissural Fibers, *Functions of the Corpus Callosum,* 1986: pp 47–73.

Pasternak, T., Merigan, W.H., Motion Perception Following Lesions of the Superior Temporal Sulcus in the Monkey, *Cerebral Cortex,* 1994: pp 247–259.

Pavlidis, G.T., Do Eye Movements Hold the Key to Dyslexia? *Neurophychologia,* vol. 199, 1981: pp 57–64.

Ramachandran, V.S., Gregory, R.L., Does Colour Provide An Input To Human Motion Perception? *Nature,* vol. 275, 1978: pp 85–86.

Rosen, G.D., Sherman, G.F., Galaburda, A.M., Interhemispheric Connections Differ Between Symmetrical and Asymmetrical Brain Regions, *Neurosceince,* vol. 33, 1989: pp 525–533.

Schiller, P., Logothetis, N.K., Charles, E.R., Role of the Color–opponent and Broad–band Channels in Vision, Cambridge University Press, 1991, pp 321–346.

Shapley, RO., Kaplan, E., Soodak, R., Spatial Summation And Contrast Sensitivity of X and Y Cells in The Lateral Geniculate Nucleus of the Macaque, *Nature,* vol. 292, 1981.

Shatz, C.J., Emergence of Order in Visual System Development, *Proc. Natl. Acad. Sci. USA,* vol. 93, 1996: pp 602–608.

Solomon, J.A., Pelli, D.G., The Visual Filter Mediating Letter Identification, *Nature,* vol. 369, 1994: pp 395–397.

Stanley, G., Hall, R., A Comparison of Dyslexics and Normals in Recalling Letter Arrays After Brief Presentation, *Dept of Psy,* Univ of Melbourne, Australia, 1973: pp 301–304.

Stein, J., Riddell, P., Fowler, S., Disordered Right Hemisphere Function in Developmental Dyslexia, *Brain and Reading,* 1989: pp 139–157.

Stein, J.F., Visuospatial Sense, Hemispheric Asymmetry and Dyslexia, *Vision and Visual Dyslexia,* 1991: pp 181–188.

Tollhurst, D.J., Barfield, L.P., Interactions Between Spatial Frequency Channels, *Vision Research,* vol. 18, 1978: pp 951–958.

Ungerleider, L.G., Mishkin, M., Two Cortical Visual Systems, *Cerebral Cortex,* pp 549–586.

VanEssen, D.C., Maunsell, J.H.R., Hierarchical Organization And Functional Streams In The Visual Cortex, *TINS,* 1993: pp 370–375.

VanSluyters, R.C., Atkinson, J., Banks, M.S., Held, R.M., Hoffmann, K.P., Shatz, C.J., The Development of Vision and Visual Perception, *Visual Perception, The Neurophysiological Foundations,* 1990: pp 349–379.

Wattam–Bell, J., The Development of Maximum Displacement Limits for Discrimination of Motion Direction in Infancy, *Vision Res.,* vol. 32, No. 4, 1992: pp 621–630.

Westheimer, G., Eye Movement Responses to a Horizontally Moving Visual Stimulus, *AMA Archives of Ophthalmology,* pp 932–941.

Wetherill, G.B., Levitt, H., Sequential Estimation of Points on a Psychometric Function, *Brit. J. Mathematical and Statistical Psy,* vol. 18, 1965: pp 1–10.

Zeki, S., Shipp, S., The Functional Logic of Cortical Connections, *Nature,* vol. 334, 1988: pp 311–317.

Zeki, S.M., Functional Organization of a Visual Area in the Posterior Bank of the Superior Temporal Sulcus of the Rehesus Monkey, *J. Physiol.,* vol. 236, 1974: pp 549–573.

METHODS AND APPARATUS FOR DIAGNOSING AND REMEDIATING READING DISORDERS

CROSS-REFERENCE TO RELATED APPLICATIONS

The present application claims the benefit under 35 U.S.C. § 119(e) of U.S. Provisional Application Ser. No. 60/041,916 filed Apr. 7, 1997.

BACKGROUND OF THE INVENTION

1. Field of the Invention

The present invention relates to methodology for diagnosing and treating reading disorders such as dyslexia. More particularly, the present invention relates to methods and apparatus for measuring contrast sensitivity for motion discrimination. The present invention also relates to methods and apparatus for improving contrast sensitivity for motion discrimination. The inventor of the present invention has determined that by improving contrast sensitivity for motion discrimination by practicing the present invention, children who are dyslexic, as well as children with normal reading ability, may improve their reading ability.

2. Description of the Related Art

When a pattern of light falls on the retina, the image is processed within the retina to some extent Ganglion cells of the retina send signals out of the eye to a relay nucleus in the thalamus of the brain. Cells of the thalamus in turn send signals to the visual cortex for further processing. There are two major types of retinal ganglion cells which respectively contact two divisions of cells in the relay nucleus of the thalamus: the parvocellular division and the magnocellular division. Cells in the parvocellular division have small receptive fields and are useful for visual tasks requiring a high degree of acuity. Cells in the magnocellular division, which are about ten-times less numerous than those of the parvocellular division, have large receptive fields and are useful for visual tasks requiring a high degree of movement detection. Cells of the magnocellular division have coarse acuity and high contrast sensitivity.

In view of the above, the vision system of a human may be divided into two visual streams. The first stream is a magnocellular stream which detects the movement of an object. This movement stream has a high sensitivity to low contrast (for example, below 10%), to low luminance, to movement, and has low resolution. The second stream is a parvocellular stream which detects the color, shape, and texture of patterns. This second or acuity steam has low contrast sensitivity and high resolution. The acuity stream is most sensitive to contrasts above about 10%.

The parvocellular and magnocellular cells, either alone or in combination, provide the information used by many different visual cortical pathways (or "streams") which are specialized at performing different perceptual tasks. One such specialized pathway is a visual cortical area called Medial Temporal, or "MT," which is central in the analysis of direction of motion. Most of the signals that drive neurons in area MT derive from neurons in layer 4b of the primary visual cortex, which neurons in turn are primarily supplied by input from the magnocellular cells. (In primates, the primary visual cortex is the only cortical area that receives signals from the retina via neurons in the thalamic relay nucleus.) Direction selectivity is a fundamental characteristic of the magnocellular neurons and is mediated by cells in both layer 4b in the striate cortex and in the MT cortex.

Certain aspects of magnocellular networks, such as direction discrimination and detecting brief patterns, are still developing in all 5 to 9 year old children, when compared to normal adults. Moreover, the immature magnocellular and inhibitory networks of dyslexics confirm the increasing psychophysical, physiological, and anatomical evidence that dyslexics have anomalies in their magnocellular networks, demonstrated by (1) higher contrast thresholds to detect brief patterns, (2) an impaired ability to discriminate both the direction and the velocity of moving patterns, and (3) unstable binocular control and depth localization when compared to age-matched normals. There is substantial evidence that dyslexics have a disordered posterior parietal cortex and corpus callosum, having immature inhibitory networks that severely limit a child's ability to both discriminate direction of movement and read.

Reading is the most important skill that is learned in the first and second grades. Yet there are no standardized ways to evaluate or to teach reading. A natural assumption is that reading relies on the higher resolution pattern system evaluated by measuring an observer's visual acuity and color discrimination ability. It is generally believed that movement discrimination is involved in reading solely as a means of directing eye movements, coordinating each saccade so that letter recognition can be conveyed by the portion of the vision system which has a higher resolution. It is intriguing that differences between children with reading problems (e.g., those who are dyslexic) and children with normal reading ability were revealed only by tests of the cortical movement system. On the other hand, tests of the pattern system, such as visual acuity using long duration patterns, revealed no differences between children with normal reading and children with reading problems. However, a recent study questions whether dyslexic children show a temporal processing deficit, and another study concludes that the contrast sensitivity functions (CSFs) of dyslexic children are unrelated to their reading ability.

A natural assumption in the art is that reading relies on the high-resolution acuity system. The acuity system may be evaluated by measuring the visual acuity of a subject, which is measured by an index of 20/20, 20/40, and so on as known in the art. Conventional wisdom in the art teaches that dyslexia, which may be defined as a difficulty in reading in a child of normal intelligence and an adult-level acuity (i.e., 20/20), is explained as a difficulty in decoding words on a page that are readily seen.

One approach used to remediate dyslexia involves training the child to engage in novel, small-scale hand-eye coordination tasks like drawing, painting, and modeling, coupled with word identification, for 5 hours per week over 8 months. This approach improved reading at least one grade level. The mechanism for this improvement is unknown.

BRIEF SUMMARY OF THE INVENTION

In view of the foregoing drawbacks of current techniques in the art, one of the objectives of the present invention is to provide methods and apparatus for diagnosing and remediating reading disorders by respectively measuring and improving contrast sensitivity for motion discrimination of the subject. Dyslexic children who have practiced the methods of the present invention have increased their reading rates up to 9 times on average. There is also a marked increase in reading rates in children with previously determined normal ability.

According to one aspect of the invention, a background is displayed on a monitor with a contrast and a spatial frequency. A test window is superimposed over the background and includes a test pattern with a contrast and a spatial frequency. The contrasts and the spatial frequencies are within respective ranges which stimulate the visual cortical movement system of the subject. The test pattern is then moved within the test window. The subject provides a signal indicative of the direction the subject believes the test pattern moved. In response to this signal, the contrast of the test pattern, the spatial frequency of the background, or the spatial frequency of the test pattern is modified, either by increasing or decreasing its respective value.

This process is then repeated a number of times, cycling through predetermined combinations of test patterns and backgrounds. Contrast sensitivity may be measured to determine whether a child is dyslexic. Repeated stimulation by the methods and apparatus of the invention improves contrast sensitivity, thereby remediating dyslexia and improving reading ability.

Other objects, features, and advantages of the present invention will become apparent to those skilled in the art from a consideration of the following detailed description taken in conjunction with the accompanying drawings.

BRIEF DESCRIPTION OF THE SEVERAL VIEWS OF THE DRAWINGS

FIGS. 12a–12c are graphical views of data illustrating relationships between contrast sensitivity with respect to background spatial frequency for a test-pattern spatial frequency of 1.0 cycle per degree for various subjects in Grade 2;

DETAILED DESCRIPTION OF THE INVENTION

Figure 17:
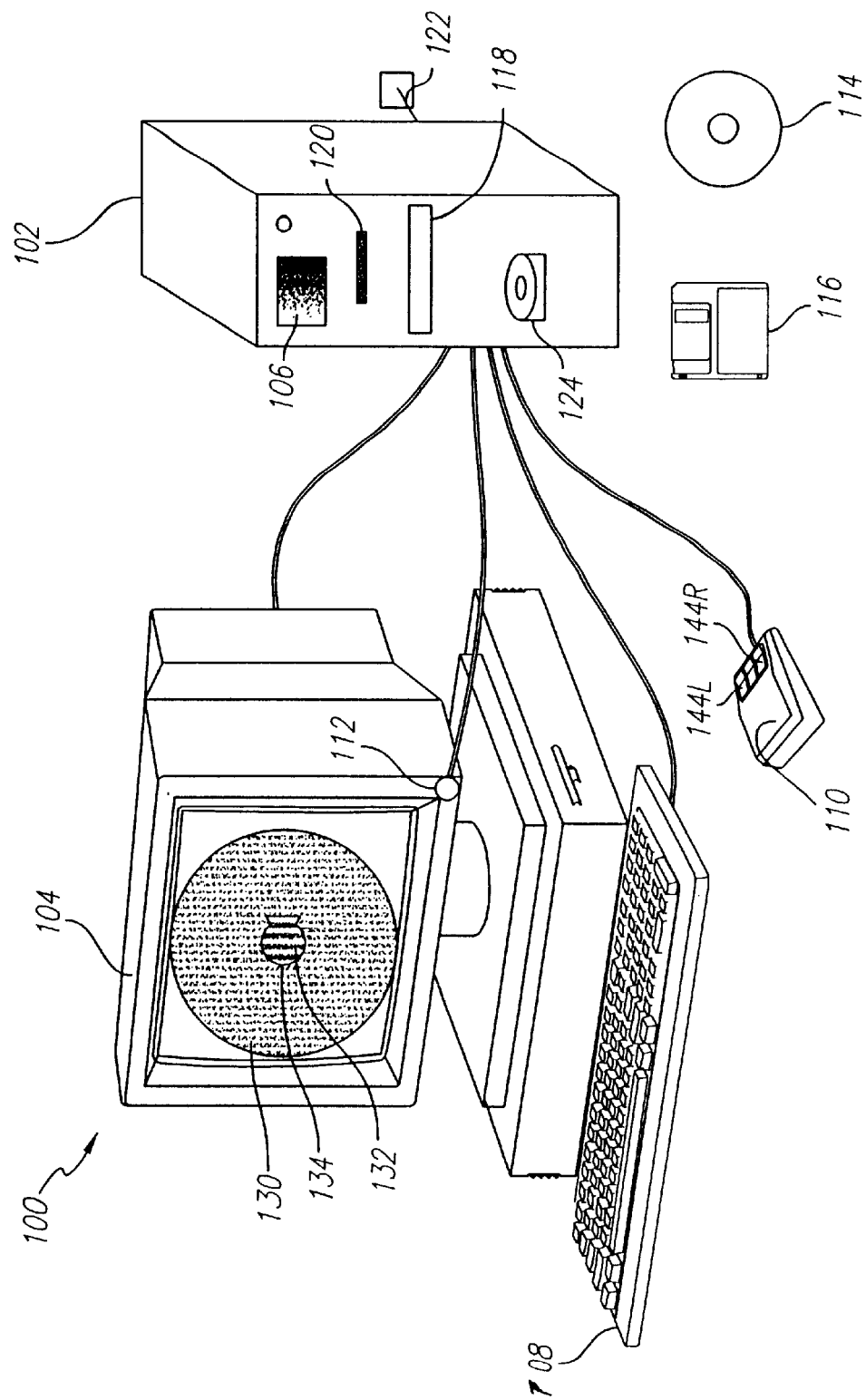
FIG. 17 is a perspective view of a computer system configured in accordance with an exemplary embodiment of the present invention for measuring and improving contrast sensitivity for motion discrimination.

Referring more particularly to the drawings, exemplary apparatus for measuring and improving the contrast sensitivity for motion discrimination of a subject and configured in accordance with the teachings of the present invention is illustrated in FIG. 17 as a computer system 100. Exemplary computer system 100 is configured to measure and also improve the contrast sensitivity for motion discrimination of a subject. Measuring contrast sensitivity for motion discrimination is used to determine whether a subject suffers from a reading disorder, such as dyslexia. Improving contrast sensitivity for motion discrimination results in an improvement in reading ability and a remediation of the reading disorder. In other words, the present invention may be used to cure dyslexia. For purposes of this description and without limiting the scope of the present invention, exemplary system 100 includes a computer 102 which is connected to output devices such as a visual output or monitor 104 and an audio output or speaker 106. Computer 102 is also connected to input devices such as a keyboard 108, a mouse 110, and/or a microphone 112.

Exemplary methodology of the invention may be implemented on the system in the form of instructions stored as computer-readable code which configures exemplary computer 102 to perform in accordance with the present invention. These instructions may be stored on computer-readable storage media such as a compact disc read-only memory (CD-ROM) 114 or a floppy disc 116 for downloading into computer 102 through a CD-ROM drive 118 or a floppy drive 120, respectively. Alternatively, the computer-readable instructions may be downloaded into computer 102 through an Internet connection 122 as known in the art. In addition, computer 102 may include a hard disc 124 on which computer-readable instructions may be pre-stored or "bundled" as known in the art. Exemplary computer system 100 may be configured as an IPC SPARCstation manufactured by Sun Microsystems, including a high-resolution monitor (e.g., 1,160 pixels by 900 pixels and 256 levels of gray for each of the red, green and blue channels) and a high-speed computer (e.g., 16 million instructions per second).

Figure 1A:
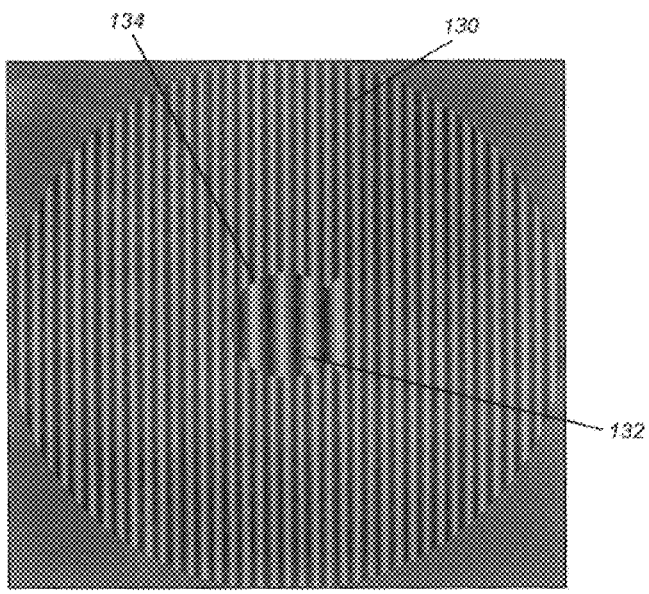
FIGS. 1a and 1b are plan views of exemplary visual stimuli displayed in accordance with the present invention, particularly illustrating a test window with a test pattern superimposed over a background.
Figure 1B:
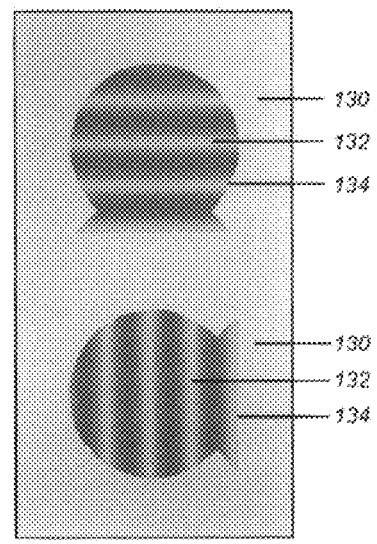

Exemplary computer 102 is configured to display on monitor 104 visual stimuli in the form of a background 130 and a test pattern 132. Test pattern 132 is displayed within a test window 134 which is superimposed over background 130. Both the background 130 and the test pattern 132 are displayed with a contrast and a spatial frequency. As illustrated in FIG. 1a, exemplary background 130 and test pattern 132 may be displayed as a plurality of light and dark vertical stripes which alternate in a substantially sinusoidal manner. Alternatively, as shown in FIG. 1b, the stripes may be horizontal. Other terminology describing the stripes may be sine-wave gratings.

Figure 18:
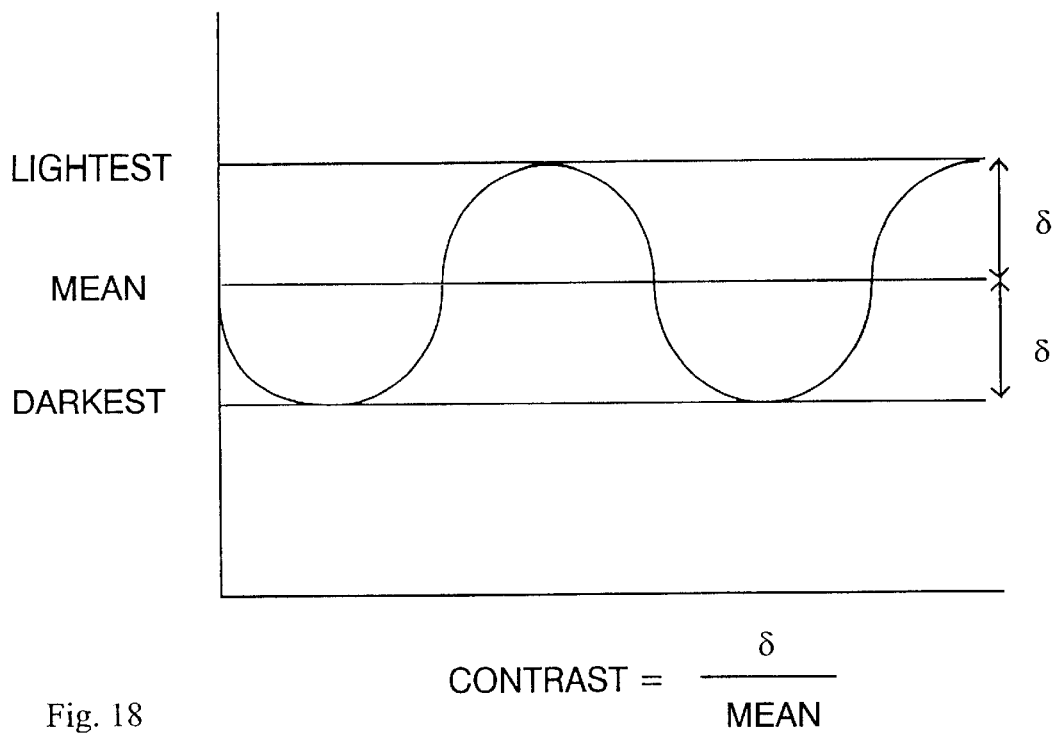
FIG. 18 is a graphical view of a sinusoid, illustrating principles of contrast.

To discuss the respective contrasts at which the background 130 and the test pattern 132 are displayed, reference is made to FIG. 18. Contrast may be defined as the ratio between the lightest or the darkest portion of the stripes and the mean value of the stripes, compared to the mean value of the stripes. This difference is shown as δ, and the mean value is defined as the gray level of the light and dark stripes. Accordingly, a contrast of 5% indicated that the brightest portion of the light stripes (i.e., the peak) are 5% lighter than the average gray level, and that the darkest portion of the dark stripes (i.e., the troughs) are 5% darker than the average gray level.

Figure 19:
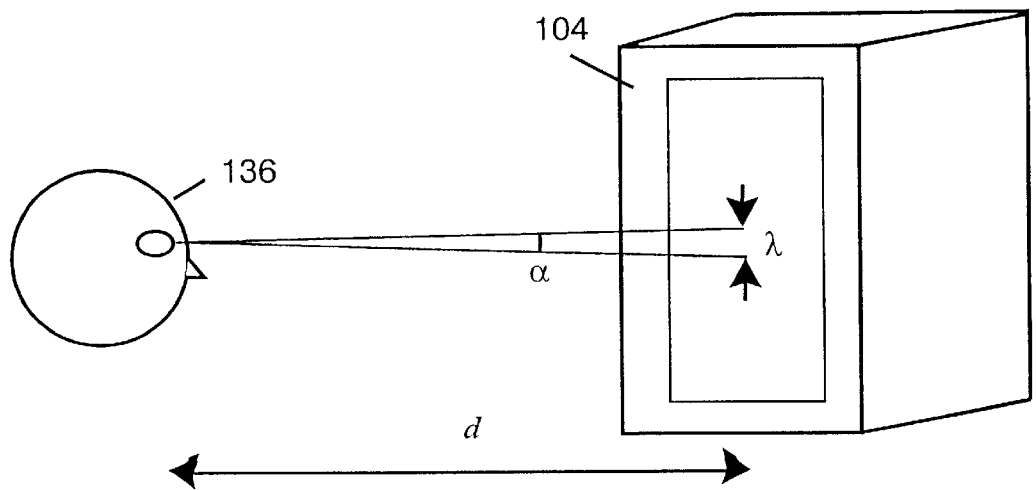
FIG. 19 is a schematic view of a subject and a monitor of the computer system of the invention, illustrating principles of visual angle.

To discuss the spatial frequencies of the background 130 and the test pattern 132 in more detail, reference is made to FIG. 19. The respective spatial frequencies at which the background 130 and the test pattern 132 are displayed may be defined as the rates at which the respective stripes repeat. A subject 136 of whom contrast sensitivity for motion discrimination is to be measured is positioned a distance d from monitor 104. A visual angle α accordingly exists between the subject 136 and the monitor 104. In accordance with the present invention, the subject 136 is positioned with respect to the monitor 104 such that visual angle α is defined to be 1 degree for about every 1 centimeter (cm) of arc length λ. To yield such a relationship between visual angle α and arc length λ, the subject 136 is positioned about 57 cm from the monitor 104 (i.e., distance d is about 57 cm). In this regard, the respective spatial frequencies at which the background 130 and the test pattern 132 are displayed are measured in cycles per degree (of visual angle). For example, if the spatial frequency of the test pattern 132 is 1 cycle per degree (cpd), then there would be one light stripe and one dark stripe for about every 1 cm on the monitor 104 when the subject 136 is positioned about 57 cm away. As shown in FIG. 1a, the background 130 is being displayed at about 2 cpd while the test pattern is being displayed at about 1 cpd.

Exemplary background 130 and test pattern 132 have a spatial relationship with respect to each other in that the background is substantially larger than the test pattern, for example, on the order of about 5 times larger. In terms of the visual angle, the background 130 may be displayed on monitor 104 to subtend about 20 degrees of visual angle, while the test pattern 132 may be displayed to subtend about 4 degrees of visual angle. The test window 134 is preferably centered within the background 130 and in the form of a familiar shape for children, for example, a fish. Generally speaking, exemplary test window 134 is substantially circular.

The contrast at which the background 130 is displayed and the contrast at which the test pattern 132 is displayed are selected from a predetermined range of contrasts which stimulate the visual cortical movement system of the subject 136. As known, the visual cortical movement system of humans includes the magnocellular neurons as described above and is selectively stimulated by contrasts which are less than about 10%. In accordance with the present invention, exemplary background 130 is displayed with a constant contrast of about 5%, and exemplary test pattern 132 is displayed at a contrast ranging from 0% to about 10%, which will be discussed in more detail below.

The spatial frequency at which the background 130 is displayed and the spatial frequency at which the test pattern 132 is displayed are selected from a predetermined range of spatial frequencies which stimulate the visual cortical movement system of the subject 136. In accordance with the present invention, the spatial frequency at which exemplary test pattern 132 is displayed is less than about 5 cycles per degree (cpd), and the spatial frequency at which exemplary background 130 is displayed is a few octaves higher and a few octaves lower than the spatial frequency of the test pattern; in other words, the background spatial frequency is centered about the test-pattern spatial frequency. For example, if the spatial frequency of the test pattern 132 is about 1 cpd, then the spatial frequency of the background 130 may range from about ¼ cpd, 0.5 cpd, 1 cpd, 2 cpd, and 4 cpd (see FIGS. 3a–3f); if the test-pattern spatial frequency is about 0.25 cpd, then the background spatial frequency may range from about 0.0625 cpd, 0.125 cpd, 0.25 cpd, 0.5 cpd, and 1 cpd (see FIGS. 5a–5f).

Figure 20:
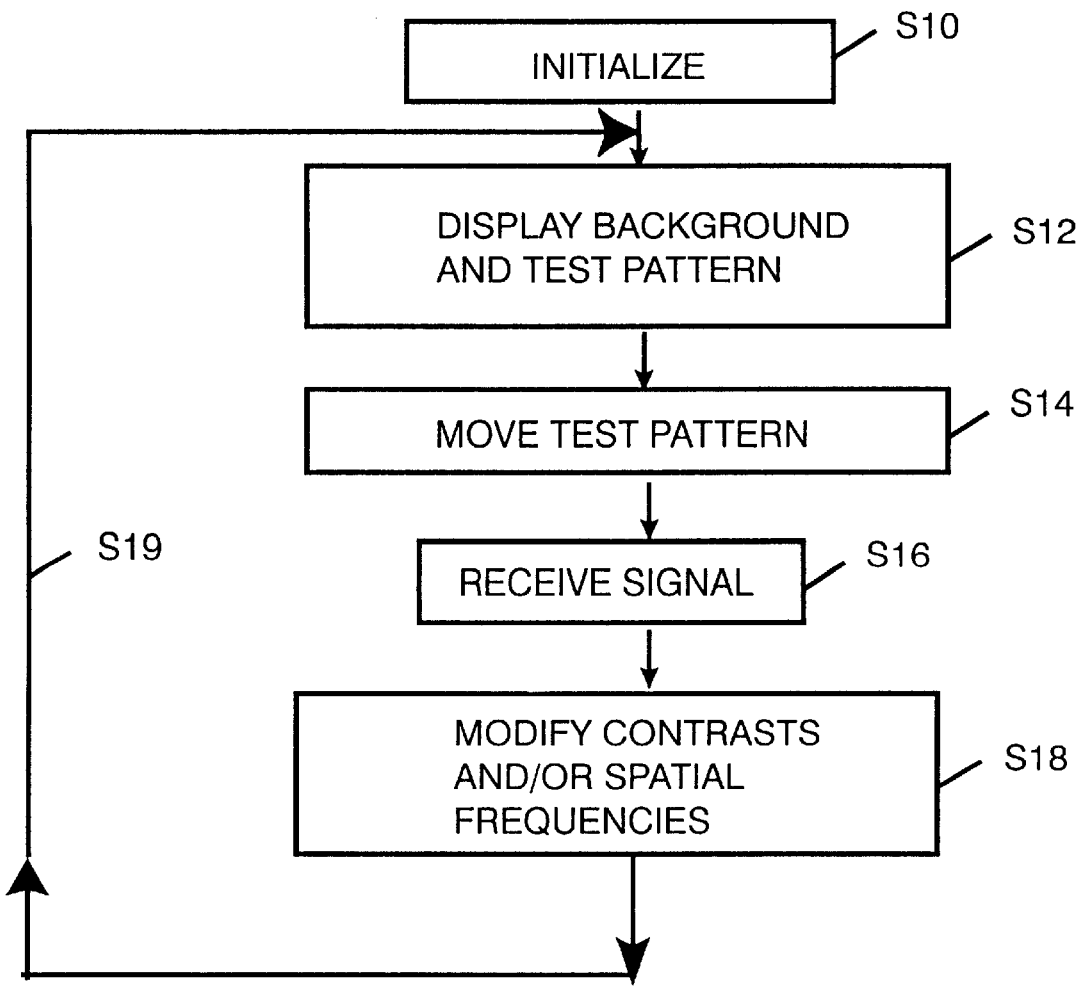
FIG. 20 is a flowchart of exemplary methodology of the present invention for improving contrast sensitivity for motion (or direction) discrimination.
Figure 21:
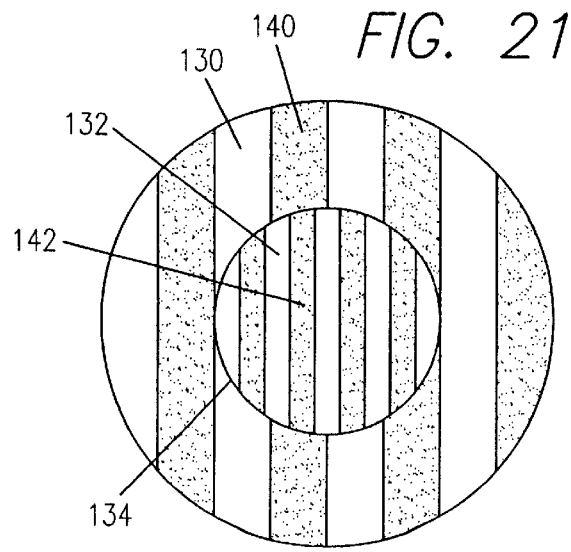
FIG. 21 is a schematic view of visual stimuli, specifically a background and a test pattern, displayed with a contrast and a spatial frequency in accordance with the present invention, particularly illustrating the test pattern in an initial position.

In accordance with the present invention, to measure the contrast sensitivity for motion discrimination of the subject 136, exemplary computer system 100 is configured to implement an interactive process employing a two-alternative forced choice task. The methodology of the present invention is generally represented by the flowchart of FIG. 20, which includes a preliminary initialization step (block S10) which will be discussed below. Referencing FIG. 21, upon activation, for example, by the subject 136 manipulating the mouse 110, exemplary computer 102 displays on monitor 104 a background 130 with a contrast (e.g., about 5%) and a spatial frequency (e.g., about 0.5 cpd) and a test pattern 132 within test window 134 with a contrast (e.g., about 5%) and a spatial frequency (e.g., about 1 cpd) (block S12). One of the dark stripes of the background 130 is referenced with numeral 140, and one of the dark stripes of the test pattern 132 is reference with numeral 142. The computer 102 will then move the test pattern 132 within the test window 134 (block S14). For example, in FIG. 22a the test reference stripe, which is indicated by numeral 142', is positioned to the right of where it was initially (i.e., as shown in FIG. 21), and in FIG. 22b the test reference stripe, which is indicated by numeral 142", is positioned to the left of where it was initially. Exemplary computer 102 may randomly select to move the test pattern 132 either to the right or the left. Although the test pattern 132 may be moved in any desired degree or length, it is preferable to shift the stripes either left or right a distance substantially equal to about one-half of the width of one of the stripes, which is equal to about 90 degrees of spatial frequency, which can be seen in FIGS. 20 and 22. (For the sake of clarity, the stripes of the background 130 and the test pattern 132 alternate in accordance with a square wave, rather than a sinusoid, in FIGS. 20 and 22.)

Figure 22A:
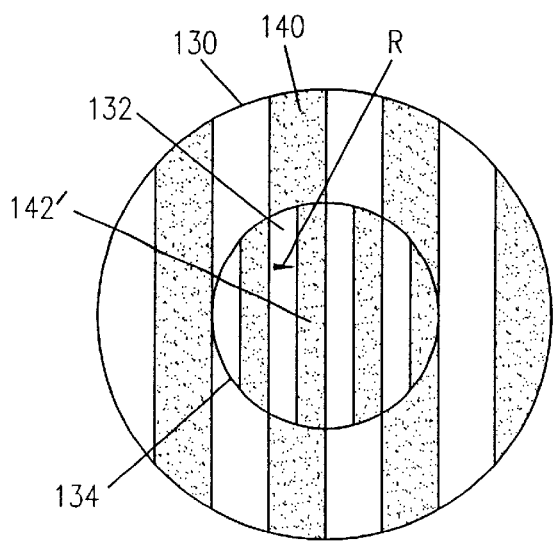
FIG. 22a is a schematic view of the background and the test pattern of FIG. 21, particularly illustrating the test pattern in a second position which is to the right of the initial position, in accordance with a preferred embodiment of the invention.
Figure 22B:
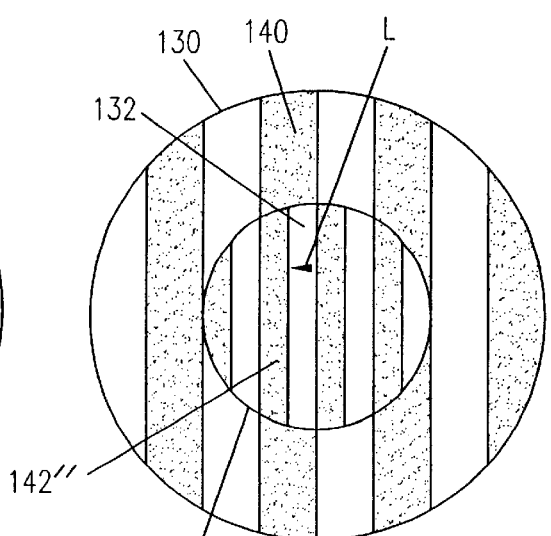
FIG. 22b is a schematic view of the background and the test pattern of FIG. 21, particularly illustrating the test pattern in an alternative second position which is to the left of the initial position, in accordance with a preferred embodiment of the invention.

Both the initial position of the test pattern as shown in FIG. 21 and the moved position of the test pattern as shown in either FIG. 22a or 22b are displayed for a predetermined period. The periods for which the test pattern is displayed in each position is for a length which causes apparent motion of the stripes of the test pattern. Apparent motion of the stripes of the test pattern 132 may be induced in the subject 136 when the test pattern displayed in the initial position (as in FIG. 21) and the test pattern displayed in either of the final positions (as shown in FIGS. 22a and 22b, with apparent motion indicated by arrows R and L, respectively) for less than about ²⁄₁₀ second, for example. In a preferred embodiment of the invention, the test pattern 132 is displayed in both the initial and final positions for about 150 milliseconds (0.15 seconds).

Before displaying the initial position of the test pattern 132 and after displaying the final position of the test pattern (i.e., before and after moving test pattern), computer 102 does not display the background 130 or the test window 134 on monitor 104, in that it may be preferable for the monitor to be blank or to display all the pixels with a gray value. Alternatively, the background 130 may remain displayed on the monitor 104 with only the test window 134 being blank. Exemplary computer 102 may store images of the test pattern 132 in the initial position shown in FIG. 21 and in each of the possible final positions as shown in FIGS. 22 in files in memory. To display the computer 102 may output the image file of the test pattern 132 in the initial position for the predetermined period and then output either of the image files of the test pattern 132 in the final position for the predetermined period. When image files are not output by the computer 102, the monitor 104 does not display any image. The image files may be in the form of pixel maps (i.e., pixmaps) as known in the art.

After moving the test pattern 132 within the test window 134 (i.e., after displaying the test pattern in one of the final positions), exemplary computer 102 is configured to receive a signal from the subject 136 indicative of the direction the subject believes the test pattern moved (block S16). The subject 136 may provide the signal through one of the input devices, that is, the keyboard 108, the mouse 110, or the microphone 112. The computer 102 may prompt the subject 136 for a response, for example, with a graphical user interface on the monitor 104 or with an audible through the speaker 106. Alternatively, the subject 136 may be initially instructed to input the signal when the monitor 104 is blank after the final position of the test pattern 132 is displayed. In a preferred embodiment of the invention, the subject 136 may use the mouse 110 which has a plurality of input buttons, including a right button 144R and a left button 144L. If the subject 136 believes that he or she saw the test pattern 132 move to the right, then the subject may press right button 144R of the mouse 110 to provide the signal. If the subject 136 believes that he or she saw the test pattern 132 move to the left, then the subject may press the left button 144L to provide the signal.

Upon receiving the signal, the computer 102 determines whether the subject 136 is correct or not in perceiving the movement of the test pattern 132. If the computer 102 displayed the test pattern 132 in the right final position shown in FIG. 22a and the subject 136 pressed the right button 144R, or if the computer displayed the test pattern 132 in the left final position shown in FIG. 22b and the subject pressed the left button 144L, then the computer 104 would determine that the subject input a correct signal. Conversely, if the computer 102 displayed the test pattern 132 in the right final position shown in FIG. 22a and the subject 136 pressed the left button 144L, or if the computer displayed the test pattern 132 in the left final position shown in FIG. 22b and the subject pressed the right button 144R, then the computer 104 would determine that the subject inputted an incorrect signal. In response to receiving a signal from the subject 136, the computer 102 modifies either the contrast of the test pattern 132 or the spatial frequency of either the background 130 or the test pattern 132 (block S18), as discussed below.

If the signal input by the subject 136 is correct, then the computer 102 may, for example, decrease the contrast of the test pattern 132, thereby making it more difficult to distinguish the light and dark stripes. After modifying the test pattern contrast, the computer 102 may then redisplay the background 130 (the contrast and the spatial frequency of which has not been modified in this example) and display the test pattern 132 with the same spatial frequency as initially displayed and with the decreased contrast (loop S20 and block S12). After the predetermined period (e.g., 150 msec), the computer 102 moves test pattern 132 with the modified contrast within the test window 134 (block S14), awaits to receive a signal from the subject 136 (block S16), and modifies the contrast of the test pattern 132 again and/or the spatial frequency of either the background 130 or the test pattern (block S18). This process may repeat a plurality of times. Although any specified range may be possible which stimulates the visual cortical movement system of the subject 136, in a preferred embodiment of the invention the contrast of the test pattern 132 may vary between, for example, 5% and 0.5% at 0.5% increments (i.e., 5%, 4.5%, 4.0%, . . . 0.5%), and may include 0.25% and any other desired contrast as well.

Rather than decreasing the contrast of the test pattern 132 in response to a correct signal, the computer 102 may modify the spatial frequency of the background (block S18). For example, if the test pattern 132 is being displayed at a spatial frequency of about 1 cycle per degree (cpd), then the computer 102 may modify the spatial frequency of the background from 2 octaves lower or 0.25 cpd, 1 octave lower or 0.5 cpd, the same or 1 cpd, 1 octave higher or 2 cpd, to 2 octaves higher or 4 cpd. After modifying the spatial frequency of the background 130, the computer 102 may then display the background 130 as modified and the test pattern 132 and move the test pattern within the test window (blocks S12 and S16) as described above. At each of these background spatial frequencies, the computer 102 may increase or decrease the contrast of the test pattern 132 a plurality of times in response to correct or incorrect signals.

Also in response to a correct signal, the computer 102 may modify the spatial frequency of the test pattern 132 (block S18). For example, if the test pattern 132 is being displayed with a spatial frequency of about 0.5 cpd, then the computer 102 may increase this frequency 1 octave to 1 cpd. In accordance with a preferred embodiment of the present invention, the test pattern 132 may be displayed at a spatial frequency selected from a range of predetermined frequencies including 0.25 cpd, 0.5 cpd, 1.0 cpd, and 2.0 cpd. After modifying the spatial frequency of the test pattern 132, the computer 102 may then display the background 130 and the test pattern 132 as modified and move the modified test pattern within the test window 134 (blocks S12 and S16) as described above. At each of these test pattern spatial frequencies, the computer 102 may increase or decrease the contrast of the test pattern 132 and/or the spatial frequency of the background 130.

The inventor has discovered that by repeatedly following the method illustrated by the flowchart of FIG. 20 that the contrast sensitivity for motion (or direction) discrimination of the subject 136 will increase. When this contrast sensitivity increases, the reading ability of the subject 136 increases. (Contrast sensitivity, which will be discussed in more detail below, is defined as the inverse of contrast threshold, which is the minimum contrast at which the subject can distinguish sideways movement.) The subject 136 may be a child with so-called normal reading ability or any other person—adult or child—who suffers from one form of dyslexia or another. As dyslexia of various degrees and types may afflict as much as 50% of the population as a whole, the benefit to society is essentially boundless. Although it is often preferable to initially measure the contrast sensitivity for motion discrimination of the subject 136, this measurement does not need to be undertaken in order to improve the contrast sensitivity.

In many applications of the present invention, schools, for example, may make the present invention available to first and second graders for practice. To entice such young children to practice, the present invention may be configured as a "fish game" in which the object of the game is being able to answer correctly the question, "Which way did the fish stripes move?" As they play the fish game, the children improve their contrast sensitivity for motion discrimination and thereby improve their ability to read. If the child is dyslexic, the improvement will be great; whereas if the child is of normal vision or reading ability, the improvement will be less marked. In any case, if all the children of a grade-school class play the game, it is not necessary to determine which children are dyslexic as all children improve. The inventor has determined that playing the fish game for as little as about 5 minutes to 10 minutes a week for about 8 weeks significantly improves contrast sensitivity for motion discrimination. As the computer-readable instructions for configuring computers to operate in accordance with the present invention may be readily provided via conventional storage media (e.g., CD-ROM 114 or floppy disc 116) or via an Internet connection 122, and as the present invention uses visual exercises (e.g., the left-right movement of vertical stripes) rather than language to improve reading rates, schools and organizations all over the world may implement the fish game to improve the reading rates of children regardless of educational or ethnic backgrounds.

Figures 1, 16:
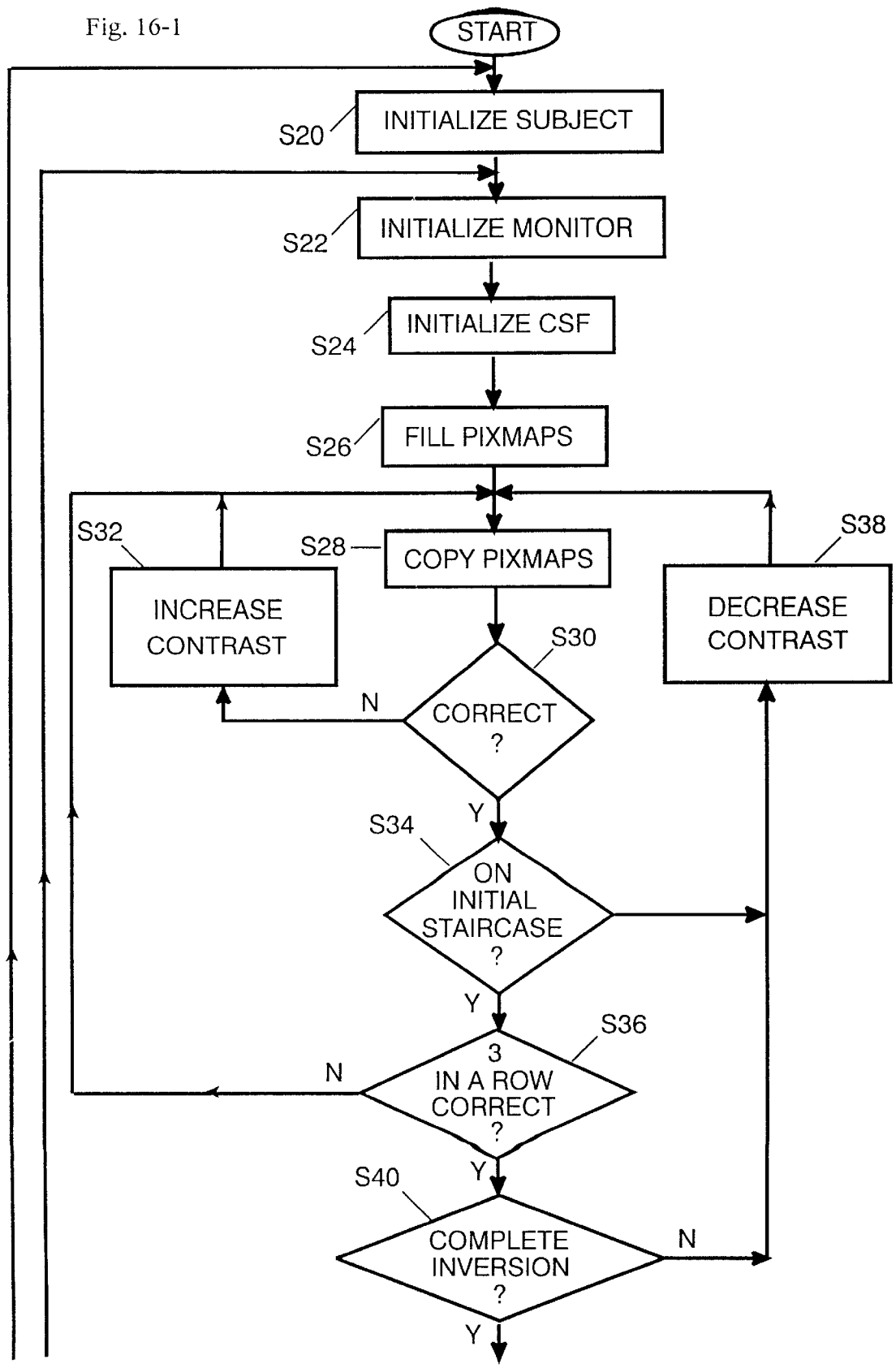
FIG. 16 is a flowchart illustrating steps in exemplary methodology for measuring and improving contrast sensitivity of a subject in accordance with the present invention.
Figures 2, 16:
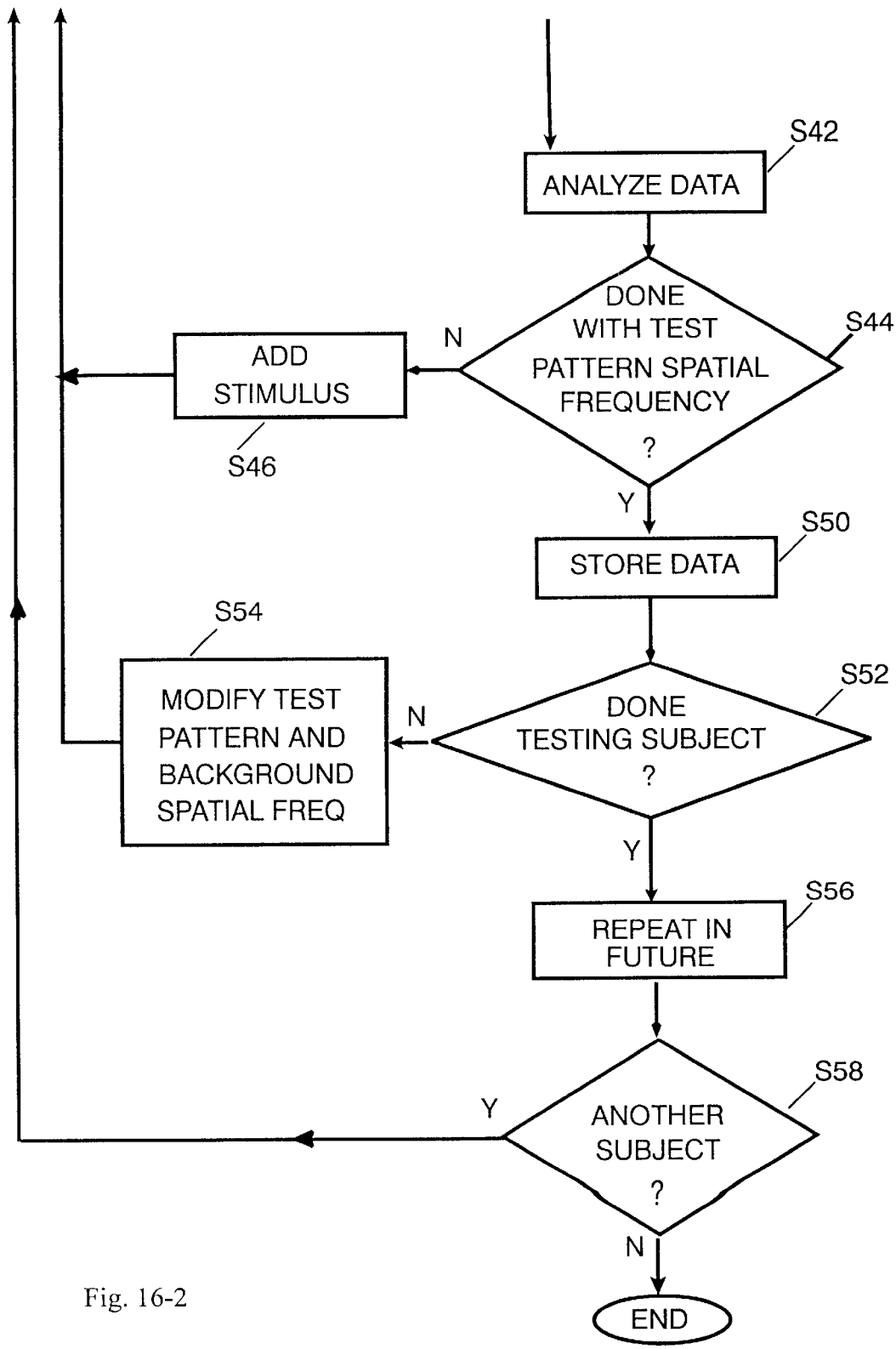

The methodology of the present invention has been described thus far in a general sense in that the test pattern 132 is moved with respect to the background 130, a signal is received from the subject, and the contrast and/or the spatial frequency of the test pattern 132 or of the background 130 is modified, with the process being repeated a plurality of times to improve contrast sensitivity for motion discrimination. A more specific and preferred embodiment of the present invention is illustrated in FIG. 16 which, in addition to improving contrast sensitivity, measures contrast sensitivity for motion discrimination and determines the contrast sensitivity function (CSF) for motion discrimination for the subject 136. To measure CSF, a staircase procedure is implemented to determine a contrast-sensitivity threshold for each spatial frequency of the test pattern 132 at each spatial frequency of the background 130.

Exemplary methodology for measuring contrast sensitivity as illustrated in FIG. 16 may include a plurality of preliminary initialization steps. For example, data on the observer or subject 136 may be input into the system 100 (block S20), including name, date of birth, visual acuity (i.e., 20/20, etc.), viewing distance d, and so on. Parameters of the monitor 104 may also be entered into the system 100 (block S22), such as color and gamma functions. Contrast sensitivity function (CSF) parameters may also be initialized (block S24), which may include the generation of the visual stimulus patterns for the spatial frequencies of the background 130 and the test pattern 132.

The computer 102 may then generate image files for the background 130 and the test pattern 132 in the form of pixel maps or pixmaps (block S26). As described above, the pixmaps may include the test pattern 132 in the initial position (see FIG. 21), in a right position (see FIG. 22a), and in a left position (see FIG. 22b), as well as a pixmap for the background 130. Generally speaking, the present invention measures and improves contrast sensitivity for motion discrimination, which specifically includes direction (i.e., left-right) discrimination and orientation (i.e., vertical-horizontal) discrimination. Accordingly, the pixmaps may also include the test pattern 132 in a vertical position and in a horizontal position (see FIG. 1b). The pixmaps may then be copied to the monitor 104 (block S28) as described above. Although variable, the pixmap for the background 130 may be displayed at a preferred contrast of, e.g., 5% and a specified spatial frequency. The test pattern 132 is displayed at a specified contrast and spatial frequency.

Figure 23:
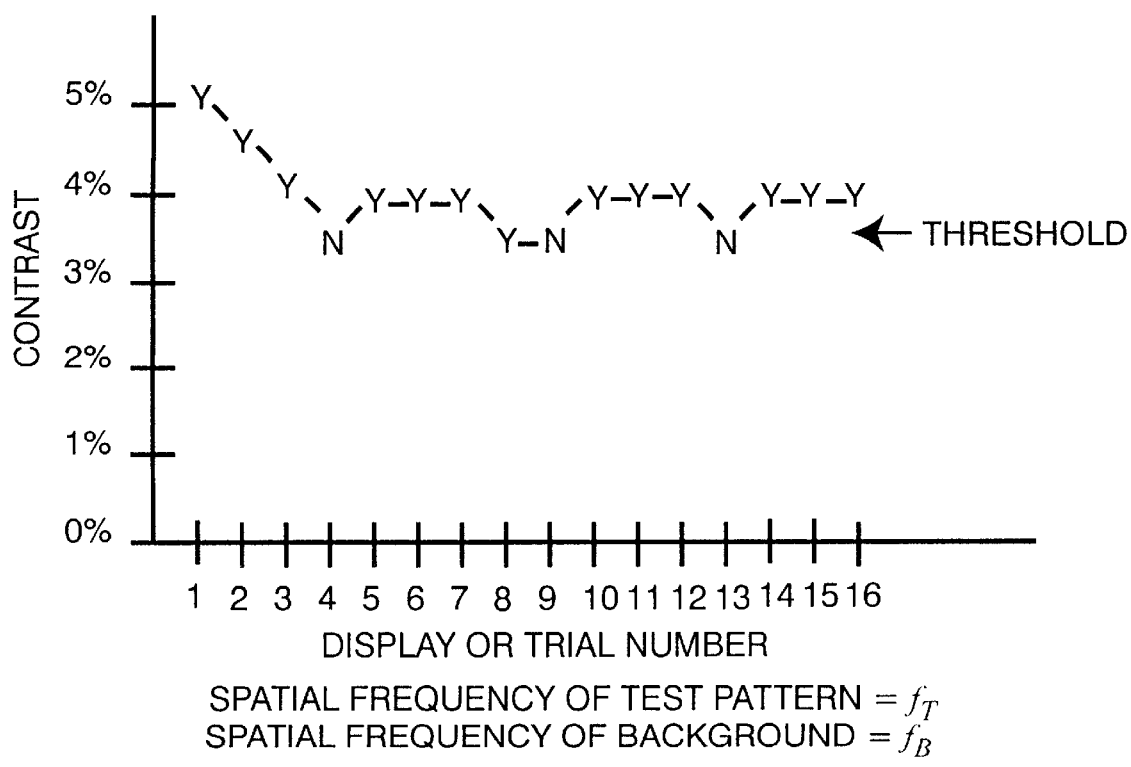
FIG. 23 is a graphical view illustrating steps in an exemplary method of the present invention for determining a contrast-sensitivity threshold of a subject at predetermined spatial frequencies of the test pattern and the background.

With additional reference to FIG. 23, to determine the contrast-sensitivity threshold of the subject 136 for a specified test-pattern spatial frequency $f_T$ (e.g., 0.25 cpd, 0.5 cpd, 1 cpd, and 2 cpd) at a specified background spatial frequency $f_B$, the spatial frequencies at which the test pattern 132 and the background 130 are displayed are held constant, while the contrast at which the test pattern is displayed is, varied, as shown on the vertical axis. For example, if the subject 136 indicates a wrong direction (block S30), the contrast of the test pattern 132 is increased (block S32) one step, e.g., from 3.5% to 4% (while holding the spatial frequency constant), until the subject 136 indicates the direction correctly.

It is then determined whether the subject 136 is on the staircase (block S34). This is determined when the subject 136 incorrectly indicates the direction the test pattern 132 moves. For example, as shown in FIG. 23, the subject 136 correctly indicated the direction of the test pattern 132 when displayed with contrasts of 5%, 4.5%, and 4%, as indicated by a "Y" for trial Nos. 1, 2, and 3. When the subject 136 incorrectly indicates the direction, as shown by the "N" at trial No. 4, the subject is on the staircase, and the contrast of the test pattern 132 is increased one step (block S32), for example, from 3.5% to 4%. The pixmap with the test pattern 132 with a 4% contrast is then copied to the monitor 104 for display (block S28). If the subject 136 correctly identifies the direction the test pattern 132 moved within the test window 134 at the 4% contrast (as indicated by the "Y" at trial No. 5 in FIG. 23), then the computer 102 determines whether a predetermined number of correct responses have been made, for example, three (block S36). If not, then the computer 102 will redisplay the test pattern with the same contrast (e.g., 4%) until the subject 136 indicates the direction correctly for the predetermined number of times, such as three indicated by the "Ys" at trial Nos. 5, 6, and 7.

It is then determined whether a predetermined number of inversions have been completed (block S40), which will be discussed in more detail below. If the predetermined number of inversions have not been completed, then the test-pattern contrast is decreased another step (block S38), for example, from 4% to 3.5%. If the subject 136 incorrectly indicates the direction at this new test-pattern contrast, then the contrast remains the same (blocks S30, S36, and S28), for example, at 3.5%. If the subject indicates the direction incorrectly at this contrast, as indicated by the "N" at trial No. 9 in FIG. 23, then the contrast of the test pattern increases one step. This switching from a higher contrast to a lower contrast and from a lower contrast to the higher contrast (e.g., 3.5% to 4% and 4% to 3.5%) is defined as an inversion. A run is initiated and terminated at an inversion. The computer 102 monitors the number of runs which occur in determining the threshold of the subject 136 for the particular spatial frequencies of the test pattern and the background, with the threshold being defined as the lower contrast of the run. The predetermined number of runs in the example shown in FIG. 23 is six, with each inversion indicated by trial Nos. 1–4, 4–7, 7–9, 9–12, 12–13, and 13–16. Accordingly, for the example illustrated in the drawings, the contrast-sensitivity threshold for the subject 136 at a test-pattern spatial frequency $f_T$ and a background spatial frequency $f_B$ is 3.5%.

Once the predetermined number of inversions have been completed (block S40), the data (such as those graphically illustrated in FIG. 23) are analyzed (block S42) to determine the contrast-sensitivity threshold at the specified spatial frequencies. If the subject 136 has not yet completed testing at all of the predetermined spatial frequencies of the background 130, that is, two octaves higher and two octaves lower than, as well as equal to, the test-pattern spatial frequency as described above (block S44), then the computer 102 may add a stimulus (block S46), for example, an audible signal, indicating that the subject 136 has completed one specified test-pattern spatial frequency at one background spatial frequency, and will begin, for example, testing at another background spatial frequency for the same test-pattern spatial frequency. Accordingly, the CSF for the new frequencies may then be initialized (block S24).

Figure 24:
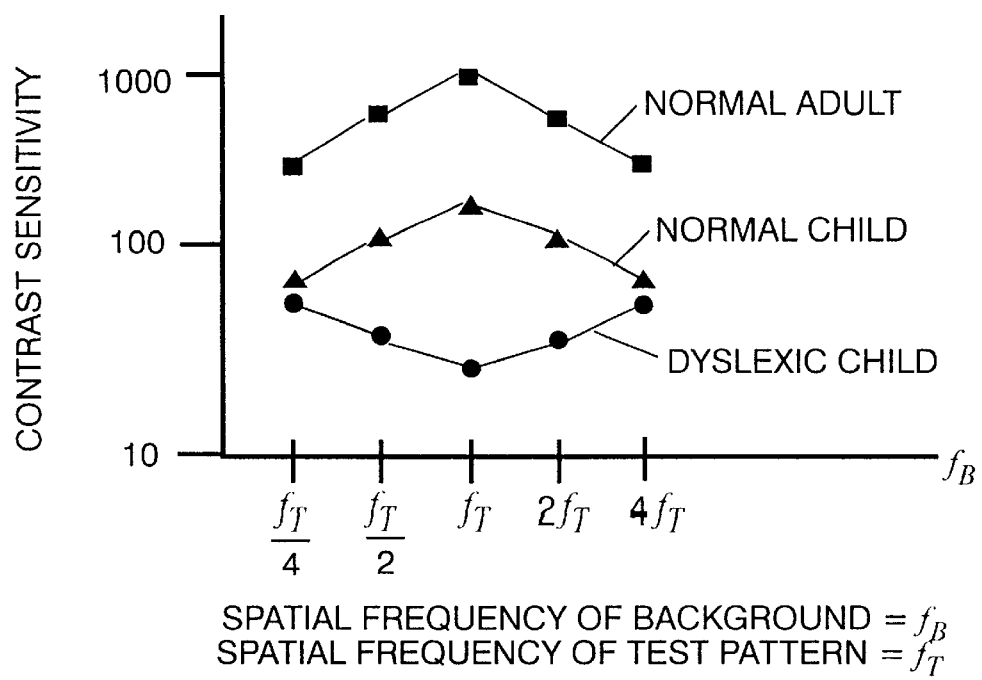
FIG. 24 is a graphical view illustrating exemplary contrast sensitivity functions (CSFs) of a normal adult, a normal child, and a dyslexic child.

This process is repeated until the subject 136 has been tested for all of the predetermined background spatial frequencies for the specified test-pattern spatial frequency (block S44). The data for the specified test-pattern spatial frequency may then be stored (block S50) to generate a contrast sensitivity function (CSF) for the specified test-pattern spatial frequency, as illustrated in FIG. 24. Contrast sensitivity (the vertical axis) is the inverse of contrast-sensitivity threshold. For example, in the example shown in FIG. 23, a contrast-sensitivity threshold of 4% (i.e., 0.04) yields a contrast sensitivity of 25. FIG. 24 exemplifies the CSF of a normal adult, a normal child, and a child with dyslexia As can be seen, the dyslexic child has lower contrast sensitivities than the normal child, especially when the background spatial frequency $f_B$ equals the test-pattern spatial frequency $f_T$, which will be discussed in more detail below.

If the subject 136 has not been tested for all of the predetermined test-pattern spatial frequencies after completing the testing for a particular test-pattern spatial frequency (block S52), then the test-pattern spatial frequency is modified (e.g., increased or decreased within the preferred predetermined range of 0.25 cpd, 0.5 cpd, 1 cpd, and 2 cpd) (block S54), and the process returns to block S24.

The preferred methodology described thus far measures the CSFs of the subject 136. In addition, by being tested, that is, by repeatedly watching the test pattern 132 shift left and right at the predetermined contrasts and spatial frequencies, the CSFs of the subject improve. For example, if the subject 136 has a CSF like that of a dyslexic child shown in FIG. 24, then the process of being tested (i.e., playing the fish game) improves the contrast sensitivities of the dyslexic child. The inventor has discovered that by repeating the test in the future (block S56), for example, once or twice a week for up to eight weeks, significantly improves the CSFs of all children, but especially in dyslexic children, so that the CSF of a dyslexic child will be reshaped to look like the CSF of a normal child (see FIG. 23). The testing process may be repeated for a plurality of subjects (block S58).

The above-described apparatus and methodology of the invention is capable of being alternatively configured for many applications. For example, rather than being displayed at a single spatial frequency at one time, the background 130 may be displayed with a plurality of spatial frequencies, e.g., as a natural scene. This is particularly beneficial in testing children in that the fish game may be implemented more realistically with the fish-shaped test window 134 "swimming" through a natural aquatic background 130. Additionally, although the present invention has been described in relation to the contrast sensitivity for direction discrimination, the principles of the present invention may be readily applied to measuring and improving contrast sensitivities for all motion discrimination of the visual cortical movement system.

The principles of the present invention are further exemplified in the examples which follow.

EXAMPLE

The following examples investigate whether entertaining visual exercise improves the reading performance of both normal and dyslexic children in grades 1 to 3. This task was entertaining by using a familiar object (e.g., a striped fish) in an unfamiliar task. The visual exercise was provided by using auditory feedback to enable the child to quickly learn to see dim stripes that moved to the left or to the right. This study revealed the importance of mapping out direction discrimination CSFs for a four-octave range of background frequencies centered around test frequencies spanning four octaves, from 0.25 cpd to 2 cpd, for both rapid screening and remediation. One octave is a doubling in frequency.

Testing was performed on a random sample of children aged 5 to 8 years old from a local elementary school. Children were included in the study if they had 20/20 visual acuity, normal intelligence, as verified by standardized tests administered by the school, no known organic disorders, and no known behavioral disorders. Only one-third of the Kindergarten children were included in this study. The other two-thirds of the Kindergarten children could not push a mouse button while maintaining fixation on the screen, thereby being unable to perform the 2AFC task for measuring the CSF. The sample of students who participated in this study in grades 1 to 3 was a diverse population representative of the range of normal children in each class tested, as verified by the school's principal who was also the learning specialist, and each teacher. A total of 35 children were included in this study, five children in kindergarten, ten children in first grade, five normal readers and five children with reading problems in each of grades 1 to 3. Five children were used in each group, so that a completely counterbalanced design was used, distributing the variability equally across different grade levels and type of reader.

A standardized reading test The Dyslexia Screener (TDS) was used to determine whether a child was a normal reader. Data were collected during the normal school day, during non-directed teaching time, which was usually during computer lab. By testing children during school hours both normal readers and children with reading problems were able to be tested at regular weekly intervals. Each child was tested each morning from 8 o'clock to 12 noon with sessions lasting from 5 to 10 minutes once per week. A subset of the practiced observers, i.e., m1, a1, s1, l1, who were dyslexic required one eye to be patched for about one month to establish eye dominance. Otherwise, test patterns, especially those that were low frequency, appeared to oscillate back and forth, instead of moving in one direction. The CSFs for the normal adult in both CSF tasks were the average of a male and a female both 43 to 44 years old, with 20/20 acuity and normal intelligence.

All observers sat at a viewing distance of 57 cm from the screen for all tasks in this study, enabling high spatial frequencies up to 8 cyc/deg to be displayed. During the first session, the student's visual acuity was measured with a hand-held eye chart The TDS was administered to determine the child's reading grade level and whether the child exhibited reading problems. The observer's CSF to discriminate between orthogonally oriented brief 150 msec patterns was measured. It took two to three sessions to measure each child's orientation discrimination CSF. This CSF was then used to generate individualized filtered text that was stored on the hard disk.

Reading rates for equal size filtered and unfiltered text were measured in a subsequent session. Reading rates were used to evaluate a child's reading performance, since this task relies on a child's ability to decode words, and cues such as context affect performance. Text was chosen that was entertaining, and easy to read, so that the difficulty of the text did not limit reading performance. The direction discrimination CSFs were measured, following the reading rate session, once a week for the next 8 weeks, each week the CSF for a new test frequency was mapped out for a 4-octave range of background frequencies. Therefore, each replication for a particular set of test and background patterns was spaced about one month apart.

Approximately half of the children in grades 1 to 3 were tested on the direction discrimination task from 12 to 20 weeks. Only these children had the benefit of more than one practice threshold, and their data are plotted accordingly in the graphs depicting individual data. Finally, in the last three sessions, reading rates for both unfiltered and filtered text, having a high mean luminance, 67 cd/m$^2$, as used for all tests up to this point, and a low mean luminance of 8 cd/m$^2$, to enable grayscale and colored text, red, green, blue, and yellow, to be set to equivalent mean, minimum, and maximum luminances, were measured. A questionnaire was administered during the last session to determine whether the student liked being tested and whether the student noticed any improvements in their visual function and/or reading performance.

Direction-discrimination contrast sensitivity functions (CSFs) were measured to provide interactive training using a temporal two alternative forced choice (2AFC) task with feedback During these sessions, a test pattern of a vertical sine-wave grating was presented in the form of a fish, as shown in FIG. 1$a$, with the fish-shaped test pattern subtending 4 degrees of visual angle at a viewing distance of 57 cm. The edges of the test pattern provided the outline of the fish that was surrounded by a circular background of a vertical sine-wave grating. The test patterns and backgrounds were presented abruptly for 150 milliseconds (msec) using simultaneous metacontrast. The vertical stripes covering the fish were moved by phase shifting each stripe by 90 degrees either to the left or the right from one 150-msec interval to the next The subject was asked to identify the direction of motion, that is, whether the stripes moved to the left or to the right, by pressing one of two mouse buttons indicating direction. Initially, test and background spatial frequencies were presented at a 5% contrast. The subject initiated the practice session by pushing the middle mouse button. During the practice session, the contrast of the fish pattern was increased one step on each incorrect response; otherwise the contrast remained constant. When the subject felt comfortable with the task, the middle mouse button was pushed again to begin the test session.

The only difference between the test and the practice session was that each time the subject chose the direction of movement correctly, the contrast of the test pattern was reduced one step until the first incorrect response. A 2AFC double-staircase psychophysical procedure as known in the art was then initiated to measure the contrast threshold needed to detect the left-right movement correctly at least 79% of the time. This 2AFC psychophysical task enabled measuring the most sensitive, repeatable contrast thresholds possible. The subject was instructed when to progress from the practice session to the test session. About three practice trials were completed before moving to the test session. Each threshold consisted of approximately 20 to 30 trials.

Sine-wave gratings of 0.25 cycle per degree (cpd), 0.5 cpd, 1.0 cpd, and 2 cpd were used to characterize the fish-shaped test pattern. Each of the sine-wave gratings was surrounded by one of five different sine-wave backgrounds. The spatial frequency of the background may be equal to the spatial frequency of the test pattern, or may be one or two octaves higher or lower than the spatial frequency of the test pattern. Subjects were given auditory feedback, one short beep or three short beeps, indicating whether the direction of the motion had been correctly identified. This auditory feedback was used to train the subject to discriminate left and right movement at low contrasts.

Vertical sine-wave gratings were used to map out the contrast sensitivity function (CSF) of each subject to discriminate left-right movement. Initially, both the test pattern and the background were displayed at 5% contrast to optimally activate magnocellular neurons. The background and the test pattern were displayed for a short duration of about 150 msec to optimally activate magnocellular neurons and prevent eye movement. The CSFs for direction discrimination were the same for patterns that were presented for 750 msec or 150 msec. The direction discrimination contrast thresholds were grouped into the lowest and highest values and plotted accordingly to show the effects of practicing left-right discrimination one time for each stimulus pattern.

Orientation discrimination CSFs were measured to map the CSF for a 5-octave range of spatial frequencies, from 0.25 cpd to 8.0 cpd, so that the CSF for high spatial frequencies could be used to generate filtered text. The test pattern was a circular fish which subtended a visual angle of 8 degrees at a viewing distance of 57 cm as shown in FIG. 1b. The subject's task was to push a key indicating whether the abruptly presented (e.g., 150 msec) test pattern was vertical (i.e., up or down) or horizontal (i.e., sideways) in orientation. Auditory feedback was given after each pattern to indicate whether the subject chose the orientation of the pattern correctly. A 2AFC staircase procedure was used to measure the contrast threshold function of each subject. Following a short practice session that set the initial contrast of the test pattern, the test run was initiated. At the beginning of the test run, the contrast of the test pattern was decreased one step of 0.5%, each time the observer correctly identified the orientation of the test pattern. Following the first incorrect response, the staircase procedure was used. In the staircase, the subject had to correctly identify the orientation of the test pattern three times in a row before the contrast was decreased one step. The contrast was increased one step each time the orientation of the test pattern was identified incorrectly. Each threshold consisted of approximately 20 to 30 trials.

Based on an assumption is that reading relies on the low-resolution movement system, the present invention evaluates the movement system by measuring the contrast sensitivity for motion discrimination of a subject. From this perspective, dyslexia, which may be defined as a difficulty in reading in a child of normal intelligence and an adult-level acuity (i.e., 20/20) but with low contrast sensitivity for motion discrimination, is explained as a difficulty in visually perceiving words on a page that could be readily decoded otherwise. Tests of the acuity system, such as visual acuity using long-duration patterns, reveal no differences between children with normal reading and children with reading problems. In contrast, differences between children with normal reading and children with reading problems are revealed only by tests of the visual cortical movement system.

Reading rates were measured for continuously scrolled text both before and after measuring Contrast Sensitivity Functions (CSFs) to discriminate left-right movement for 35 normal children aged 5 to 8 years old. When compared to age-matched normal readers, the direction-discrimination CSFs were 3 to 4 times lower for dyslexics and resembled the CSFs of 5-year-old children. Moreover, the CSFs of normal and dyslexic children revealed a different pattern of results when test and background frequencies were equal, thereby enabling rapid screening for dyslexia at 6 and 7 years old.

Humans form memories after single experience by "rewiring" circuits in the brain. Perceptual learning, which refers to the ability of experience to alter the sensitivity or timing of one's perceptual machinery, is a form of memory that resides within the circuits in the brain that process sensory information. Experience dependent changes in the numbers of neurons and synaptic connections have been observed in the visual cortex even as early as primary visual cortex. Experience may have particularly strong and rapid affects on the developing visual cortex and is also capable of affecting the mature nervous system.

The circuits that underlie motion discrimination are plastic and can be rewired by experience. Accordingly, practicing the task used to measure contrast sensitivity for motion discrimination increases the subject's contrast sensitivities. To rapidly remediate reading disorders, a subject repeats the above-described method for about 5 minutes to 10 minutes per week for about eight weeks. By using feedback and practice, the subject will significantly improve motion discrimination CSFs up to 8 fold on average and reading rates up to 9 fold on average. The evidence that is presented below support the concept that networks in magnocellular streams play a major role in reading and are maturing in all 5- to 8-year-old children. Since rapid remediation was found using a direction discrimination task, the most rapid remediation occurring for 6- to 7-year-old children, which indicates that these children are transitioning through a critical period for movement discrimination at that age.

Dyslexics have anomalies in their magnocellular networks, demonstrated by: (1) higher contrast thresholds to detect brief patterns, (2) an impaired ability to discriminate both the direction and the velocity of moving patterns, and (3) unstable binocular control and depth localization when compared to age-matched normals. Dyslexics had selective deficits in the magnocellular layers of both the visual (lateral geniculate nucleus) and auditory (medial geniculate nucleus) regions of the thalamus. However, there were no deficits in the parvocellular regions of the thalamus. Losses in the responsiveness of the magnocellular neurons found in the lateral geniculate nucleus of dyslexics will affect all subsequent levels of processing that receive input from these magnocellular neurons. Brain recordings using functional Magnetic Resonance Imaging (fMRI) found that when dyslexics were compared to normal controls, there were clear deficits to moving patterns in the fMRI activation of all extrastriate visual areas, most noticeably of the visual-motion area or Medial Temporal cortex (MT), where the MT failed to be activated by coherently moving random dot patterns that produced a large response in non-dyslexic counterparts.

Reading rates were measured for continuous scrolled text both before and after the measurement of contrast sensitivity functions (CSFs) to discriminate left-right movement and were measured for 35 normal children aged 5 to 8 years old. When compared to age-matched normal readers, the direction discrimination CSFs were 3 to 4 fold lower for dyslexics, with the CSFs of dyslexics resembling the CSFs of 5-year-old children.

The direction discrimination CSFs illustrated in FIGS. 2 to 5 show that movement discrimination is developing in all normal children. The direction discrimination CSFs of normal children were 2 to 8 fold lower than a normal adult's CSF, whereas the CSFs of dyslexic children were 8 to 17 fold lower than a normal adult's CSF seen by comparing original CSFs (orig.) with the CSFs of the practiced observer after 1 practice (1prac.) and 2 or more practice (2prac.) contrast thresholds.

When patterns that test a child's ability to discriminate movement are used to measure the child's CSF, differences between children and adults on the order of 10 times are obtained which was not found previously using long-duration patterns. This same pattern of results was found for each of the 4 test frequencies, as shown in FIGS. 2–5, spanning the range of spatial frequencies that optimally activate magnocellular neurons.

The CSFs of normal and dyslexic children clustered into 2 separate groups. The direction discrimination CSFs revealed a 3- to 4-fold (i.e., 300% to 400%) difference between dyslexics and age-matched normals, whereas orientation discrimination CSFs revealed a 2-fold difference between good and poor readers. This difference between dyslexic and age-matched normal children was significant in both tasks, $p<0.001$ and $p<0.003$, respectively, when analyzed using a Student's t-test for two samples having unequal variance. The much lower CSFs for dyslexic than for age-matched normal readers indicate that a child's direction discrimination CSFs are closely related to their reading ability.

There were no differences between the CSF results of children with reading problems aged 6 to 8 years old and a normal 5-year-old child. In fact, the CSF of a child with reading problems was usually lower than the CSF of a 5-year-old child. Thus, these CSFs show that the development of movement discrimination is still developing in all children, appearing to be arrested in development for dyslexic children.

Previous studies that investigated the detection of brief patterns or velocity discrimination using random dot patterns obtained CSFs that only revealed a 0.3-fold (30%) difference between good and poor readers, instead of the 3- to 4-fold differences in the direction discrimination CSFs that were found in this study. When tasks do not activate movement discrimination channels optimally, then not only are much smaller differences between dyslexic and age-matched normal readers found, but also the difference between dyseidetic and normal readers disappears altogether. When the direction discrimination task was used, there were no significant differences between different types of dyslexic readers, all types having 3 to 4 fold lower CSFs than age-matched normal children. Therefore, this study revealed the importance of mapping out direction discrimination CSFs for a four-octave range of background frequencies centered around test frequencies of 0.25, 0.5, 1, and 2 cycles per degree (cpd) for rapid and effective screening.

Figure 7A:
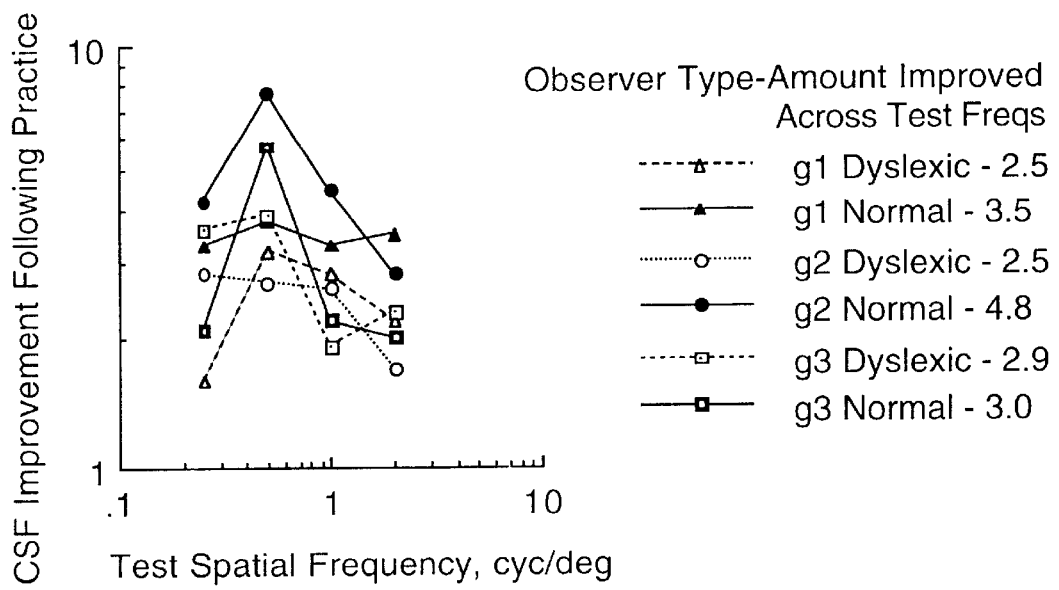
FIGS. 7a–7c are graphical views of data illustrating relationships between an improvement in contrast sensitivity function for direction discrimination with respect to spatial frequency of the test pattern for various subjects.

The direction discrimination CSFs for patterns having a test frequency of 0.25, 0.5, 1, and 2 cpd are ideal to use for dyslexia screening because (1) normal children had the highest CSF, whereas dyslexic children had the lowest CSF, when test and background frequencies were equal, and (2) as the test frequency was increased, the 3-fold differences in the CSFs between dyslexic and normal children increased, as shown in FIG. 7a.

The CSFs for high test and background frequencies when discriminating left-right movement revealed the largest difference between both children and adults, and dyslexic and age-matched normal children. These results demonstrate that the motion networks are still maturing in 5- to 8-year-old children when conducting tasks such as direction discrimination. In addition, this study shows that dyslexics have immature networks, with their CSFs being lower than a practiced normal 5 year old. After five years of age, normal readers have direction discrimination (DD) CSFs that show a peak when the test and background frequencies are equal, whereas children with reading problems show a trough when the test and background frequencies are equal.

The CSFs of normal and dyslexic children reveal a different pattern of results when test and background frequencies were equal, thereby enabling rapid screening for dyslexia at 6 to 7 years old. The spatial frequency combinations that revealed the largest differences between both children and adults and between children with normal reading and children with reading problems were when background frequencies were equal to or greater than the test frequency.

The direction discrimination CSFs revealed a more reliable means to screen for dyslexia. Not only were CSFs for children with reading problems 3 to 4 times lower than age-matched children with normal reading, a different pattern of results for these two groups was found. All dyslexic children had significantly lower CSFs ($p<0.005$) when test and background frequencies were equal, whereas for practiced normal children and normal adults, CSFs were highest when test and background frequencies were equal, as seen across spatial frequencies and at all grade levels and as illustrated in FIGS. 2 to 5, when the child had at least two practice thresholds. This test enabled screening normal from dyslexic children with 100% accuracy, which was confirmed using independent measures from standardized dyslexia tests and teacher and student verbal reports. Only by mapping out the CSFs for test frequencies surrounded by one of a four-octave range of background frequencies, centered about the test frequency, are these uniquely different direction discrimination CSFs found for normal and dyslexic children. The absolute difference in DD-CSFs and the different patterns in DD-CSFs enable rapid and reliable diagnosis of dyslexia, that is, reading difficulty in children who are otherwise normal, in children over 5 years of age.

The Dyslexia Screener (TDS) was used to assess a child's reading ability, since it can be administered in less than 5 minutes and shows high validity (over 85%) for classifying dyslexic children into one of three categories: dyseidetic (spelling problems), dysphonetic (pronunciation problems), and mixed. However, the TDS cannot be administered until the child is in the second grade, as it relies on the child's ability to decode words (identify by naming) and encode words (spell eidetically and phonetically). The TDS also measures the child's reading grade level.

During this study we discovered that normal and dyslexic readers displayed a different pattern of results, with these differences enabling dyslexic children in first grade to be identified after two practice thresholds. By the end of the first grade, this diagnosis was confirmed using the TDS. Based on the TDS and the direction discrimination CSFs, children were divided into two groups at the end of this study: those who had normal visual function and those who had dyslexia The TDS revealed that the 10 dyslexic children in grades 2 and 3 fell into approximately equal proportions into each of the three subtypes, consisting of four dyseidetic, two dysphonetic, and four mixed. As there were no significant differences between the CSFs of these three subtypes of dyslexia, the data from all dyslexic children at each grade level were grouped together.

Exemplary test window 134 was configured as a fish, and the computer 102 was configured to present a "fish game" to children in which the repeated asking of whether the fish moved to the right or to the left was carried out. Repetition of displaying the background and the test pattern at different contrasts and spatial frequencies to children (i.e., practicing the fish game) causes CSFs for direction discrimination to rise in all children, including those who read normally and those with reading difficulty. Children of different ages require different amounts of practice.

Figure 3A:
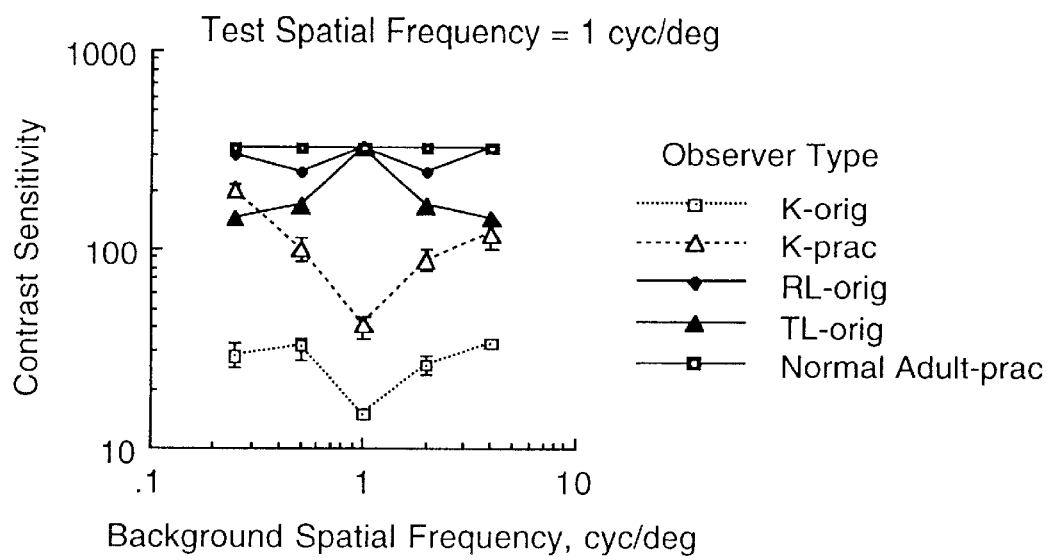
FIGS. 3a–3f are graphical views of data illustrating relationships between contrast sensitivity for direction discrimination with respect to spatial frequencies of the background for various subjects, including dyslexic and normal children, particularly illustrating the relationship at a spatial frequency of 1.0 cycle per degree of the test pattern.
Figure 3B:
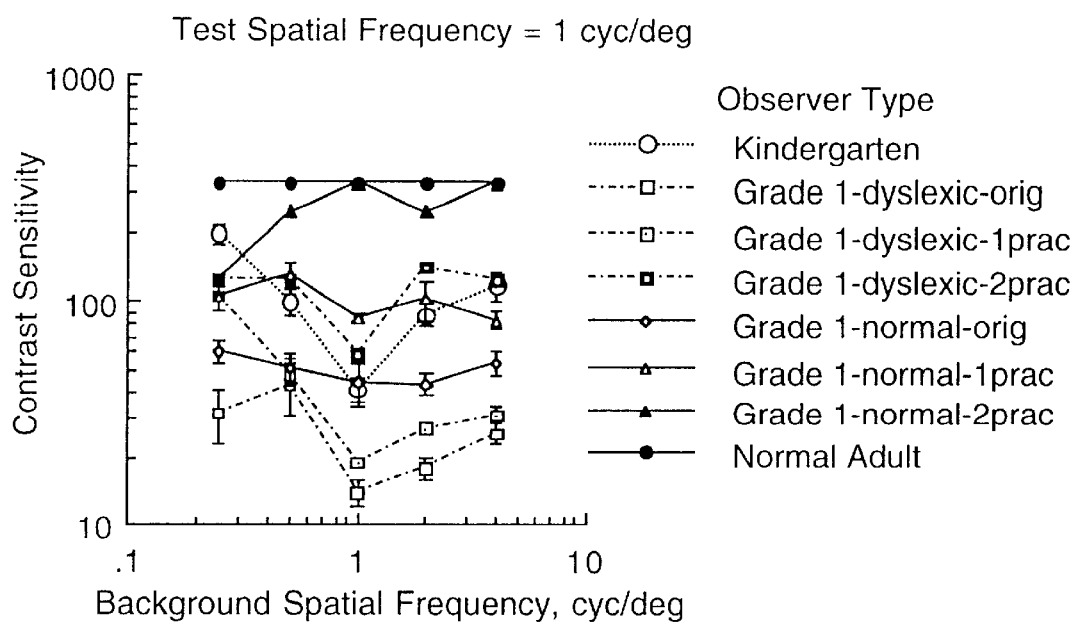
Figure 3C:
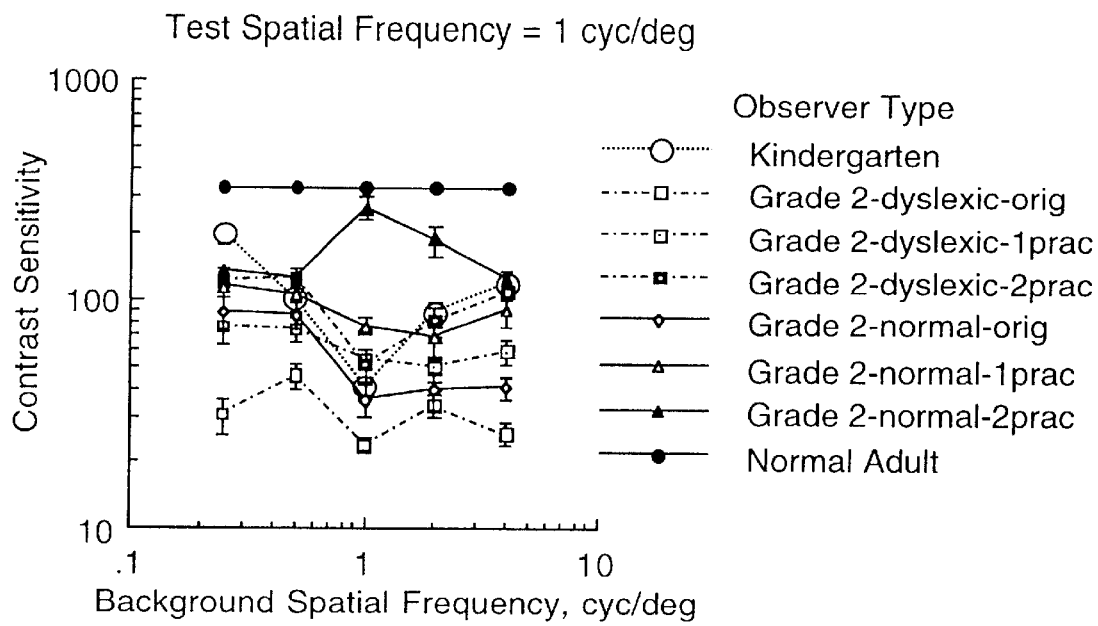
Figure 3D:
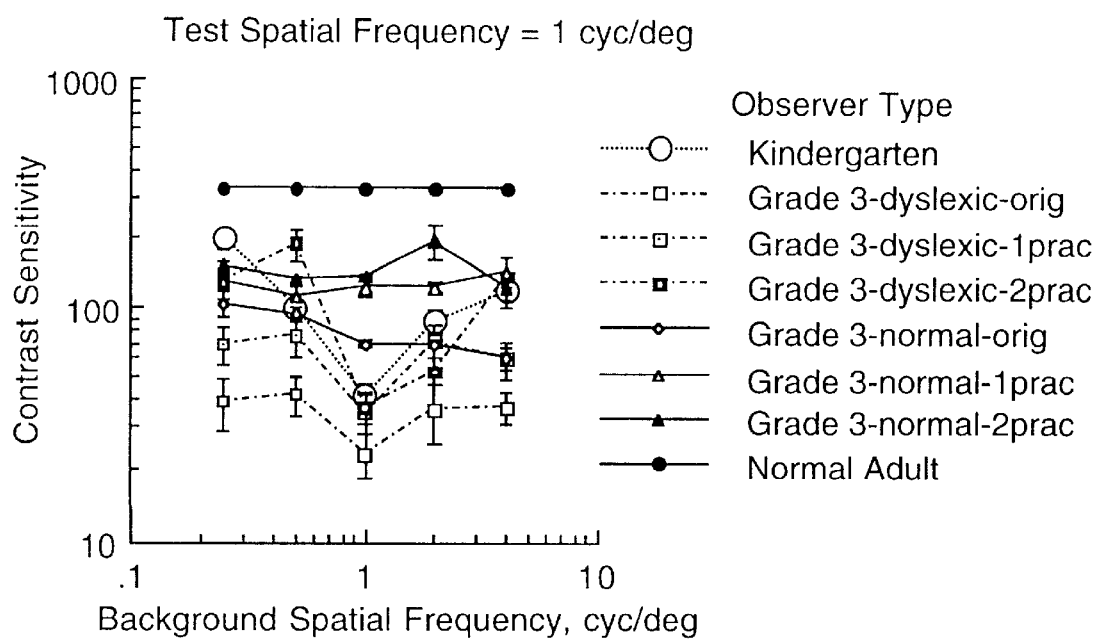
Figure 3E:
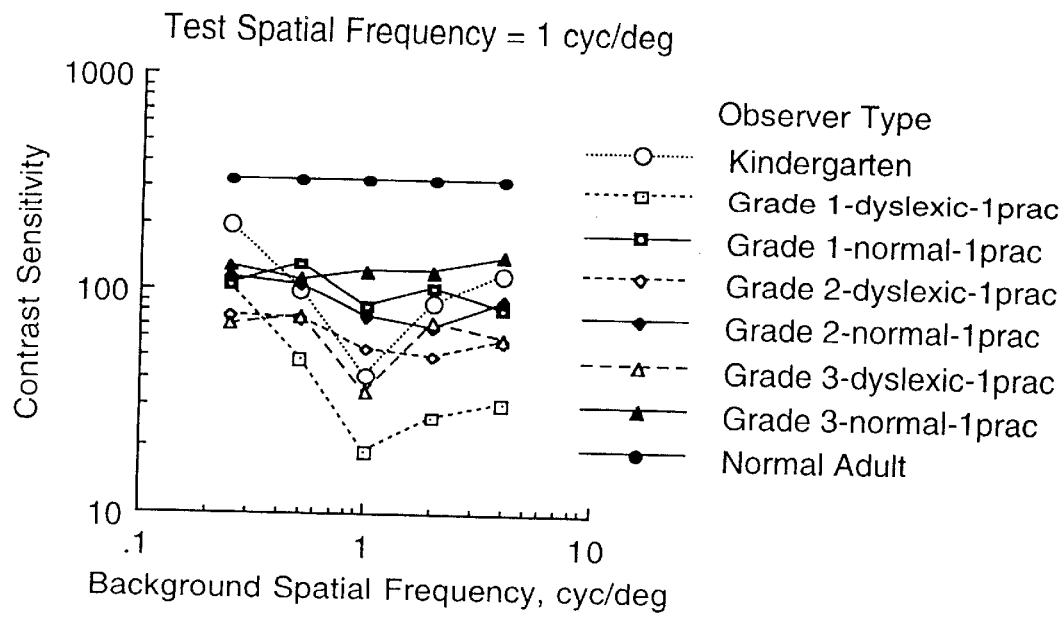
Figure 3F:
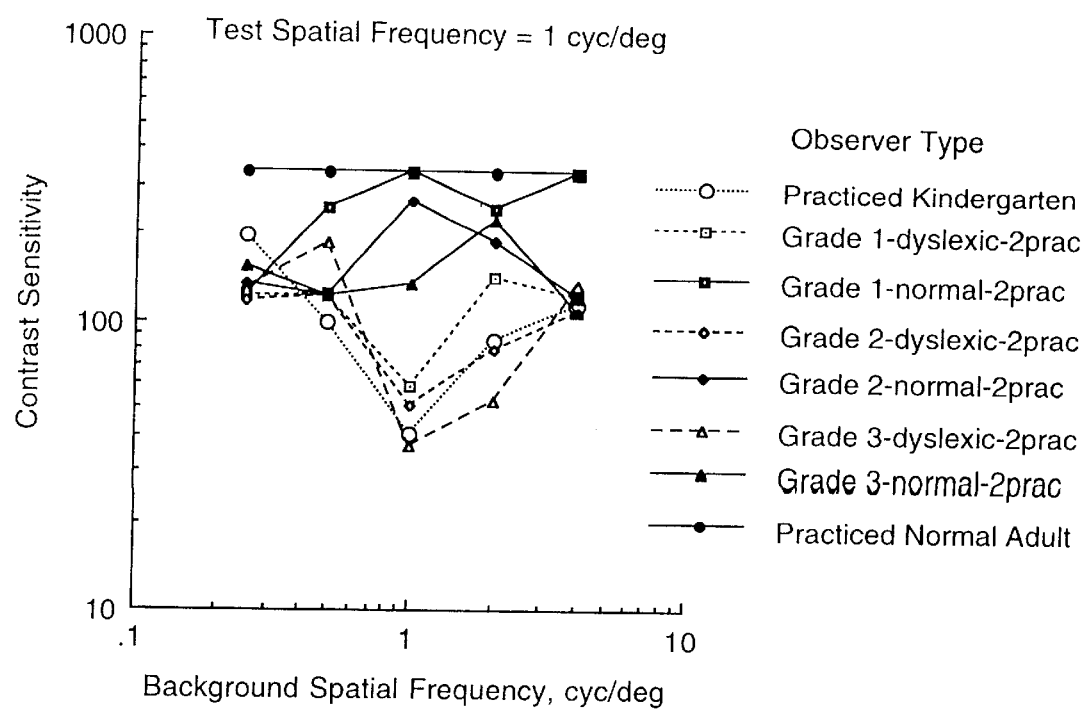
Figure 4A:
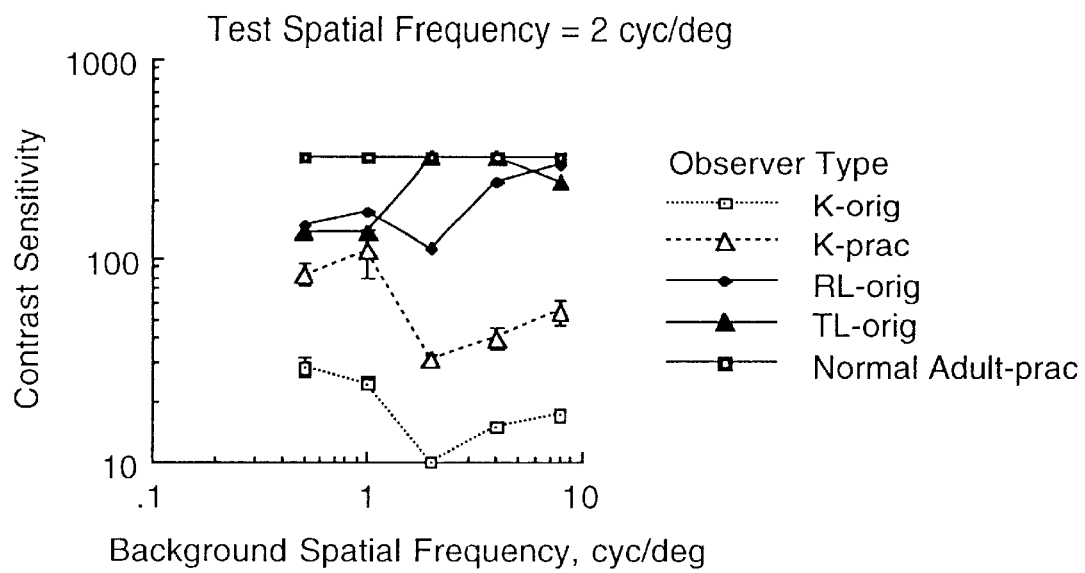
FIGS. 4a–4f are graphical views of data illustrating relationships between contrast sensitivity for direction discrimination with respect to spatial frequencies of the background for various subjects, including dyslexic and normal children, particularly illustrating the relationship at a spatial frequency of 2.0 cycles per degree of the test pattern.
Figure 4B:
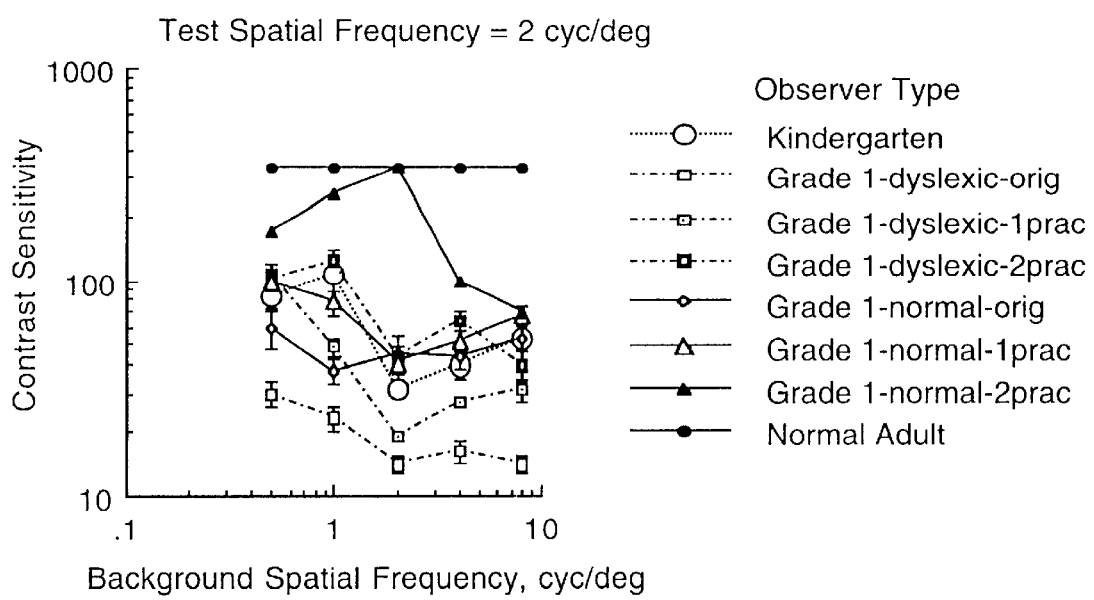
Figure 4C:
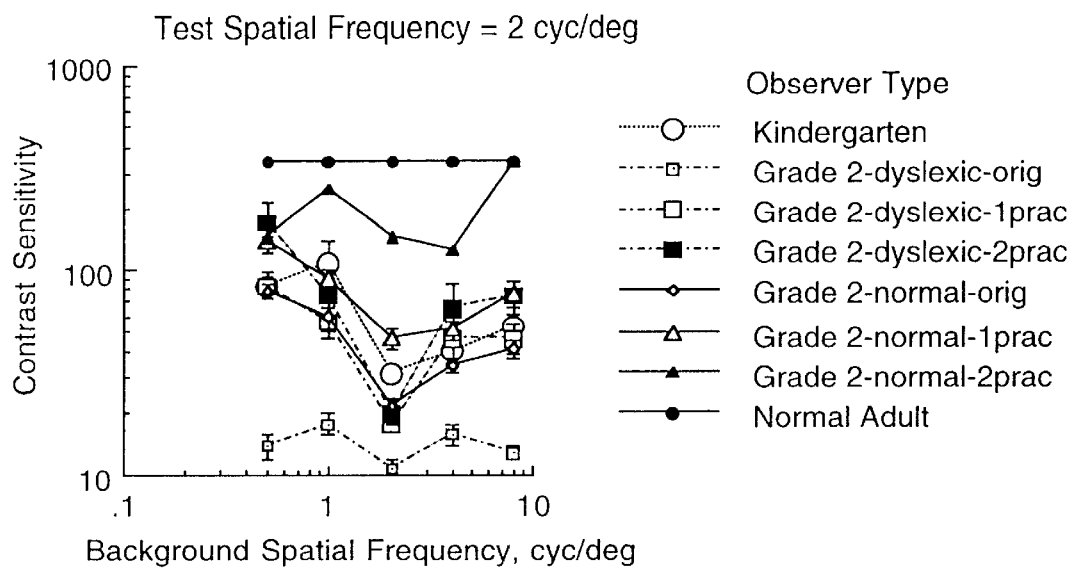
Figure 4D:
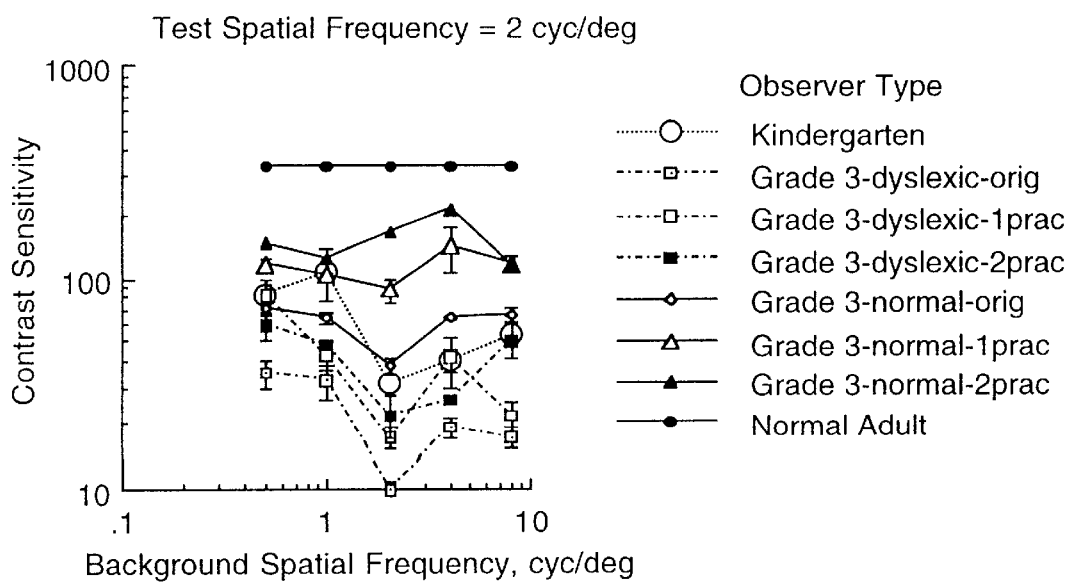
Figure 4E:
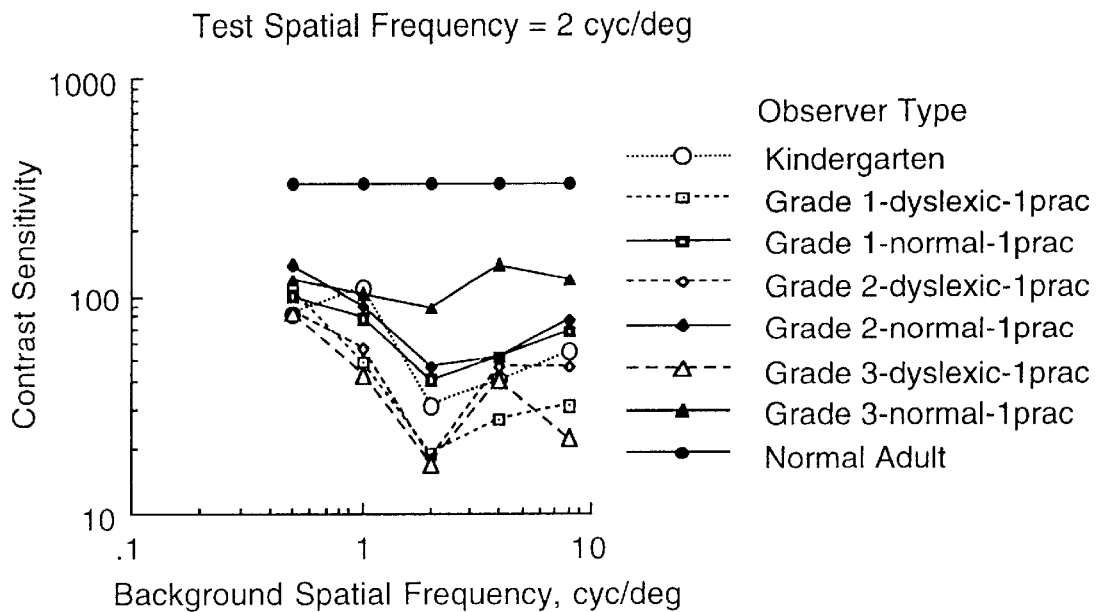
Figure 4F:
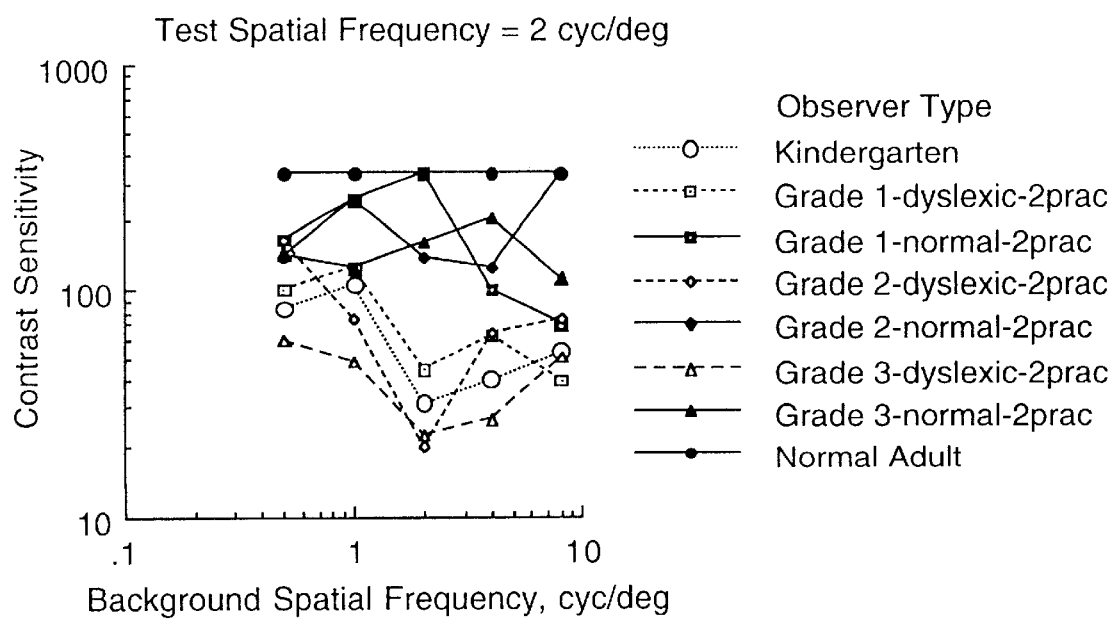
Figure 7B:
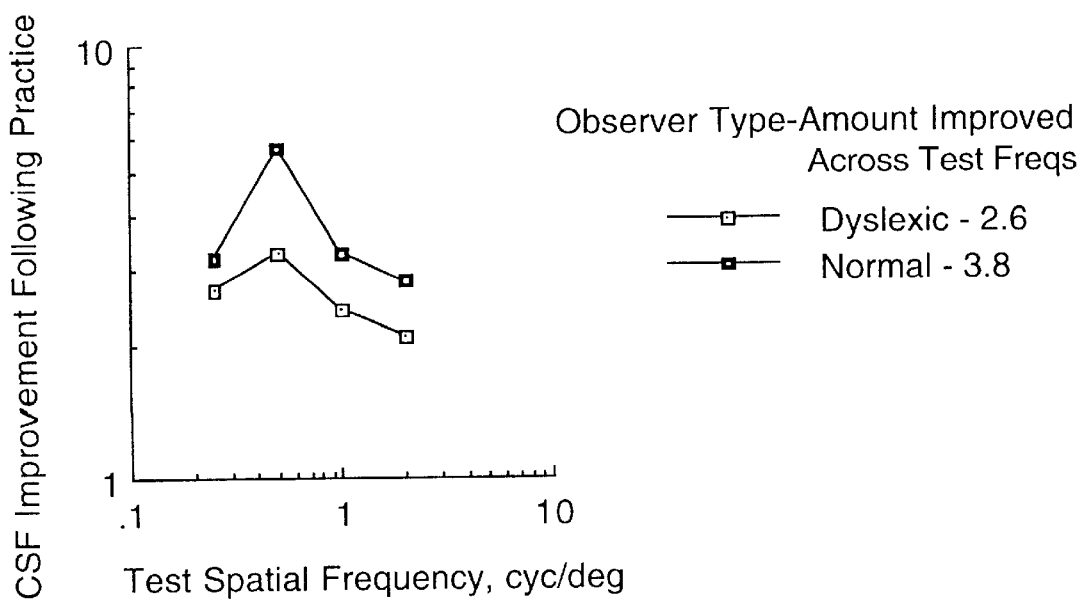
Figure 11A:
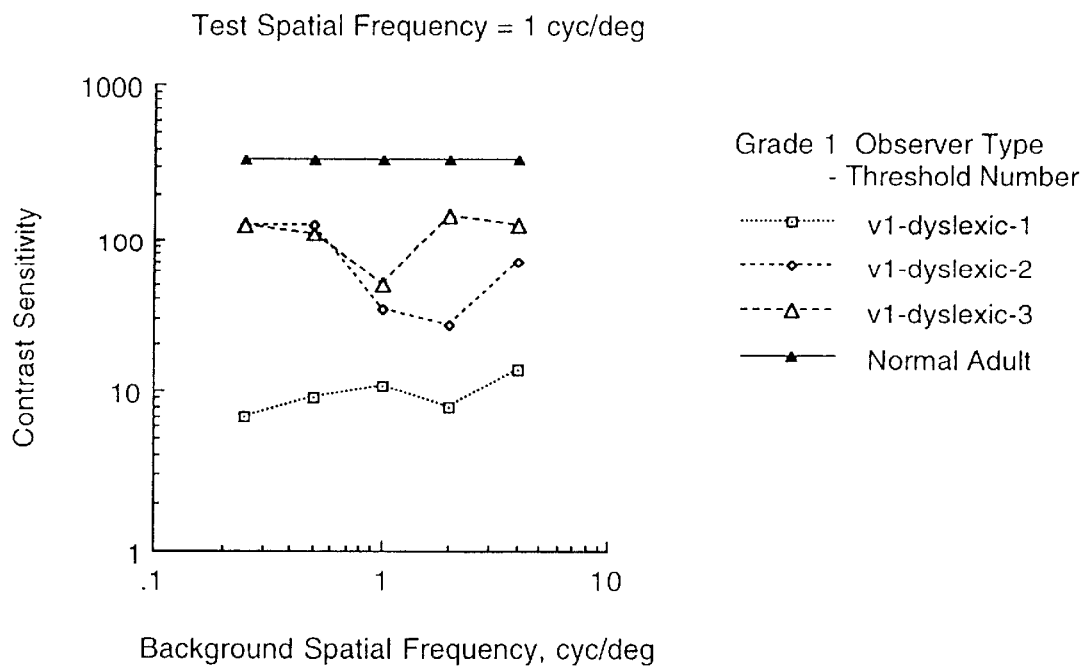
FIGS. 11a–11c are graphical views of data illustrating relationships between contrast sensitivity with respect to background spatial frequency for a test-pattern spatial frequency of 1.0 cycle per degree for various subjects in Grade 1.
Figure 11B:
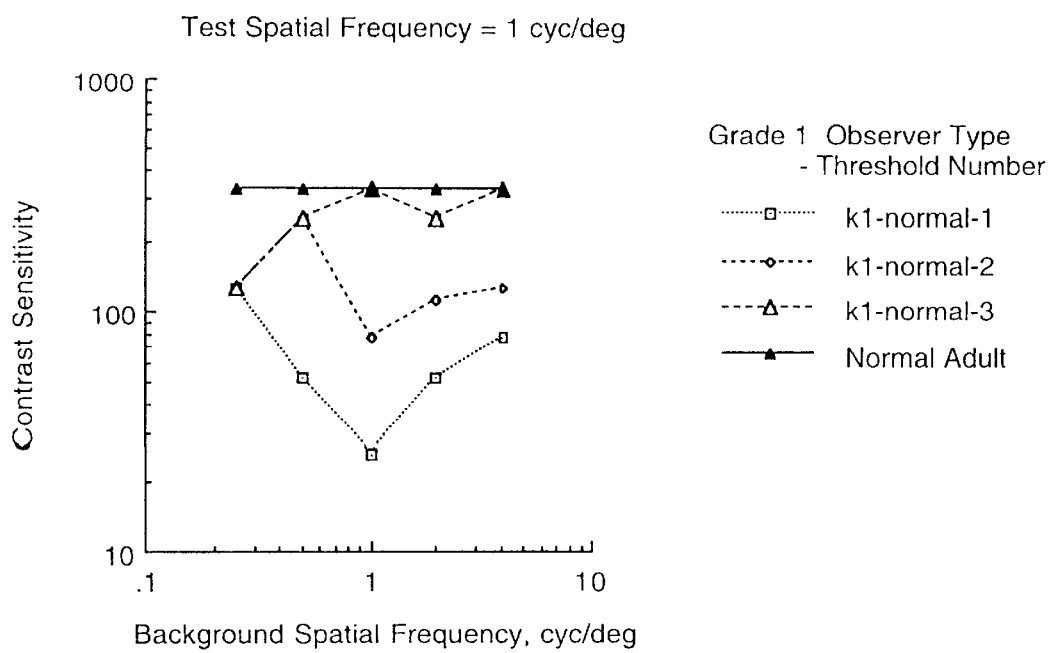
Figure 11C:
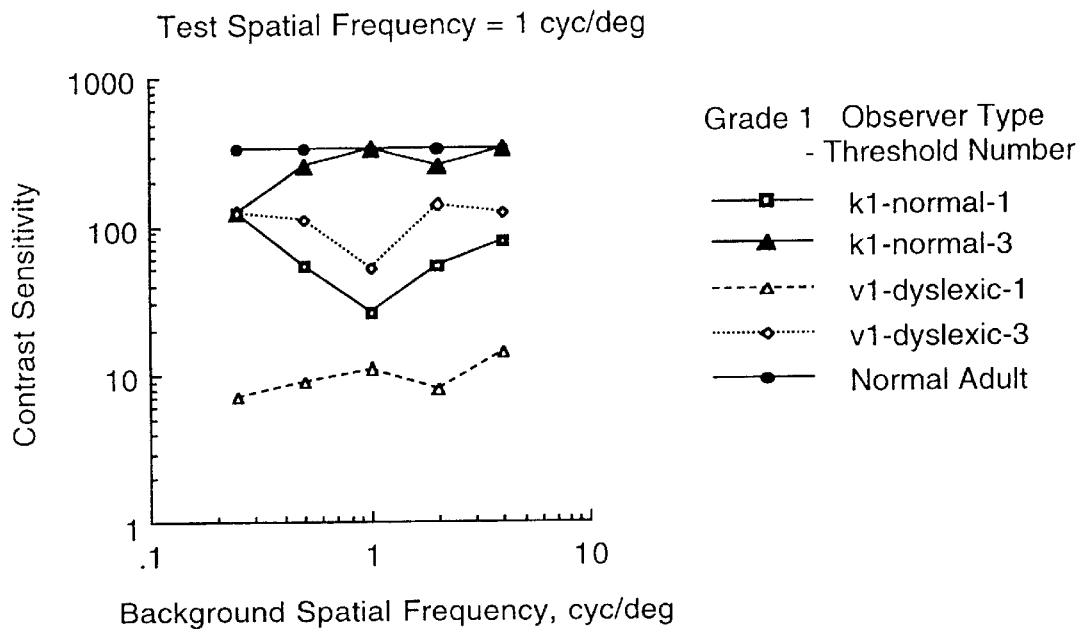

The greatest improvements when discriminating between test frequencies of 1 cpd and 2 cpd were obtained for a first-grade normal reader after two practice thresholds, as shown in FIGS. 3f, 4f, and 11c, whereas the child in the third grade shows the least amount of improvement for these test frequencies, as shown in FIGS. 3f, 4f, 7a, and 13b–e. This indicates that the child aged 6 to 7 years old is in a critical period where the plasticity of the neural channels can be modified more easily by visual experience than is found for the child who is 8 years old. Practice on each of 20 different combinations of test-pattern and background frequencies improved direction discrimination CSFs 3 to 4 fold, as shown in FIG. 7b. Practice one time on each pattern was significant (p<0.0001) in improving the child's direction discrimination CSFs, providing rapid remediation. This can be seen by comparing the original (orig.) and practiced, either following one practice threshold (1prac) or two practice thresholds (2prac) shown in FIGS. 2–5b, c, and d for normal and dyslexic children at each test frequency and grade level. The earliest and largest improvements in a child's CSF occur when test and background frequencies are equal, suggesting that visual processing takes place within single, visual cortical, spatial frequency channels (e.g., 0.5 cpd in the test and 0.5 cpd in the background), rather than within combinations of different spatial frequency channels (e.g., 0.5 cpd in the test and 2 cpd in the background, and improve the most with practice.

This study found that remediation was most rapid when the child was setting up the neural networks that enable text to be decoded and encoded, and at around 6 to 7 years old. The largest improvements in a child's CSF occurred when test and background frequencies were equal, as shown in FIGS. 2–5b,c, and d, suggesting that changes within a single spatial frequency channel improved the most with practice, rather than within combinations of different spatial frequency channels.

The CSFs for a normal first and second grader who completed two or more practice thresholds (2prac) equaled the normal adult's CSF when test and background frequencies were equal, as shown in FIGS. 2f, 3f, 4f, 8c, 9d and e, 11c, and 12c. On the other hand, as the test frequency increased from 0.5 cpd to 2 cpd, a child in grade 3, both normal and dyslexic, showed the least amount of improvement after two practice thresholds, as shown in FIGS. 2f, 3f, 4f, and 13a. Moreover, the highest average increase in a normal child's CSF following one practice threshold was found for children in the second grade as shown in FIG. 7b, improving from 3 to 8 fold with an average of 5 fold across frequencies, whereas normal first graders improved an average of 4 fold and third graders an average of 3 fold across spatial frequencies. Therefore, remediation was most rapid for the 6- to 7-year-old child.

The rapid increase in the child's CSF with only 2 practice thresholds in first grade, and the over two fold lower CSFs for practiced normal observers in third grade indicates that the ability to discriminate left-right movement is in a critical period when the child is 6 to 7 years old, enabling rapid remediation with only two practice thresholds. This can be seen more clearly by examining the individual data in FIGS. 8 to 13, where the CSFs on individual sessions are plotted. The individual graphs of a large subset of both dyslexic and age-matched normals following practice at each grade level for test frequencies of 0.5 cpd and 1 cpd are plotted in FIGS. 8a to 13a.

When the test frequency was 0.5 cpd as shown in FIGS. 2a–e, 8a–d, 9a–g, and 10a–e, then:

(1) following one practice threshold (shown in FIG. 2e), there was a progressive increase in the child's direction discrimination CSFs as the child advanced from grade 1 to grade 3;

(2) following two practice thresholds (shown in FIGS. 2f, 8b–d, 9c–g, and 10b–e), normal children in grades 1 to 3 always had the highest CSF, whereas dyslexic children had the lowest CSF, when test and background frequencies were equal, i.e., the CSFs for dyslexic and normal age-matched children were tightly coupled into two different groups; and (3) the largest improvement in direction discrimination CSFs following practice, from 3 to 8 fold, occurred for both normal and dyslexic children at all grade levels (shown in FIGS. 7a and b).

This improvement in the CSF following practice decreased as the test spatial frequency was increased, as shown in FIGS. 7a and b. These results indicate that 0.5-cpd test frequencies activate the mechanism used for left-right movement discrimination in the center of its working range. Moreover, students reported that they found the task easiest when discriminating left-right movement of 0.5-cpd and 1-cpd test patterns.

Figure 12A:
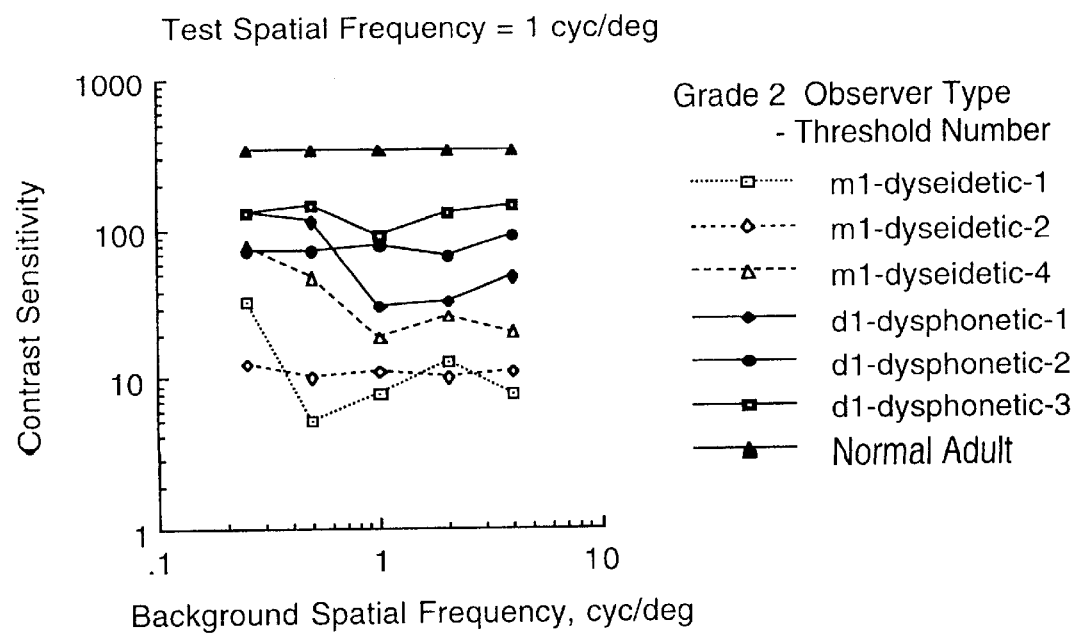
Figure 12B:
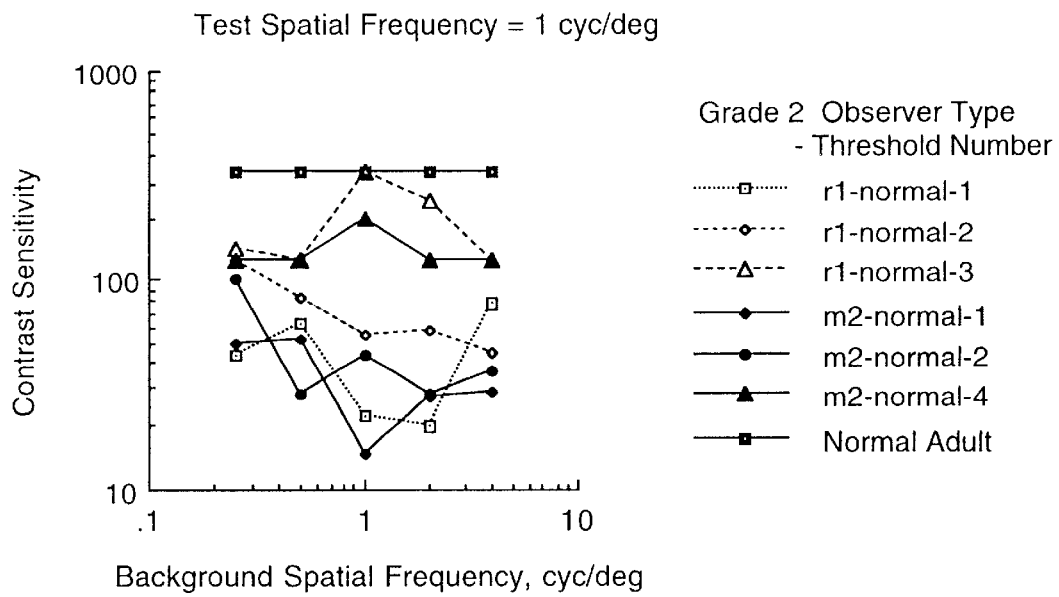
Figure 13A:
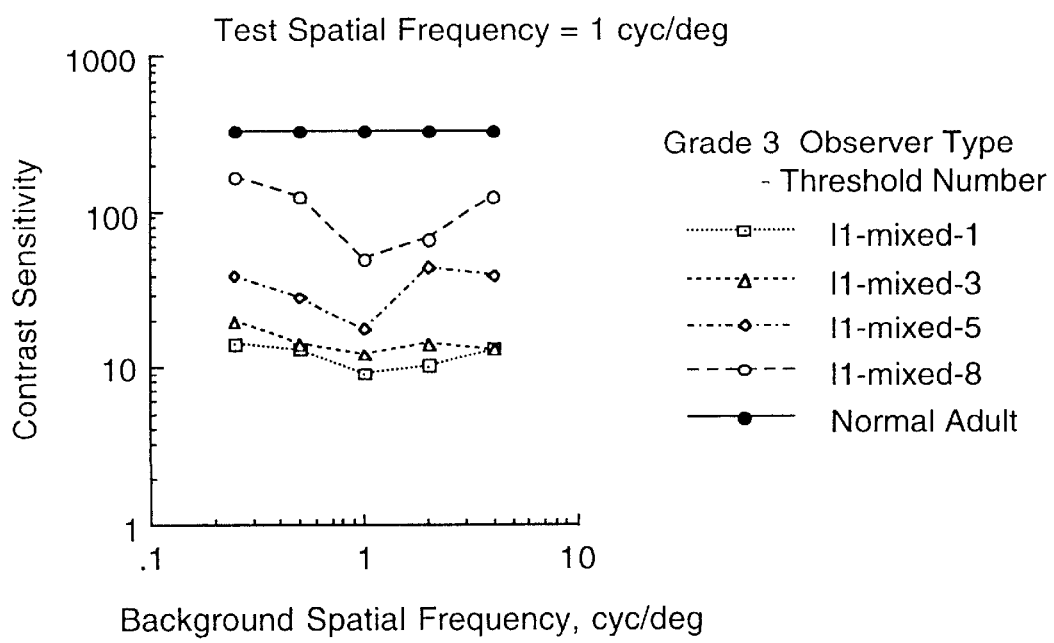
FIGS. 13a–13c are graphical views of data illustrating relationships between contrast sensitivity with respect to background spatial frequency for a test-pattern spatial frequency of 1.0 cycle per degree for various subjects in Grade 3.
Figure 13B:
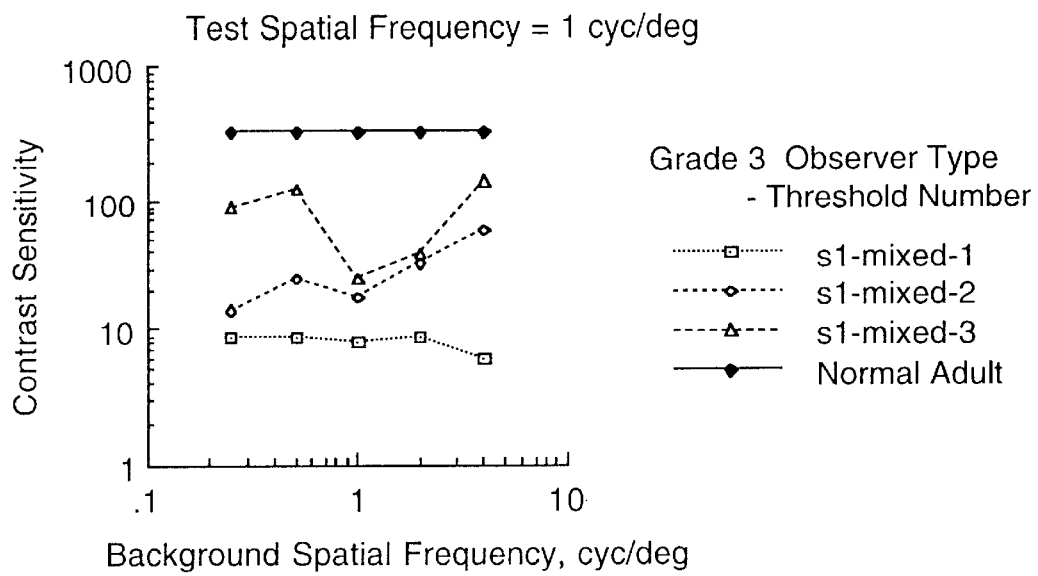
Figure 13C:
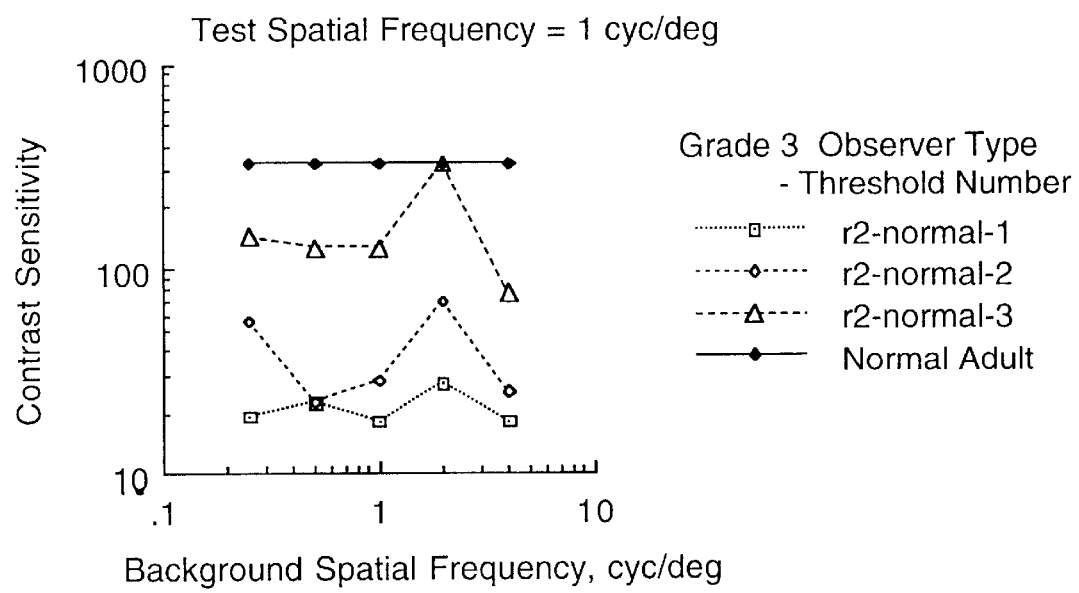

The individual graphs when discriminating the direction 1-cpd test gratings moved are presented in FIGS. 11 to 13. It can be seen that both dyslexic and normal third graders showed less improvement overall (shown in FIGS. 13a–e) when discriminating left-right movement of 1-cpd test gratings, as opposed to a 0.5-cpd test pattern (shown in FIGS. 10a–e). The smaller effects of remediation at 1 cpd across grade levels is shown in FIG. 7a. Moreover, both dyslexic (shown in FIGS. 11b and d) and normal (shown in FIG. 11c and d) first graders have much higher CSFs following two practice thresholds than do third graders (shown in FIG. 3f). The CSFs of 7-year-old students following two practice thresholds (shown in FIGS. 3f and 12b–d) are lower than the CSFs of 6 year olds and higher than the CSFs of 8 year olds. These data provide more support that remediation is most rapid when the child is 6 to 7 years old, demonstrating that the neural channels are more able to be modified by visual experience at 6 to 7 years old.

Figure 7C:
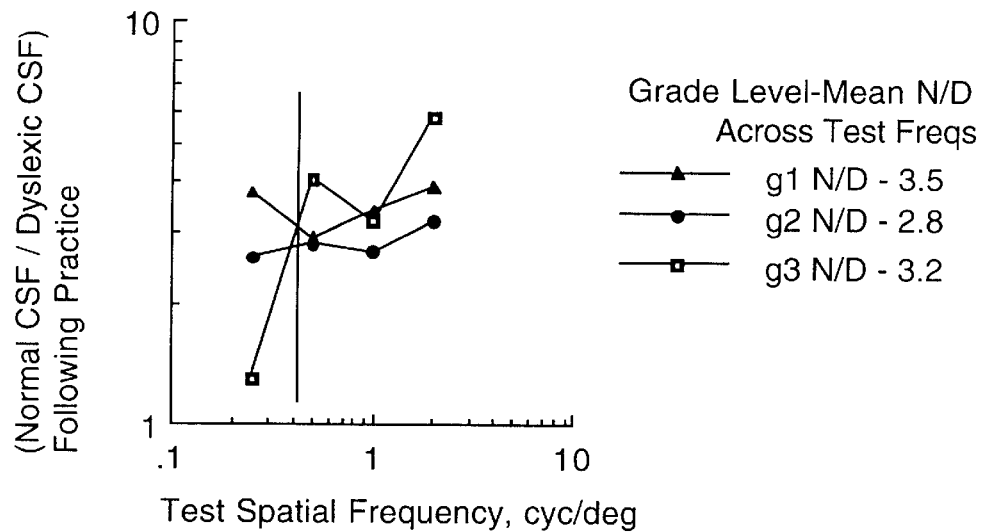
Figure 8A:
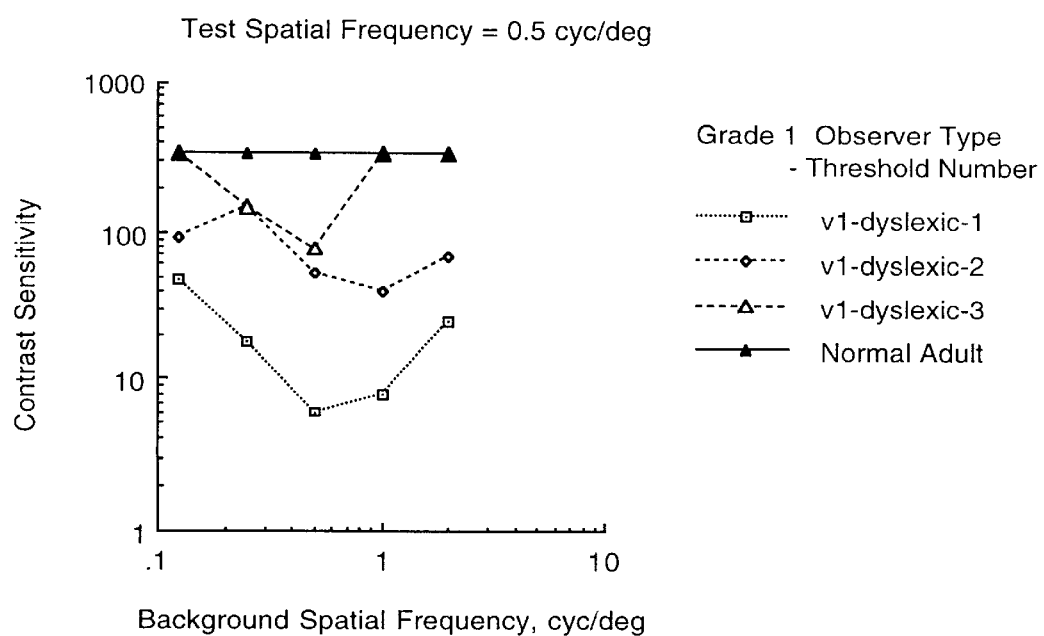
FIGS. 8a–8c are graphical views of data illustrating relationships between contrast sensitivity with respect to background spatial frequency for a test-pattern spatial frequency of 0.5 cycle per degree for various subjects in Grade 1.
Figure 8B:
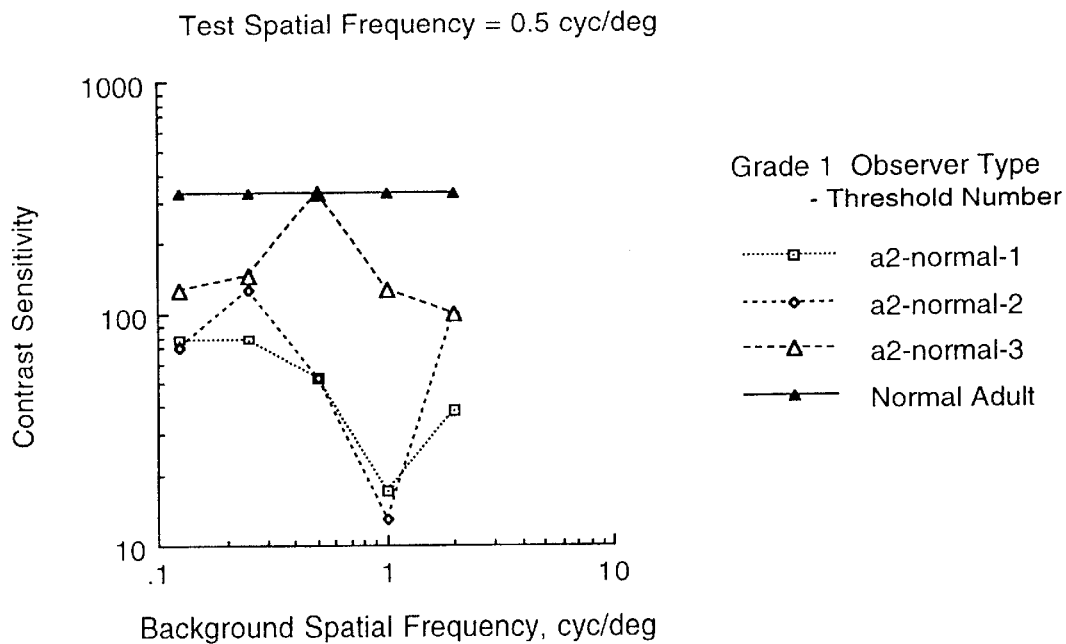
Figure 8C:
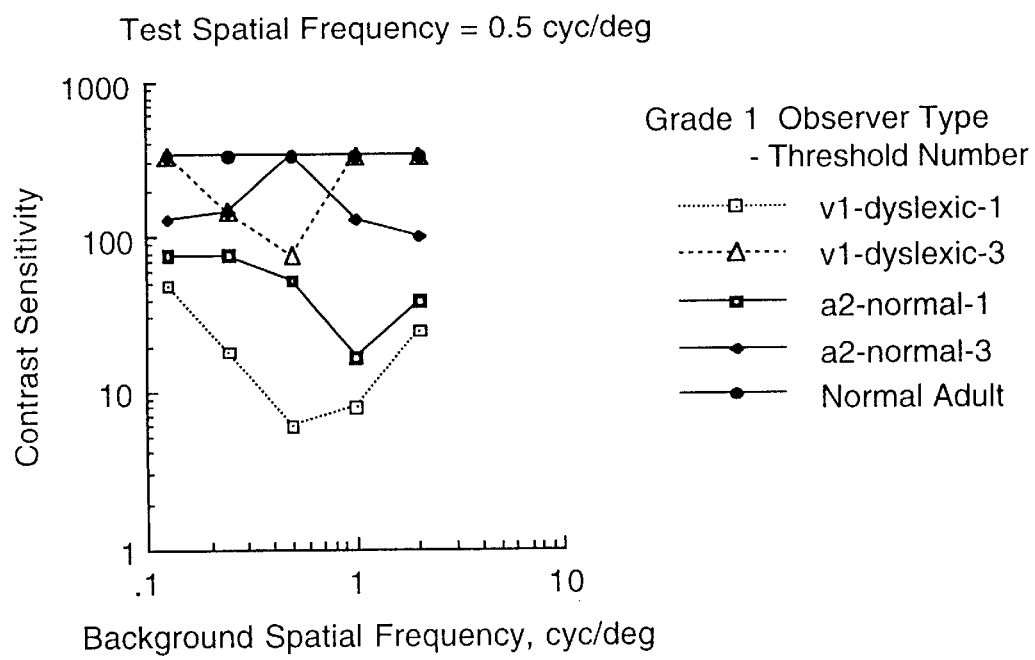
Figure 9A:
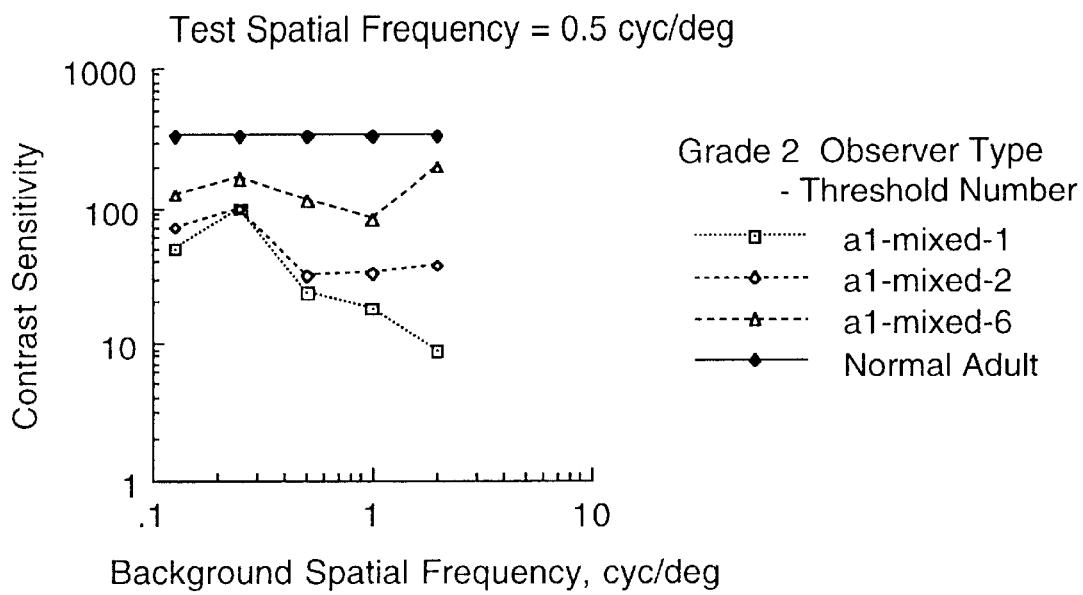
FIGS. 9a–9c are graphical views of data illustrating relationships between contrast sensitivity with respect to background spatial frequency for a test-pattern spatial frequency of 0.5 cycle per degree for various subjects in Grade 2.
Figure 9B:
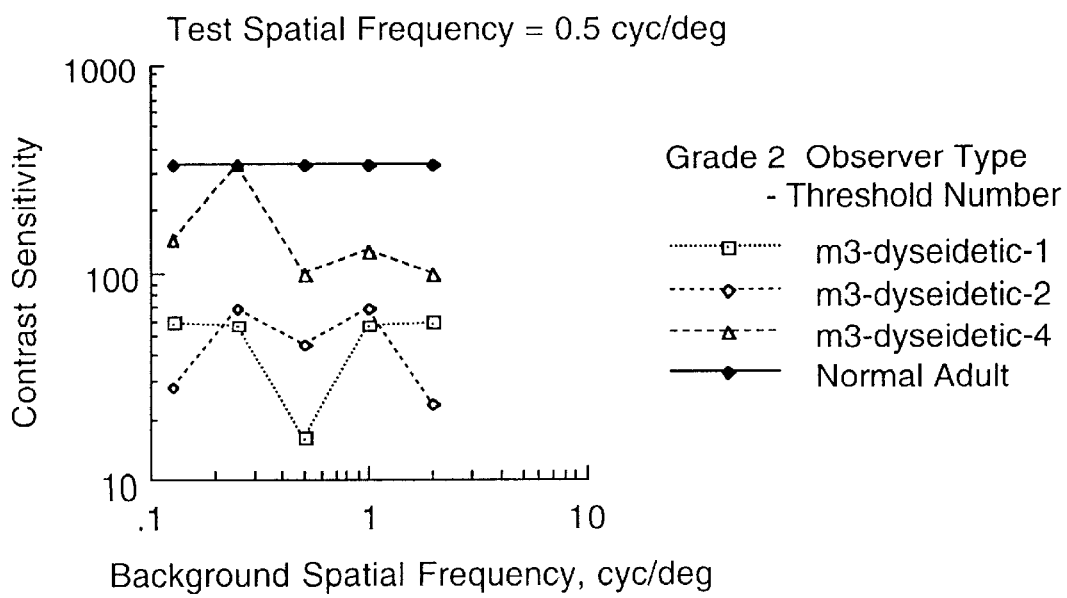
Figure 9C:
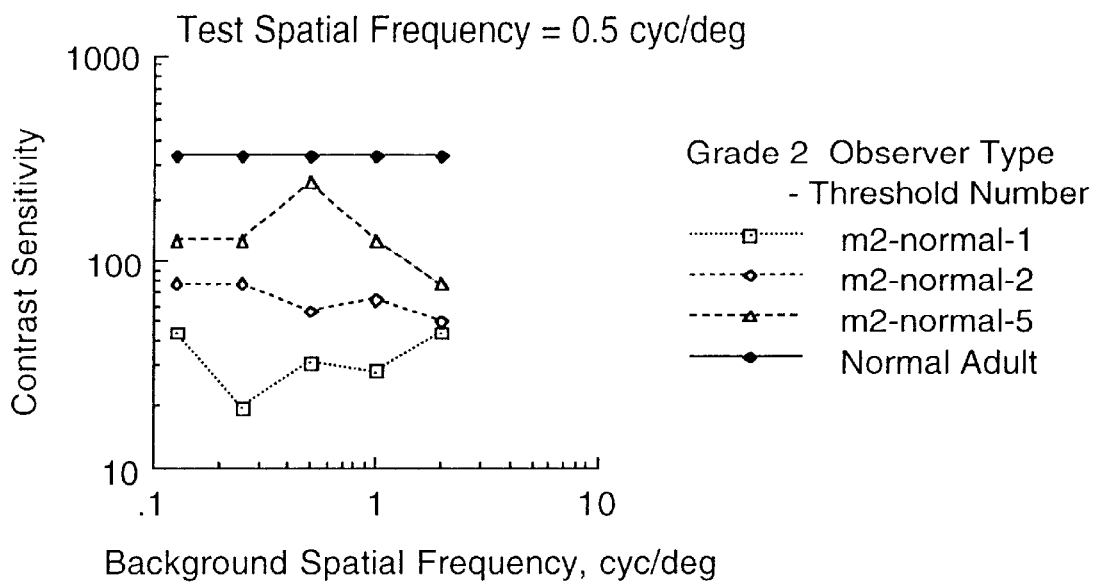
Figure 10A:
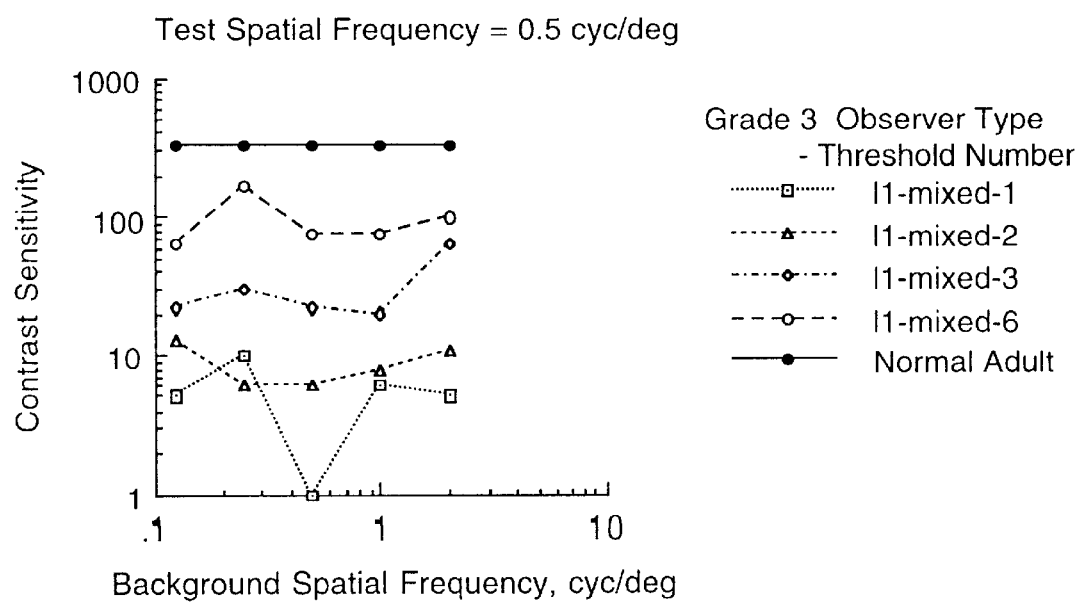
FIGS. 10a–10c are graphical views of data illustrating relationships between contrast sensitivity with respect to background spatial frequency for a test-pattern spatial frequency of 0.5 cycle per degree for various subjects in Grade 3.
Figure 10B:
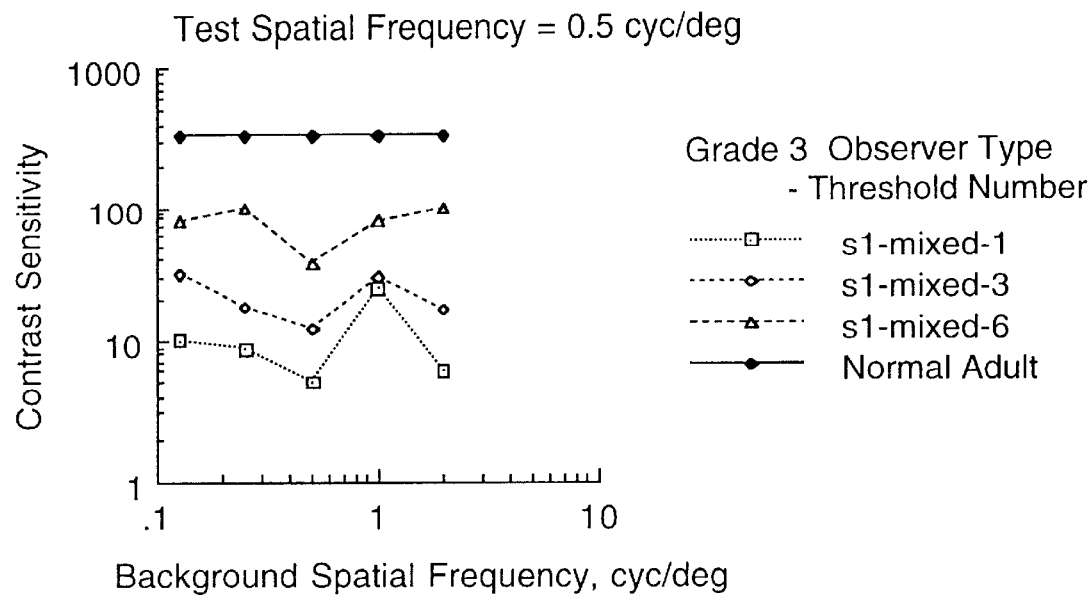
Figure 10C:
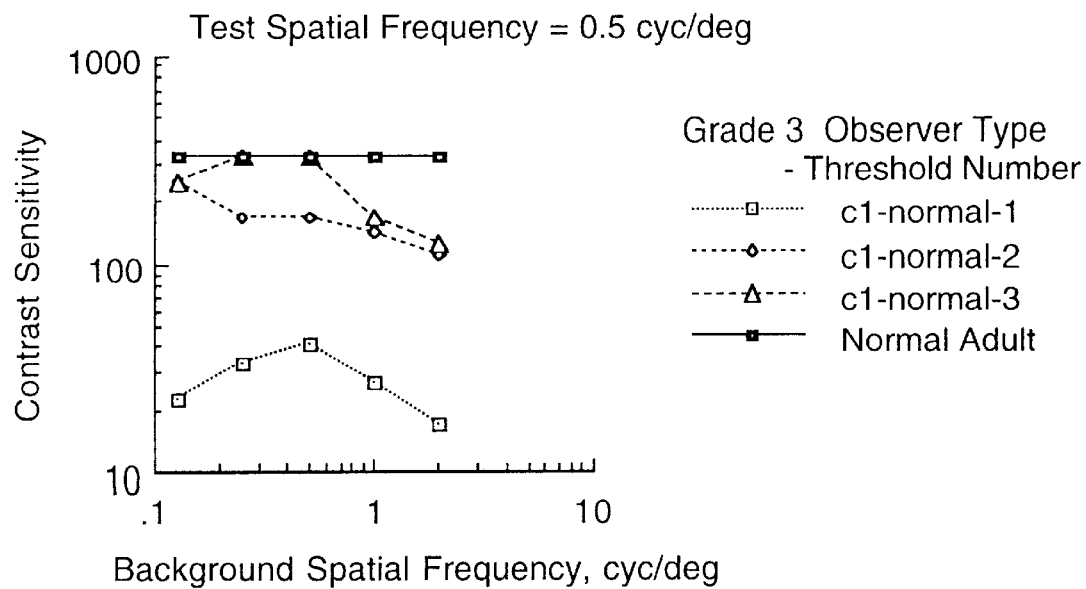

At high test frequencies of 2 cpd, all children reported that the task was more difficult, because of the small lateral movement of the test pattern (about 5 pixels to the left or right relative to the background pattern). The children all reported that they found this task easiest when fixating on the round "nose" of the fish to discriminate left-right movement It was at this high test frequency that the largest differences between normal and dyslexic children (shown in FIG. 7c) were found at all grade levels and frequency combinations (shown in FIG. 4). However, the smallest improvements following one practice threshold on each frequency combination were found when the test frequency was 2 cpd (shown in FIGS. 7a and b).

Figure 5A:
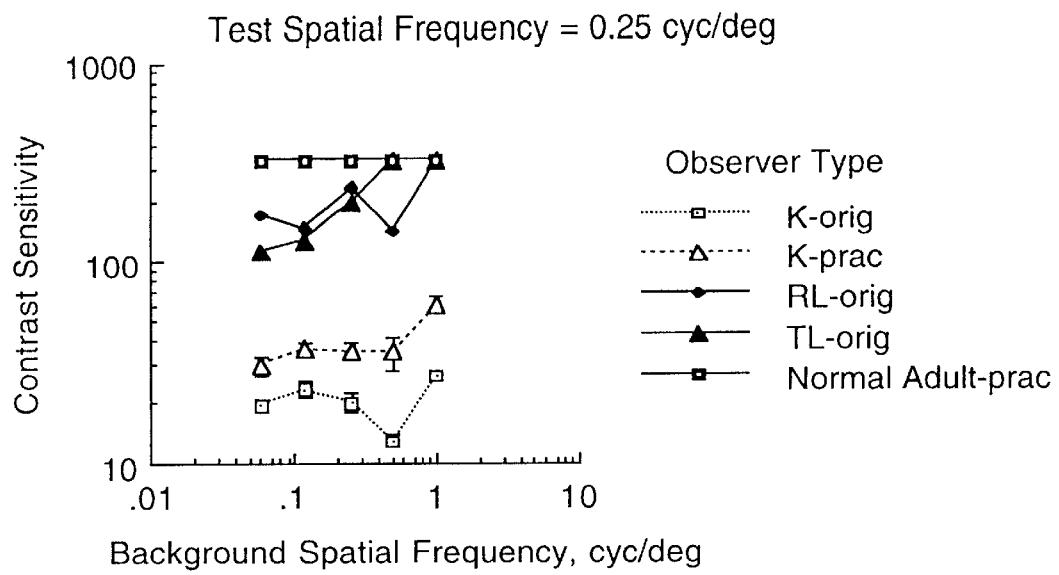
FIGS. 5a–5f are graphical views of data illustrating relationships between contrast sensitivity for direction discrimination with respect to spatial frequencies of the background for various subjects, including dyslexic and normal children, particularly illustrating the relationship at a spatial frequency of 0.25 cycle per degree of the test pattern.
Figure 5B:
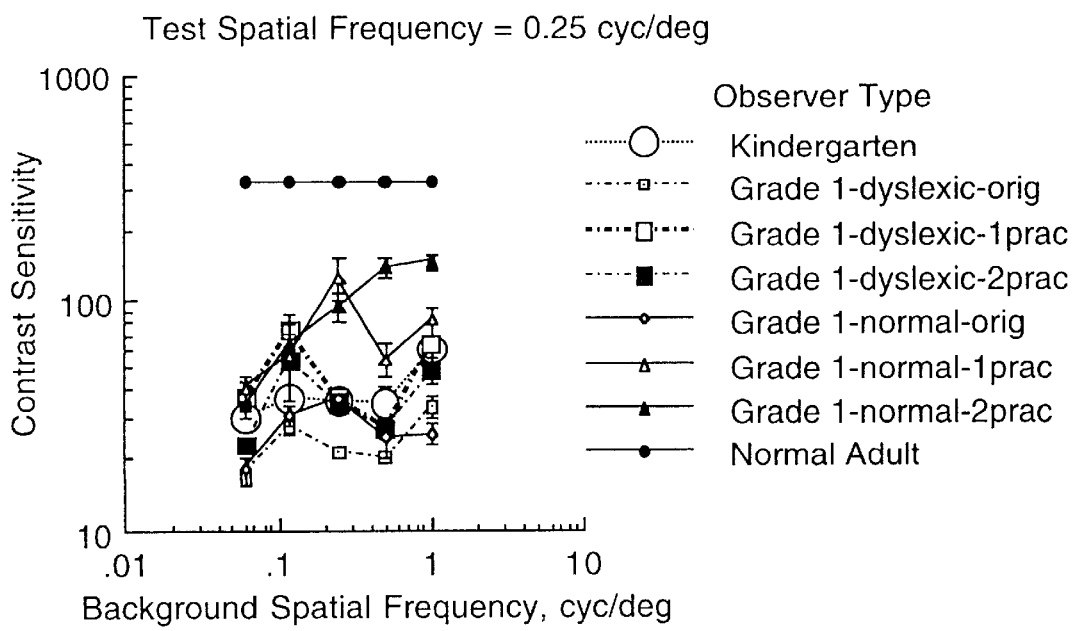
Figure 5C:
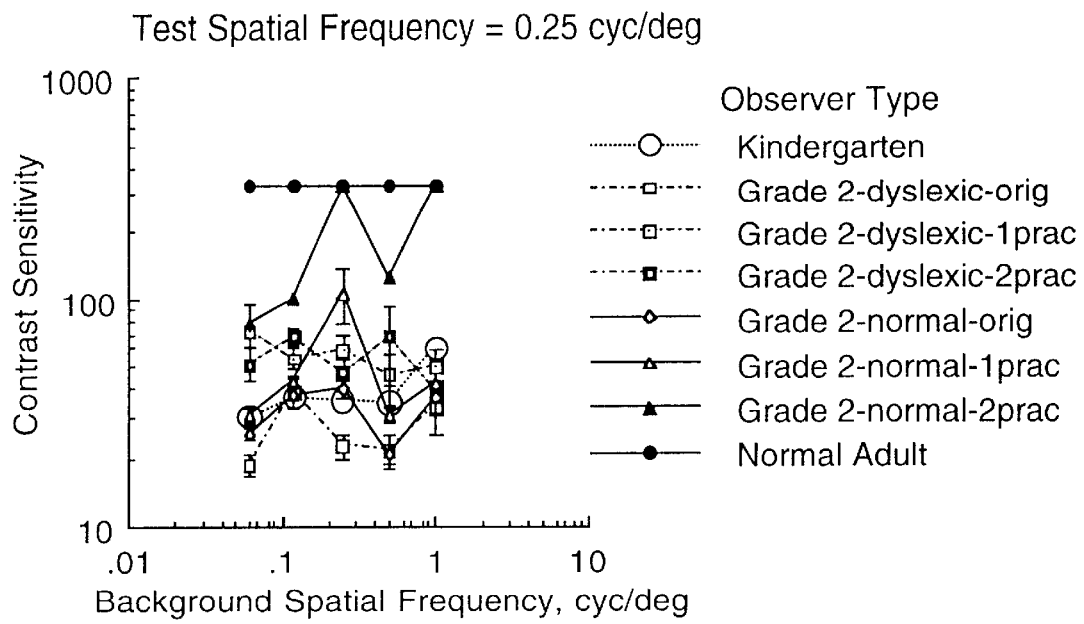
Figure 5D:
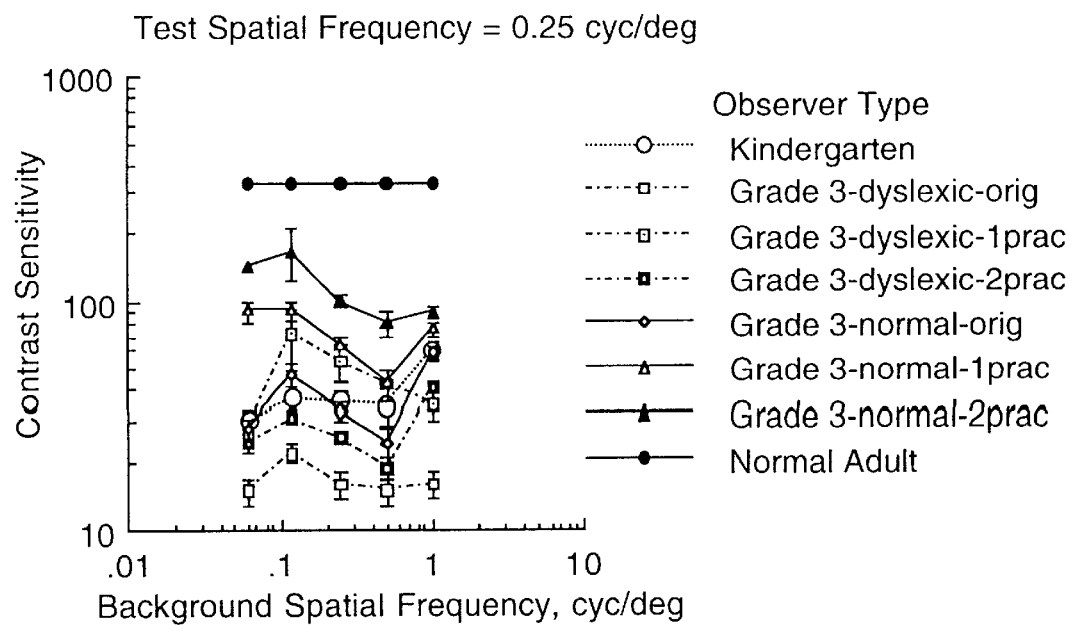
Figure 5E:
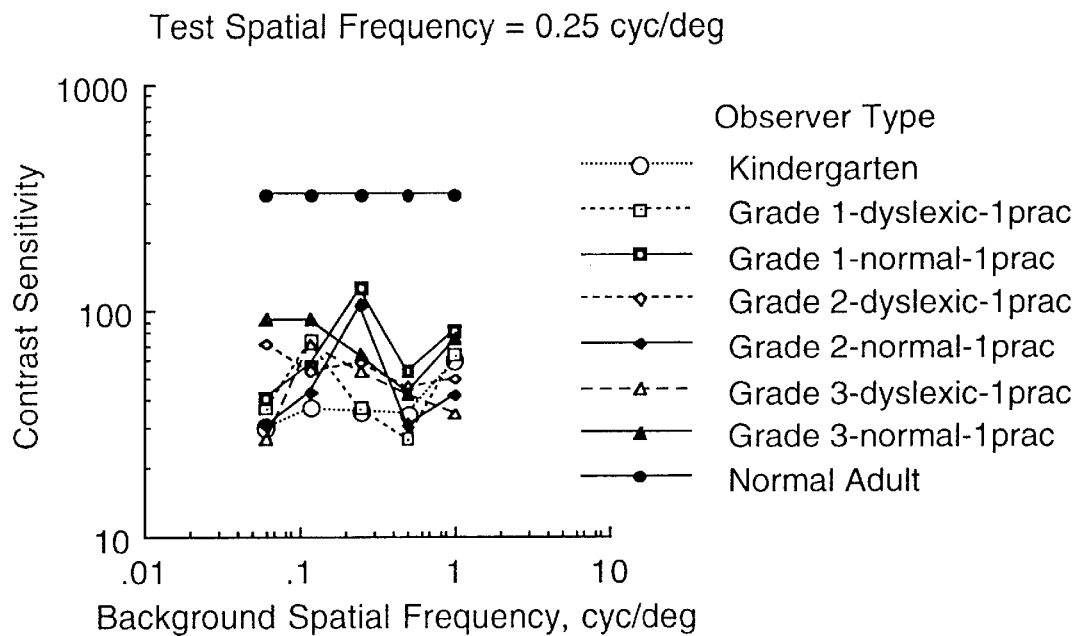
Figure 5F:
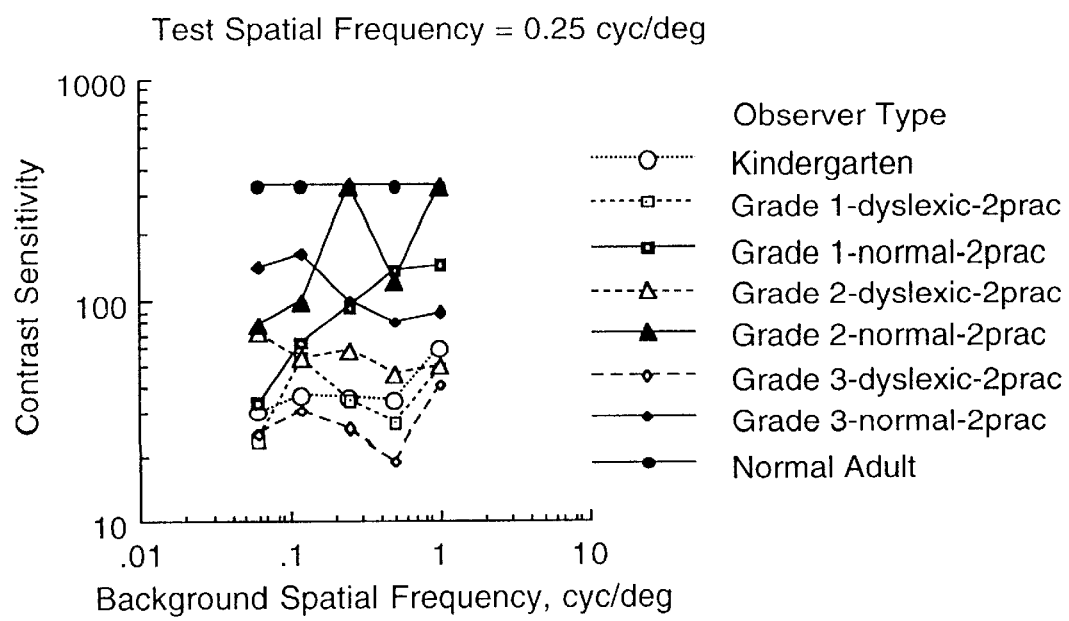
Figure 6A:
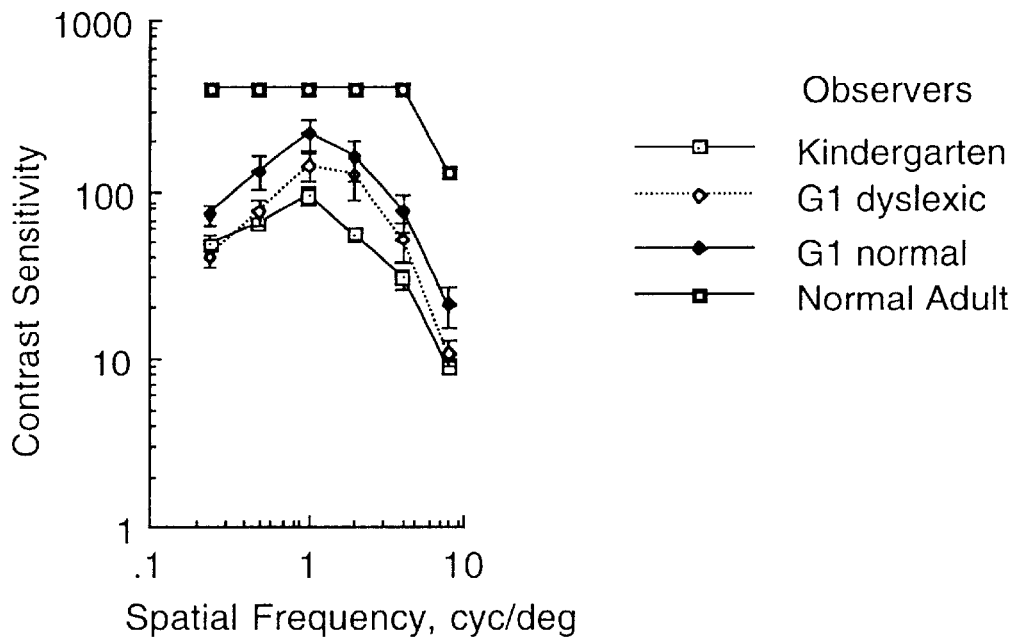
FIGS. 6a–6d are graphical views of data illustrating relationships between contrast sensitivity for orientation discrimination with respect to spatial frequency of the test pattern for various subjects.
Figure 6B:
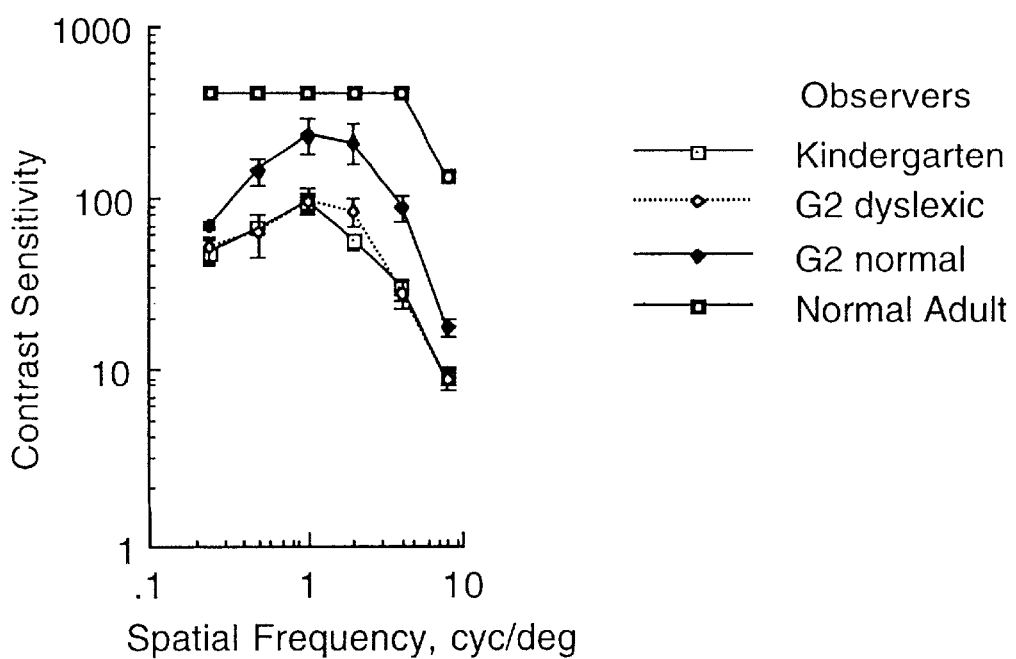
Figure 6C:
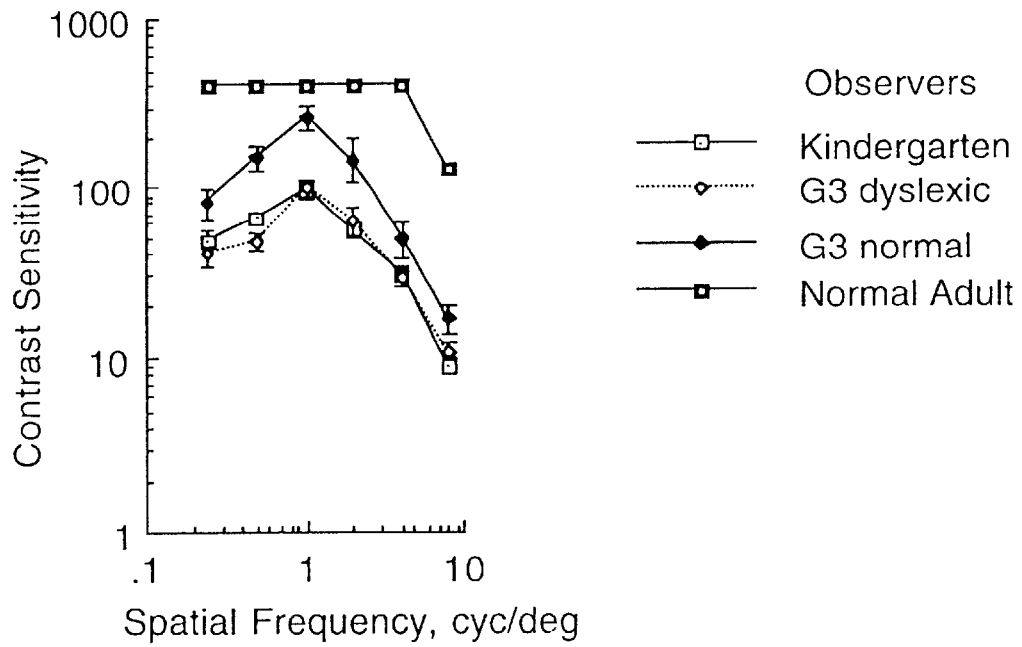
Figure 6D:
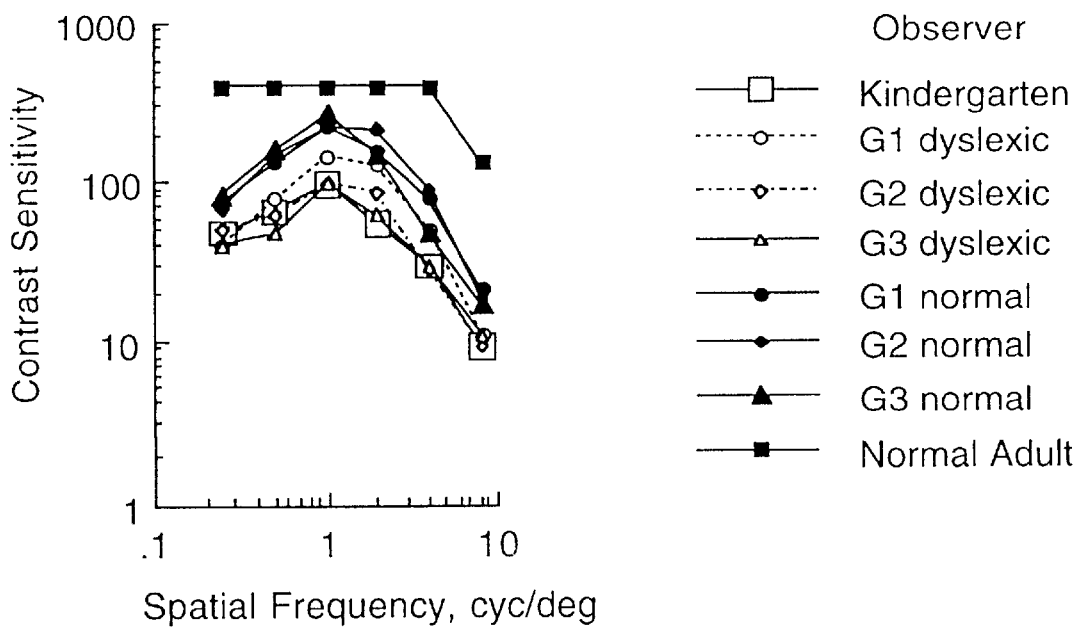

Discriminating the direction that a 0.25-cpd test frequency moved was perceived to be a different task by many students. Oscillation of the test frequency, instead of moving in a single direction was seen, especially when medium and high contrasts were needed to discriminate left-right movement. In addition, a different pattern of results was obtained, with the CSF being highest when the background was one octave lower than the test frequency, and lowest when the background was one octave higher than the test frequency. This pattern shows that maximum masking occurs at two times the value of the test frequency, at the second harmonic frequency, indicating nonlinear processing that could result from pooling across several different neural channels. This is particularly evident when examining FIG. 5d, showing the CSFs for 8 year olds when the test frequency equaled 0.25 cpd. Moreover, at this low test frequency, the differences between normal and dyslexic observers were not consistent across grade level, having the smallest differences between normal and dyslexic third graders, and the largest differences between normal and dyslexic first graders (shown in FIG. 7c). Furthermore, the CSF of the practiced 7-year-old child showed the most improvement (shown in FIG. 5f), suggesting that direction selectivity using this test frequency matures later than direction discrimination using higher test frequencies.

With only forty minutes of entertaining visual exercise, 5 to 10 minutes/week, rapid and effective remediation was provided when judged relative to a wide range of background frequencies. This study provides substantial evidence that practice discriminating left-right movement, especially at 6 to 7 years old, provides rapid remediation, most likely by developing networks in magnocellular streams. In addition, 10 to 40 minutes of entertaining visual exercise tunes up the networks in magnocellular (movement) streams so that direction discrimination CSFs improve 3 to 4 fold.

When asked in a questionnaire at the end of this study if the child noticed any difference in their reading ability following practice, all children said that reading out loud or silently was much easier, seeing the individual letters in the middle of a word was easier, spelling, and pronunciation were easier, as were reading comprehension, speed discrimination, motion parallax, seeing moving objects at a farther distance, and distance judgments. All children were grateful for the testing. They found the test entertaining and that they enjoyed reading a lot more and that they read a lot more, usually twice as much, immediately following the testing where the child practiced discriminating left-right movement. More practice gives more improvement in reading rates in all children, and major improvement can be obtained for just 5 to 10 minutes/week of play for 8 weeks.

The more a child practiced discriminating left-right movement, the more the child's reading rates increased, increasing up to 14 fold for one dyslexic second grader (m1) who had three practice thresholds on each pattern combination. With only two practice thresholds (shown in FIGS. 2f to 5f and FIGS. 8f to 13), a normal 6- to 7-year old child's CSF for equal test and background frequencies equaled the CSF of a normal adult. Moreover, remediation was most rapid when the direction of movement was judged relative to low background frequencies, providing a wide frame of reference for left-right movement discrimination, thereby facilitating movement discrimination.

The methodology of the present invention may be implemented in software and method for determining the lowest or "threshold" contrast required by a subject to discriminate the direction of motion, left versus right, of a vertical sine-wave grating of one spatial frequency (0.25, 0.50, 1.0, or 2.0 cycles per degree of visual field) in a small test window on a background containing a vertical sine-wave grating of a spatial frequency ¼, ½, 1, 2, and 4 times the test spatial frequency. The thresholds are determined objectively and rapidly by use of a two-alternative-forced-choice psychophysical method that is embedded in the fish game.

Contrast sensitivity is the reciprocal of contrast threshold. The contrast sensitivity function (CSF) for each test-pattern spatial frequency is the family of contrast sensitivities for that test-pattern spatial frequency over all of the predetermined background frequencies. Normal adult readers have high contrast sensitivities; moreover, the pattern of their CSFs show highest contrast sensitivity when the spatial frequency in the test window is matched by the spatial frequency in the background. Normal children without reading difficulty have somewhat lower CSFs but the normal pattern. Dyslexic subjects, both children and adults, have substantially lower CSFs and an inverted pattern in the CSFs; that is, their CSFs show lowest contrast sensitivity when the spatial frequency in the test window is matched by the spatial frequency in the background. Practice on the fish game causes direction discrimination CSFs to rise in all children and dyslexic adults, though dyslexic subjects start at a lower contrast sensitivity than normal readers. Practice on the fish game also causes the dyslexic pattern observed in CSFs to invert to the normal pattern. Along with these changes in CSFs, reading rates increase several fold in normal readers and even more in dyslexic subjects.

Figure 1C:
FIG. 1c is a plan view of text filtered in accordance with the present invention.
Figure 2A:
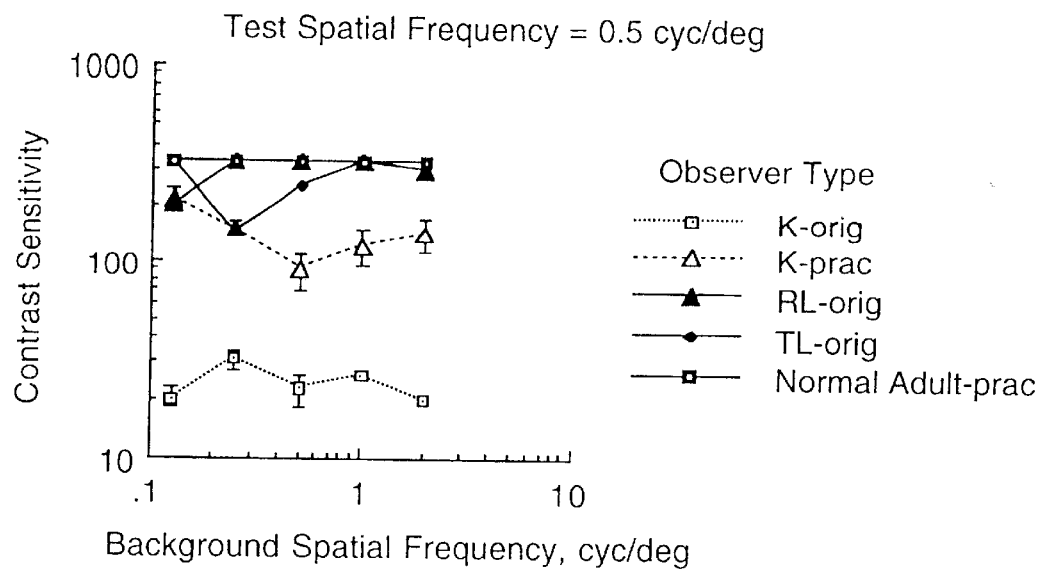
FIGS. 2a–2f are graphical views of data illustrating relationships between contrast sensitivity for direction discrimination with respect to spatial frequencies of the background for various subjects, including dyslexic and normal children, particularly illustrating the relationship at a spatial frequency of 0.5 cycle per degree of the test pattern.
Figure 2B:
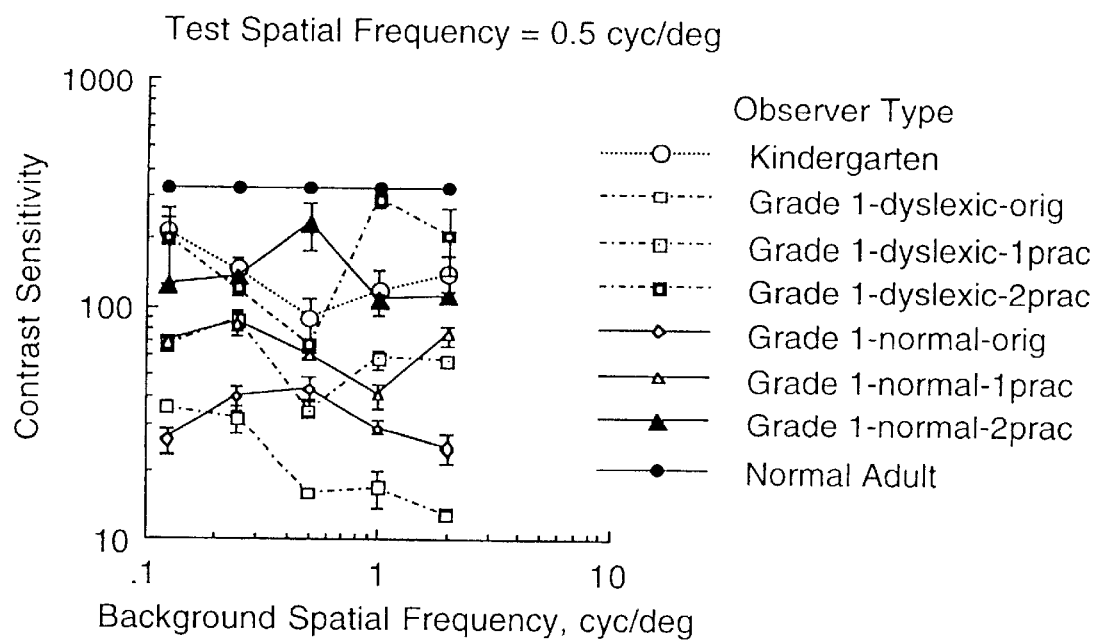
Figure 2C:
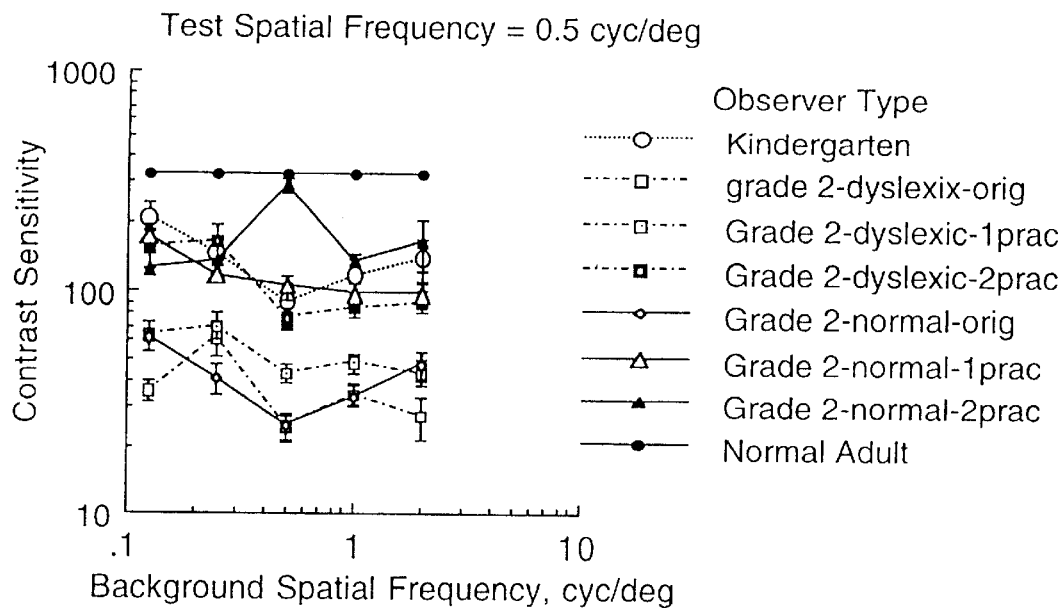
Figure 2D:
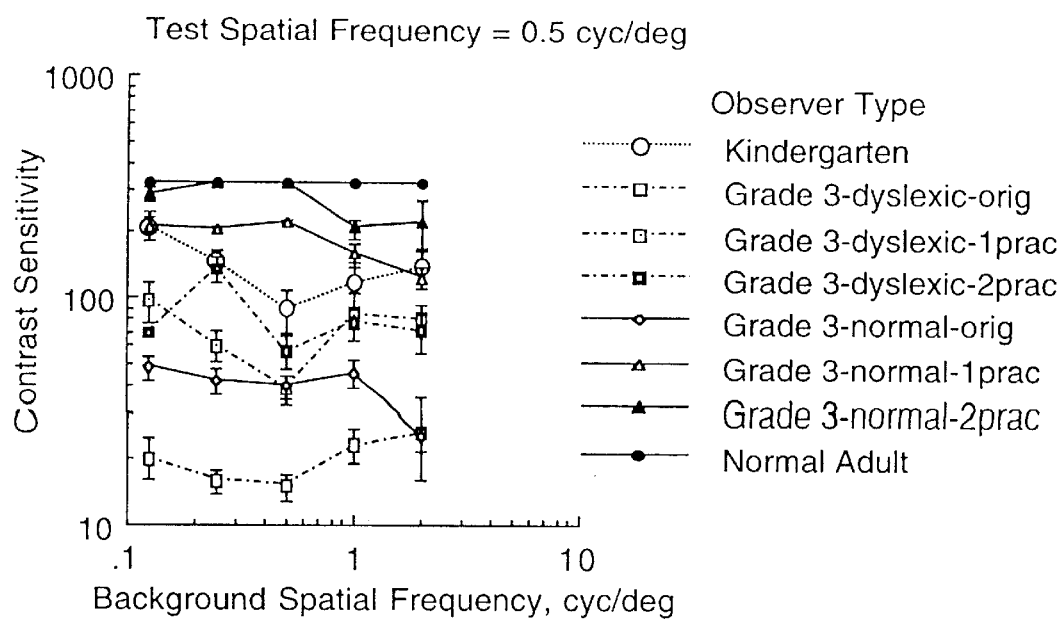
Figure 2E:
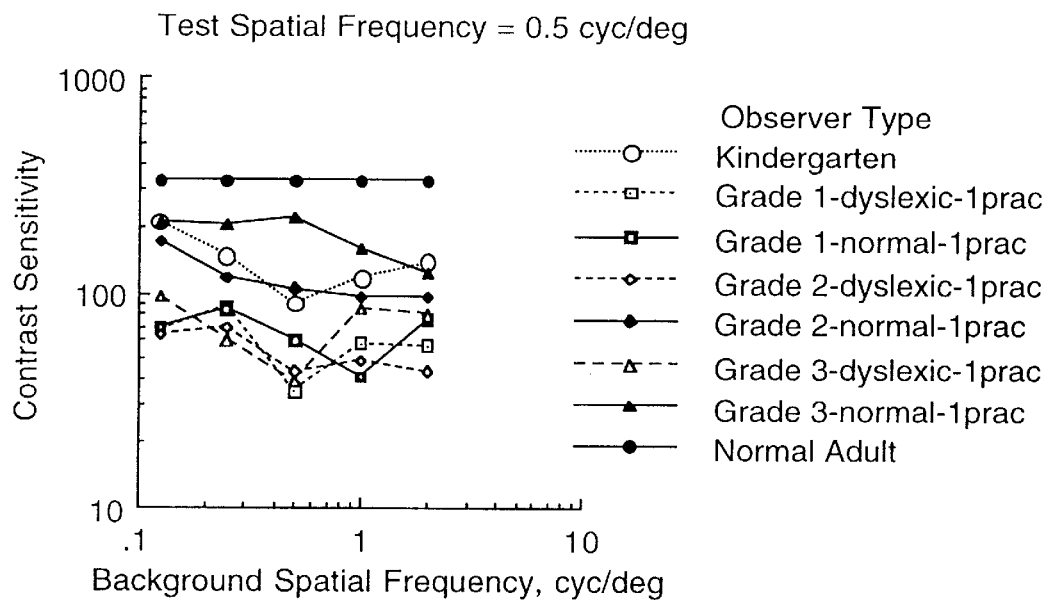
Figure 2F:
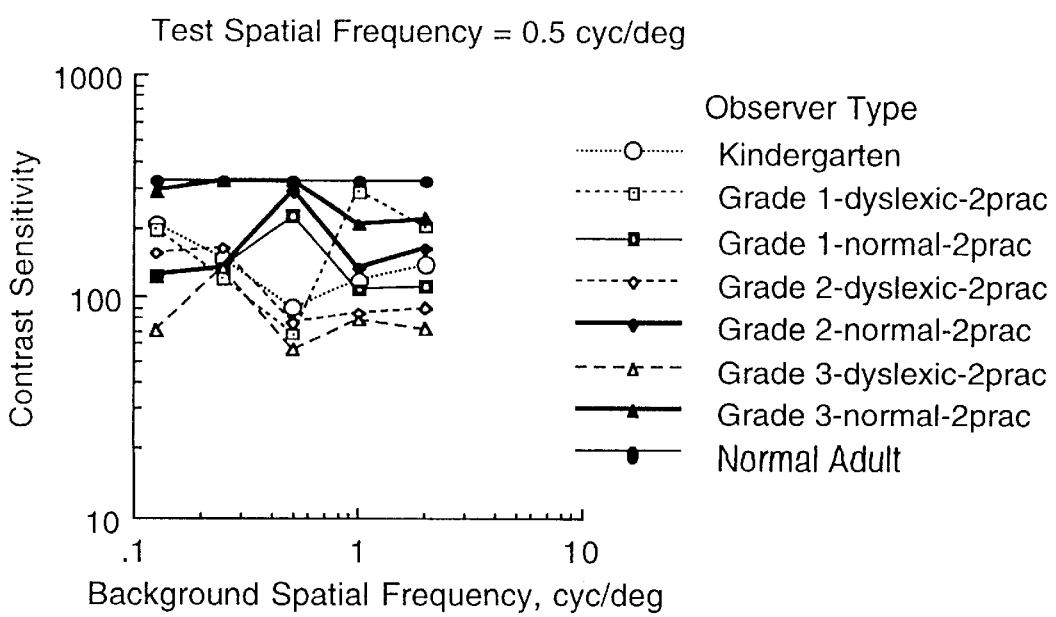

Unfiltered words of a sans-serif font, such as Lucida Sans Typewriter Bold, were used to create text that was centered on the display. A sans-serif font with rounded edges was chosen because this is the least ornate font, with no jagged or protruding edges, thereby being one of the easiest to read. Sample unfiltered text is shown in FIG. 1c. White text on a black background having 100% contrast was used for unfiltered text, since this text was easier for children to read than black text on a white background. Each letter in the text was 0.5 cm wide and 0.5 to 0.75 cm high, depending on whether upper or lowercase letters were displayed This size letter enabled text to be read easily at a distance of 57 cm from the screen. Reading materials were adapted from easy to understand text with a positive connotation, i.e., *Over In The Meadow*, by Jack Ezra Keats. This text was chosen, since it is taught to first graders at the elementary school used for testing. Therefore, the reading level of the text did not limit the child's reading performance. At the beginning of this study, the text had not been memorized by any of the children in this study. To ensure that the text could not be memorized, the text was extended from 80 sentences in the original text to 230 five word sentences, so that text that never repeated was used to measure reading rates for filtered and unfiltered text. Reading rates at the end of the study were measured using only the novel text, so that memorization could not contribute to measuring faster reading rates. Subsequent portions of the same text were used to test reading rates for both filtered and unfiltered words, so that the reading of sentences in the text was continuous, yet never repetitive. Therefore, text of equal difficulty was used throughout the reading rate task to measure grayscale and colored text that was either filtered or unfiltered. Since most of the text was novel, being written by the author, in conjunction with the school's reading specialist and a 6-year-old child, unfamiliar reading materials were used, for the most part to measure reading rates.

Words were first magnified and then filtered, since reading performance is based on retinal based angular frequencies, and not object-based spatial frequencies. Words were filtered as a unit, and the filtered words, having a border equal to one letter width, were strung together in texts. There were often borders between the filtered word images, due to the scaling mentioned above. All children reported, however, that these borders were blurred and did not help segment the text string into words. The space between each word was the more salient cue that was used to segment the text string.

Samples of filtered text for several children in this study are shown in FIG. 1c. The individualized filters, causing white on black text to be displayed in shades of gray, are matched to each observer's CSF, to compensate for these CSF losses. Note that filtered text for each observer has different amounts of enhancement across the range of spatial frequencies tested, seen as differences in the amount and extent of dark ringing around each letter. The transfer function of the filter was designed to enhance images that have been degraded by noisy detectors when the degrading optical transfer function, like the Normalized CSF (NCSF), discussed below, as used in this study, is known. The detailed methods used to construct these filters have been described previously and are also presented below.

The number of words per minute was increased on each step by increasing the distance in pixels that the image moves between frames. Each sentence, flanked by four letters of adjacent text at the beginning and end, was scrolled from right to left at different speeds. The number of pixels the image moved before beginning each frame was adjusted so that the image moved over to the right a larger number of pixels at higher reading rates. The step size for increasing reading rates increased gradually using a 12 words/min step size at low reading rates, and up to a 30 words/min step size at high reading rates. The reading speeds were measured with a digital stopwatch. The updating of the text images (scrolling) occurred at regular intervals, enabling Xwindow primitives to generate smooth scrolling of text at all speeds.

Reading rates, defined as the fastest speed that can be used to read filtered or unfiltered text scrolled across the screen, were measured after the CSFs were determined. Reading rates were only measured for children in grades 1 to 3. Filtered or unfiltered text was displayed at increasing speeds, from 10 words/minute up to 700 words/minute, until the child could no longer correctly identify the text. Reading rates were measured after one complete sentence had been presented to the child who read the sentence out loud, either during or after the sentence was displayed. The next sentence was displayed as soon as the child finished reading the sentence. Following the first incorrect response, a forced-choice double-staircase procedure, determining the speed for 79% correct responses, was used to determine reading rate thresholds by increasing or decreasing the speed used to scroll each sentence across the screen. The child had to correctly identify each subsequent sentence in the text being scrolled across the screen three times in a row at the same speed, before the reading speed was increased one step. The reading speed was decreased one step each time the sentence was identified incorrectly. The sentence was scored as identified correctly if 4 of 5 words were correct and in the right order.

Filtered text was presented before unfiltered text to counterbalance any effects of practice that might be attributed to the improved reading rates found when reading filtered text. Since reading rates always increased over the session, fatigue did not contribute to the slower reading rates obtained for unfiltered text. Unfiltered and filtered texts were cycled through in the same order throughout the session so that practice effects were distributed equally across filtered and unfiltered text. One to two thresholds for each type of text, depending on the difficulty the observer had reading, were used to determine the mean reading rate threshold.

Figure 14A:
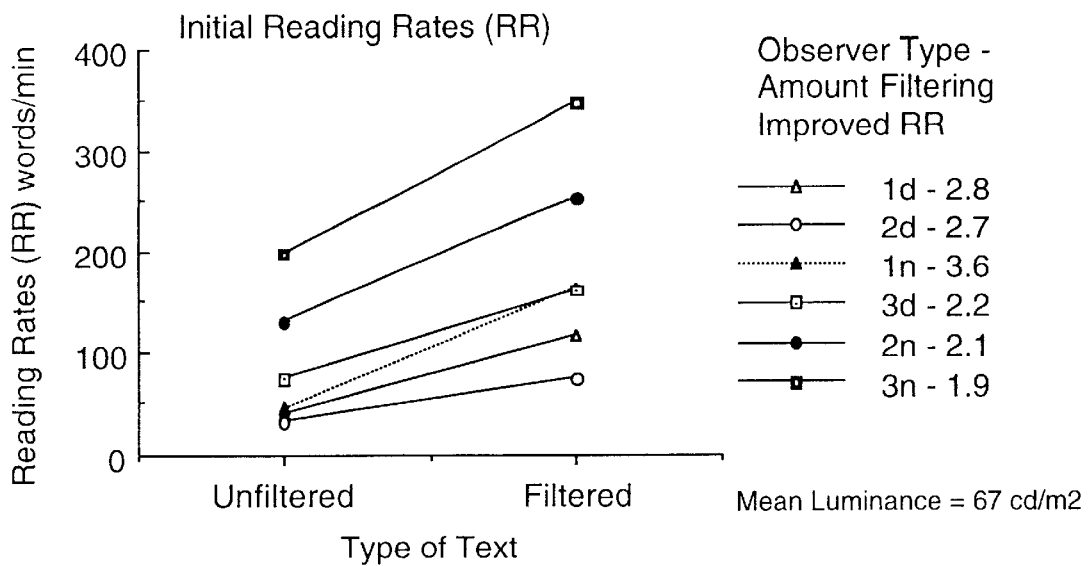
FIGS. 14a–14c are graphical views of data illustrating relationships between reading rates with respect to filtered and unfiltered text for various subjects.
Figure 14B:
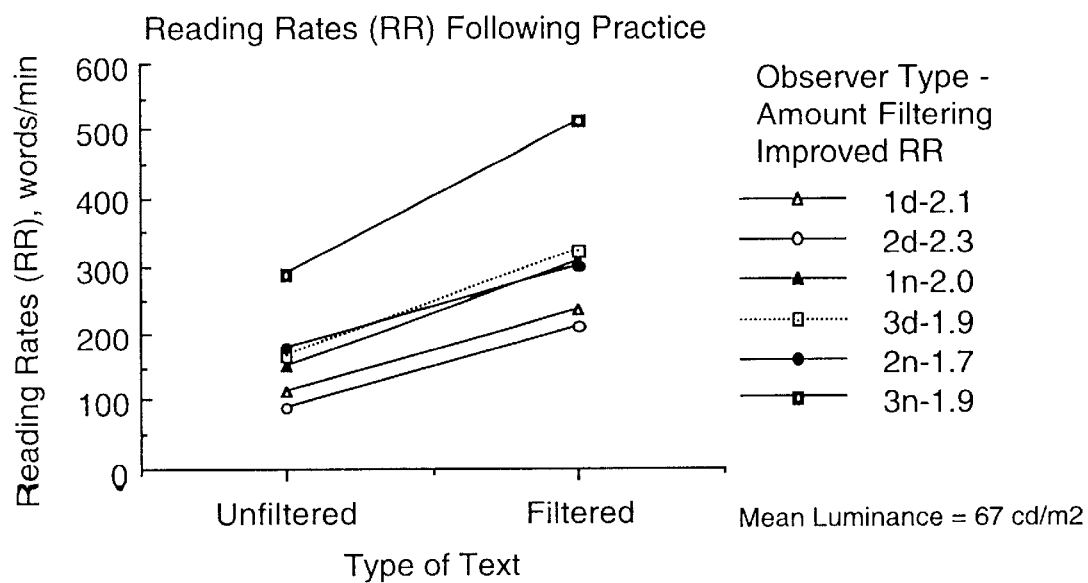
Figure 14C:
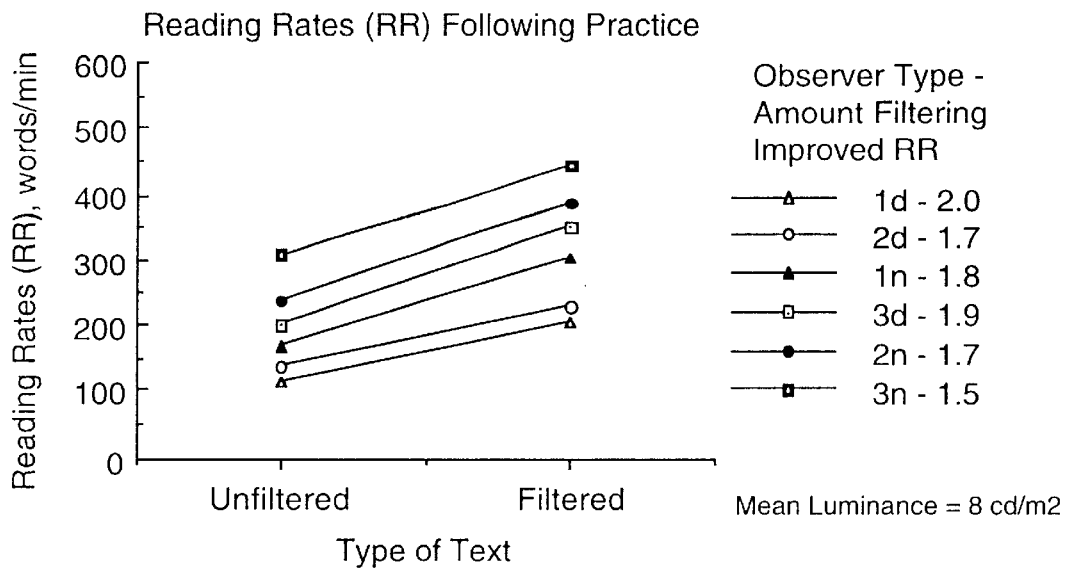

A child's ability to read is developing as the child advanced in age from 6 to 8 years old. We found that the mean reading rates for unfiltered text were significantly faster (p<0.0001) as the normal child advanced from first to third grade, when analyzed using a test for paired comparisons. This was found at the beginning of this study (shown in FIG. 14a), following practice (shown in FIG. 14b), and following practice at the low mean luminance, e.g., 8 cd/m$^2$ (shown in FIG. 14c), used to evaluate the effects of colored filters on reading rates.

Filtered text was always read at least 2 fold faster, on average, than unfiltered text, as illustrated in FIGS. 15a–d. By compensating for CSF losses to discriminate between brief orthogonally oriented sine-wave gratings, filtered text enabled the child to read significantly faster (p<0.0001). All children reported that the filtered text improved their ability to see individual letters in each word. Filtered text improved reading rates about 3 fold for 6 to 7 year olds and 2 fold for 8 year olds before practice, and about 2 fold after practice, as shown FIGS. 14a–c.

As the child's sensitivity more closely approached the CSF of an adult, the less the filtered text proportionately improved reading rates. Filtered text can be used not only to improve reading performance, but also to provide a second type of text to test the relative improvement in a child's reading ability following various types of remediation. In addition, finding that reading rates increased from 3 to 14 fold, when CSF losses were compensated for by these image enhancement filters and the child practiced discriminating left-right movement, shows that children's CSFs to discriminate between orthogonally orientated brief patterns and discriminate the direction of movement are closely related to their reading performance.

Figure 15A:
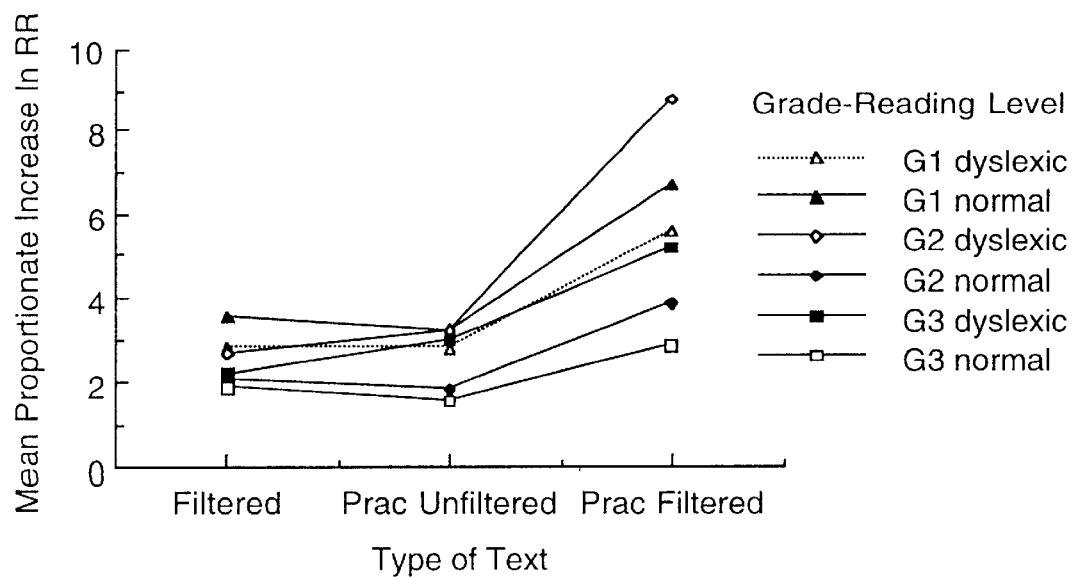
FIGS. 15a–15e are graphical views of data illustrating relationships between proportional improvements in reading rates with respect to filtered and unfiltered test for various subjects.
Figure 15B:
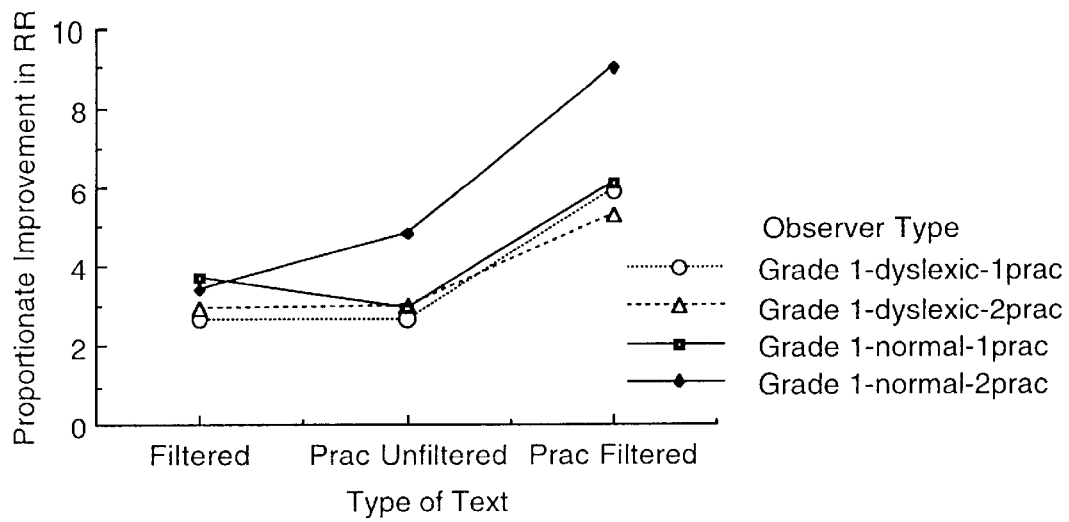
Figure 15C:
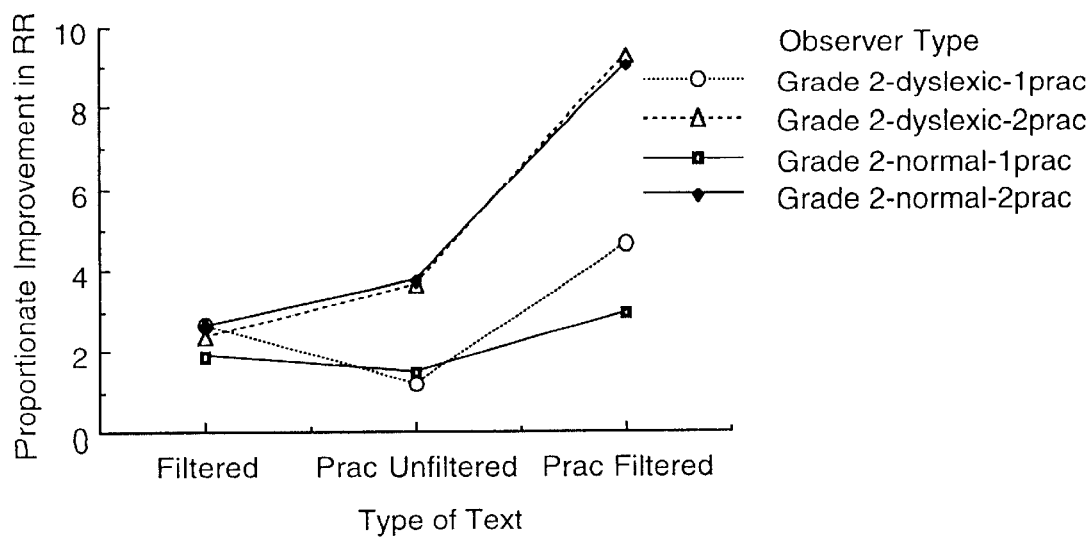

Practice on each of 20 different test-background frequency combinations improved reading rates from 2 to 9 fold on the average (shown in FIG. 15a). Since a difference of 20 words per minute for slow readers can correspond to a doubling in their reading rates, whereas this difference for fast readers would not be significant, each student's mean reading rate for filtered text was divided by the mean reading rate for unfiltered text, normalizing the proportion the student improved when reading filtered text. Only in this manner can proportionate improvements in reading rates for different students, between filtered and unfiltered text before and after practice, be compared and pooled to provide summary curves, as shown in FIGS. 15a–d. All proportionate increases greater than 1.0 show that reading rates were faster for filtered text than for unfiltered text. One second-grade child with reading problems improved up to 14 fold after practicing 3 to 5 times on each of the 20 different test pattern/background combinations.

Figure 15D:
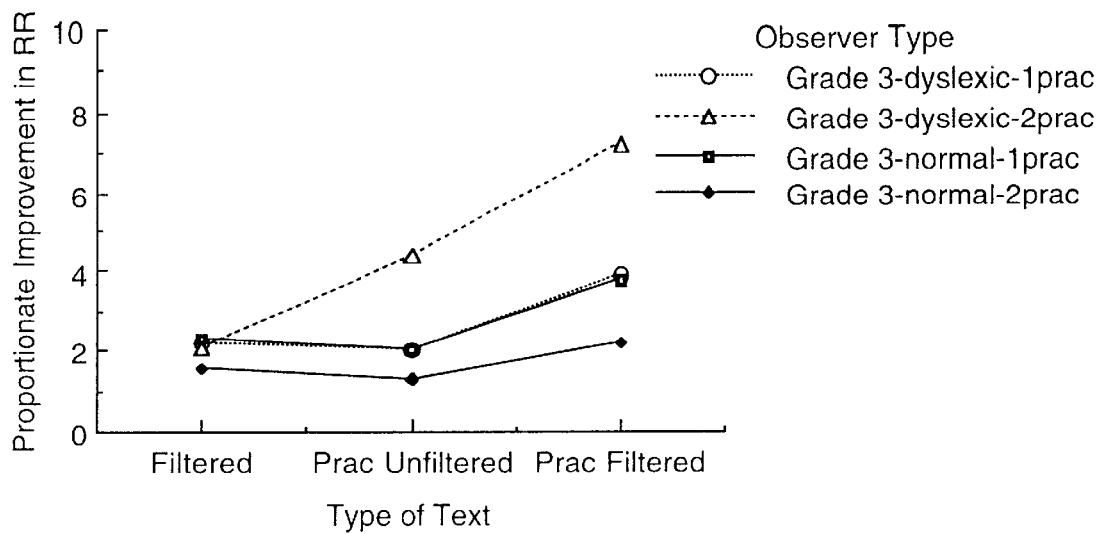
Figure 15E:
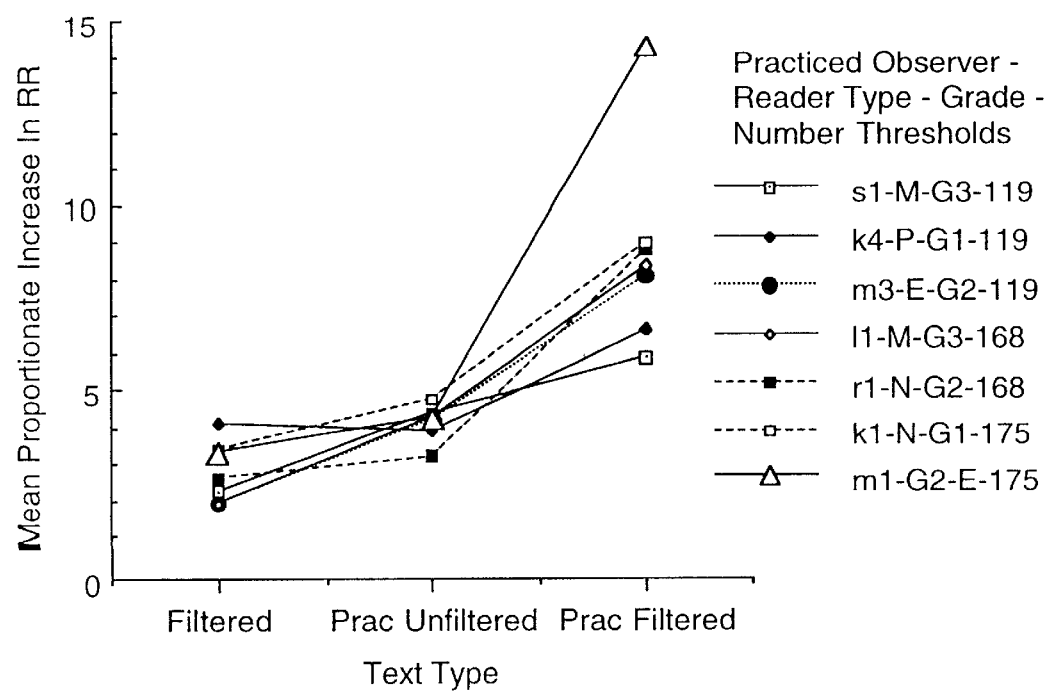

Following practice discriminating left-right movement, reading rates for filtered text approximately doubled again from the reading rates for filtered text measured initially. Therefore, instead of measuring a 2- to 3-fold improvement in reading rates for filtered text (shown in FIG. 15b), a 3- to 9-fold average improvement in filtered reading rates following practice was measured (shown in FIG. 15c). Moreover, following two practice thresholds, a 9-fold improvement in reading rates when reading filtered text, with a 4-fold improvement when reading unfiltered text, was found for the normal first-grade child (shown in FIG. 15b), both the normal and dyslexic second-grade child (shown in FIG. 15c), and the dyslexic third-grade child (FIG. 15d). Thus, filtered text for remediation is most effective when the child is 6 to 7 years old, which coincides with the development of the neural channels used for reading.

Filtered text can be used not only to improve reading performance, but also to provide a second type of text to test the relative improvement in a child's reading ability following various types of remediation. In addition, finding that reading rates increased from 3 to 14 fold, when CSF losses were compensated for by these image enhancement filters and the child practiced discriminating left-right movement, shows that children's CSFs to discriminate between orthogonally orientated brief patterns and discriminate the direction of movement are closely related to their reading performance.

This example shows that spatial filtering is a powerful tool for improving the reading performance of ARMD observers. The transfer function of the filter is designed to enhance images that have been degraded by noisy detectors, when the degrading optical transfer function, like the NCSF as used in this study, is known It is also important to adjust the filter design parameters (see below) so that reading rates are optimized, and to ensure that the angular pixel spacing is sufficiently small. This filtering approach replaces in advance, at the front end, the contrast that is selectively reduced by the child's developing visual system. By boosting the less visible spatial frequency components, we are making pattern components in the spatial frequency band that is used for reading easier to see. The combination of text prefiltering and reduced visual function presumably presents to that child's brain letters having spatial frequency components with the same relative amplitudes as those seen by a normal adult observer. In other words, precompensation filtering for a known degradation is used to improve a child's reading performance. In addition, the filtered text provided a second independent measure used to evaluate improvements in a child's reading performance following practice.

These image enhancement filters are unique and work well to improve the reading performance of observers with CSF losses compared to a normal adult, because (1) the use of the observer's NCSF to quantify their CSF losses in the design of the filtering transfer function H(f), (2) the use of the form of H(f) in Equation (3) below which has been shown to be effective in deblurring of noisy images when compared to simpler filtering functions such as 1/NCSF or 1/(NCSF+constant), (3) the filtering parameter, MaxGain, is adjusted so that it is optimized for the display screen's pixel density, and (4) the observer's viewing distance is adjusted so that static text is read most easily at this distance. Only when text is enhanced using the individualized NCSF-based filters described in this study does filtered text significantly reduce the magnification required for reading and increase reading rates in observers with CSF losses.

Although the mean reading rates for all dyslexic and normal children in this study increased significantly ($p<0.0000000001$ [E-19]) as the child advanced from first to third grade, as shown in FIGS. 14$a$–$c$, the average 30% reduction in reading speed that was found when reading colored text having the same contrast and mean luminance, 8 cd/m2, as grayscale text was quite constant across: (1) colors, i.e., green, red, blue, and yellow text, (2) type of text, filtered or unfiltered, as shown in FIG. 1$b$, and (3) type of observer, dyslexic or normal in grades 1 to 3, with colored text being read significantly more slowly ($p<0.0000000001$) than grayscale text. In fact, the reading rates for equiluminant text having only color contrast, tested on a subset of these students, were read even 30% slower, on the average, than colored text have both luminance and color contrast. This same pattern of results was found for adults also. Therefore, when parvocellular networks were activated more than magnocellular networks by presenting colored text, then reading rates were always reduced.

Grayscale clipping of the displayed stimulus was avoided by scaling the minimum pattern intensity to the lowest display intensity and the maximum pattern intensity to the highest display intensity, using linear interpolation. The resealing does not change the relative contrast of the Fourier components in the image, since both linear interpolation and Fourier analysis are linear operations. It does, however, modify the mean luminance level of text and background, compressing the contrast range of the filtered text (shown in FIG. 1$c$). The background goes from black to gray to make room for the dark outline the filter places around each letter. The filtered text was stored off-line to be used in the next session for testing the observer's reading rates.

The transfer function chosen for the image-enhancement filter in accordance with the invention is:

$$H(f) \; NCSF(f) \div [NCSF^2(f)+(2MaxGain)^{-2}] \quad (1)$$

where f is the radial spatial frequency expressed in cyc/deg by:

$$f=sqrt(u^2+v^2) \quad (2)$$

where u and v are horizontal and vertical spatial frequency, respectively, and NCSF(f) is defined to be:

$$NCSF(f)=\text{Child's } CSF(f) \div \text{Normal Adult's } CSF(f) \quad (3)$$

The transfer function is designed to enhance noisy images that have been degraded by a known optical transfer function. The maximum amount of enhancement in the spatial frequency domain using this transfer function is set by the factor MaxGain. It is important that the MaxGain value that maximizes reading rates be determined for the display being used to present filtered text. Otherwise, the filtered text will not improve reading rates over unfiltered text. Thus, empirically we discovered that the optimal value for MaxGain is dependent on the display's pixel density, such that a higher MaxGain, i.e. more enhancement, is needed when the screen has a lower pixel density. MaxGain was set to 4.5 for this study, since this value was optimal for all observers tested. Moreover, it is important that the transfer function be anchored at zero spatial frequency to no enhancement to ensure that the same range of contrasts are being compared when reading filtered and unfiltered text.

The pixel density on the display screen was measured as 40 pixels per centimeter, implying a pixel spacing of $\Delta x=0.025$ cm. The angular pixel spacing at the observer's eye, using the small angle approximation, is:

$$\arctan\,[\Delta x/d] \approx \Delta x/d \quad (4)$$

in radians, where d is the viewing distance in cm, or:

$$\Delta\theta=(\Delta x/d)(180/\pi)=4.5/\pi d \quad (5)$$

in degrees. The constant $180/\pi$ converts from radians to degrees. This is 0.025 degrees at a 57 cm viewing distance. We used the Discrete Fourier Transform (DFT), and the Nyquist (folding) frequency is:

$$f_N=1/(2\Delta\theta)=\pi d/9 \quad (6)$$

in cycles per degree (cyc/deg). This is 19.9 cyc/deg at a 57 cm viewing distance.

For each subject, we composed a 15-by-15 element two-dimensional transfer function by spreading the H(f) values for that subject radially from f=0 at the origin of frequency space up to $f=sqrt(F_N)$ at the end of each axis. In the transfer function, horizontal frequency, u, and vertical frequency, v, varied between $-sqrt(F_N)$ and $sqrt(F_N)$ in 15 equal steps.

This range of spatial frequencies enabled filtering frequency components from 0.8 up to 4.5 cyc/deg. This frequency scaling using sqrt($F_N$) to delimit the upper frequency cutoff, instead of $f_N$, shifting the range of spatial frequencies being filtered to 3 fold lower spatial frequencies, was shown to improve reading rates by approximately 20% when compared to filtering up to the Nyquist frequency, $f_N$. Moreover, data in our laboratory subsequent to this study, on five second-grade students, both normal and dyslexic, found the same 20% improvement in reading rates when using sqrt ($F_N$) to delimit the upper frequency cutoff, instead of $f_N$. Since only spatial frequencies spanning 3 cycles/letter are used for letter recognition, then for letters 0.5 cm wide that are seen at a viewing distance of 57 cm, only spatial frequencies up to 6 cyc/deg are used for letter recognition. Each enhancement filter was designed not only for a specific subject, but for a specific viewing distance as well, since the Nyquist frequency [Eq. (6)] is distance dependent The inverse DFT was used to compute a 15-by-15 convolution kernel to be used for enhancement.

Since the transfer function was generated to be circularly symmetric about zero frequency, the computed convolution kernel was circularly symmetric about the origin as well. Also, since each observer's CSF was expressed in angular frequency, differences in viewing distance were accounted for intrinsically. Words were filtered in the spatial domain by the process of convolution, that is, by summing the products of the 15-by-15 coefficient weights of the convolution kernel times the gray level of each center pixel and its surrounding 224 pixels. The filtered pixel intensity=Sum (15×15 spatial filter * unfiltered pixel value). The elements of the spatial filter kernel matrix, computed by the DFT, were ordered to be symmetrical about the center of the filter. The largest weights were in the center of the filter.

The uniqueness of the approaches exemplified above to investigate vision and reading is based on five different lines of evidence. First, this study found a different pattern of results between normal and dyslexic children, both before and after practice, when discriminating the direction of moving patterns, enabling rapid and reliable screening for dyslexia in 5 minutes for children in grades 1 to 3. This different pattern of results shows the importance of evaluating inhibitory networks for rapid dyslexia screening. Only by mapping out the CSFs for test frequencies surrounded by one of a 4 octave range of background frequencies, centered about the test frequency, were these uniquely different direction discrimination CSFs found for normal and dyslexic children. Moreover, only by judging movement relative to background frequencies equal to or higher than the test frequency, were the integrity of inhibitory networks able to be uncovered. Second, 10 to 40 minutes of entertaining visual exercise tunes up the inhibitory networks in magnocellular (movement) streams so that both direction discrimination CSFs improved 3 to 4 fold, and reading rates improved 3 to 14 fold, in addition to markedly noticeable improvements, at least a doubling, in reading comprehension, spelling, pronunciation, as well as movement and depth discrimination. Third, when vertically oriented sine-wave gratings were presented to measure direction discrimination thresholds, enabling the output of simple cells to mediate discrimination, then 9-fold larger differences between normal and dyslexic children were measured, than found previously using random dot patterns, showing that vertical sine-wave gratings are the optimal stimulus for rapid and reliable screening. Fourth, measuring reading rates to continuous, non-repetitive, easy-to-read, scrolled text, provides an objective measure of reading performance that can be made before and after practice discriminating left-right movement to evaluate improvements in reading, instead of measuring reading performance by relying on subjective teacher evaluations, as is currently done. In addition, definitive evidence that magnocellular, and not parvocellular networks, play a major role in reading was obtained by comparing reading rates for grayscale and colored text equated in luminance and contrast. Fifth, individualized filtered text that compensates for losses in a child's CSF to discriminate between orthogonally oriented brief patterns, compared to a normal adult, improved reading rates from 2 to 4 fold, providing more evidence that magnocellular networks play a major role in reading, and that they are still developing in all children 5 to 9 years old. This filtered text not only can be used for remediation, but also can be used to provide a second independent measure of reading rates, when compared to high contrast unfiltered text, to objectively evaluate improvements in reading performance. This unique approach provides conclusive evidence that magnocellular and inhibitory networks in the brain play a major role in reading, both in directing eye movements and in word recognition.

Those skilled in the art will understand that the preceding exemplary embodiments of the present invention provide the foundation for numerous alternatives and modifications thereto. These other modifications are also within the scope of the present invention. Accordingly, the present invention is not limited to that precisely as shown and described above.

What is claimed is:

1. A method for diagnosing dyslexia by measuring contrast sensitivity for motion discrimination of a subject having a visual cortical movement system, said method comprising the steps of:
    (a) displaying a background with a contrast and a spatial frequency;
    (b) displaying a test window within said background, said test window including a test pattern with a contrast and a spatial frequency, said test pattern replacing said background;
        said contrasts being within a range which stimulates the visual cortical movement system of the subject;
        said spatial frequencies being within a range which stimulates the visual cortical movement system of the subject;
    (c) moving said test pattern within said test window in either a first direction or a second direction;
    (d) receiving a signal from the subject indicative of either said first direction or said second direction;
    (e) modifying at least one of said contrasts or said spatial frequencies in response to said signal;
    (f) repeating steps (a) through (e); and
    (g) using the signals from the subject as criteria for forming a diagnosis of dyslexia.

2. A method as claimed in claim 1 wherein said step of displaying a test window comprises the step of:
    displaying said test pattern with a spatial frequency selected from a predetermined range of spatial frequencies;
    said predetermined range of spatial frequencies of said test pattern including spatial frequencies ranging from about 0.25 cycle per degree to about 2 cycles per degree.

3. A method as claimed in claim 2 wherein said step of displaying a background comprises the step of:
    displaying said background with a spatial frequency selected from a predetermined range of spatial frequencies;

said predetermined range of spatial frequencies of said background including spatial frequencies that are ¼, ½, 1, 2, and 4 times said spatial frequency at which said test pattern is displayed.

4. A method as claimed in claim 3 wherein said modifying step comprises the steps of:
increasing said contrast of said test pattern if said signal is incorrect; and
decreasing said contrast of said test pattern if said signal is correct.

5. A method as claimed in claim 4, wherein said step of modifying further comprises the steps of:
varying said spatial frequency at which said background is displayed while maintaining constant said spatial frequency at which said test pattern is displayed.

6. A method as claimed in claim 5, wherein said step of modifying further comprises the steps of:
varying said spatial frequency at which said test pattern is displayed after said spatial frequency of said background is varied through each of said spatial frequencies of said predetermined range of spatial frequencies.

7. The method of claim 4, wherein the contrast of said test pattern is decreased only when a sequential number of signals are correct.

8. The method of claim 7, wherein the number is three.

9. A method as claimed in claim 1 wherein:
said step of displaying a background comprises the step of displaying said background at a contrast selected from a predetermined range of contrasts; and
said step of displaying a test window comprises the step of displaying said test pattern at a contrast selected from a predetermined range of contrasts;
said predetermined ranges of contrasts including contrasts of less than about 10%.

10. A method as claimed in claim 9, wherein said step of displaying a background comprises the step of:
displaying said background at a contrast of about 5%.

11. A method as claimed in claim 1 wherein:
said step of displaying a test window comprises the step of displaying said test pattern at an initial position within said test window for a predetermined period; and
said step of moving comprises the step of displaying said test pattern at a final position within said test window for a predetermined period.

12. A method as claimed in claim 11, wherein:
said step of displaying said test pattern at an initial position comprises the step of displaying said test pattern for less than about 0.2 second; and
said step of displaying said test pattern at a final position comprises the step of displaying said test pattern for less than about 0.2 second.

13. A method as claimed in claim 11, wherein:
said step of displaying a background comprises the step of displaying said background as substantially vertical stripes which alternate sinusoidally between light and dark at said spatial frequency; and
said step of displaying a test window comprises the step of displaying said test pattern as substantially vertical stripes which alternate sinusoidally between light and dark at said spatial frequency.

14. A method as claimed in claim 8 wherein said step of moving comprises the step of displaying said test pattern at said final position, said second position being either to the right or to the left of said first position;
said predetermined periods at which said test pattern is displayed at said initial and final positions being of a duration to induce in the subject an apparent sense of motion of said stripes moving right or left from said initial position to said final position.

15. A method as claimed in claim 1 wherein said method diagnoses dyslexia by measuring an absolute value of the contrast sensitivity for motion discrimination.

16. A method as claimed in claim 15, further comprising the steps of:
storing data based on said signals received from the subject; and
determining the contrast sensitivity based on said data.

17. A method as claimed in claim 1 wherein said method diagnoses dyslexia by measuring contrast sensitivity for motion discrimination to yield a contrast sensitivity function with a shape.

18. A method as claimed in claim 1 wherein said method further improves the contrast sensitivity function for motion discrimination of the subject.

19. A method as claimed in claim 1 wherein said method further improves reading rate of the subject by improving the contrast sensitivity for motion discrimination.

20. Apparatus for improving contrast sensitivity for movement discrimination of a subject having a visual cortical movement system, said apparatus comprising:
a monitor; and
a computer connected to said monitor, said computer being configured to:
(a) display a background with a contrast and a spatial frequency;
(b) display a test window within said background, said test window including a test pattern with a contrast and a spatial frequency said test pattern replacing said background;
said contrasts being within a range which stimulates the visual cortical movement system of the subject;
said spatial frequencies being within a range which stimulates the visual cortical movement system of the subject;
(c) move said test pattern within said test window in either a first direction or a second direction;
(d) receive a signal from the subject indicative of either said first direction or said second direction;
(e) modify at least one of said contrasts or said spatial frequencies in response to said signal; and
(f) repeat steps (a) through (e) a plurality of times.

21. The apparatus of claim 20, operated to improve contrast sensitivity for movement discrimination of a subject having a visual cortical movement system.

22. The apparatus of claim 20 operated to improve the reading rare of a subject having a visual cortical movement system.

23. Apparatus as claimed in claim 20, wherein said computer is further configured to display said test pattern with a spatial frequency selected from a predetermined range of spatial frequencies;
said predetermined range of spatial frequencies of said test pattern including spatial frequencies ranging from about 0.25 cycle per degree to about 2 cycles per degree.

24. Apparatus as claimed in claim 23, wherein said computer is configured to display said background with a spatial frequency selected from a predetermined range of spatial frequencies;

said predetermined range of spatial frequencies of said background including spatial frequencies that are ¼, ½, 1, 2, and 4 times said spatial frequency at which said test pattern is displayed.

25. Apparatus as claimed in claim 20, wherein said computer is configured to:
    display said background at a contrast selected from a predetermined range of contrasts; and
    display said test pattern at a contrast selected from a predetermined range of contrasts;
    said predetermined ranges of contrasts including contrasts of less than about 10%.

26. Apparatus as claimed in claim 25, wherein said computer is configured to display said background at a contrast of about 5%.

27. Apparatus as claimed in claim 20, wherein said computer is configured to:
    display said test pattern at an initial position within said test window for a predetermined period; and
    display said test pattern at a final position within said test window for a predetermined period.

28. Apparatus as claimed in claim 27, wherein said computer is configured to display said test pattern at both of said positions for less than about 0.2 second.

29. Apparatus as claimed in claim 20, wherein said computer is configured to vary said contrast at which said test pattern is displayed.

30. Apparatus as claimed in claim 29, wherein said computer is configured to vary said spatial frequency at which said background is displayed.

31. Apparatus as claimed in claim 30, wherein said computer is configured to vary said spatial frequency at which said test pattern is displayed.

32. Apparatus as claimed in claim 20, wherein said computer is further configured to display a blank field on said monitor before displaying said background and after moving said test pattern.

33. Apparatus as claimed in claim 20, wherein said test window is substantially circular.

34. Apparatus as claimed in claim 20, wherein said background is substantially larger than said test window.

35. Apparatus as claimed in claim 20, wherein said computer is configured to display said field such that said test is about 20% as large as said background.

36. The apparatus of claim 20, wherein the contrast of the test pattern is increased if the signal is incorrect, and wherein the contrast of the test pattern is decreased if the signal is correct.

37. The apparatus of claim 36, wherein the contrast of said test pattern is decreased only when a sequential number of signals are correct.

38. The apparatus of claim 37, wherein the number is three.

39. An article of manufacture comprising:
    storage medium readable by a computer; and
    plurality of instructions stored on said storage medium and including instructions for:
    (a) configuring the computer to display on a monitor a background with a contrast and a spatial frequency;
    (b) configuring the computer to display on a monitor a test window within said background, said test window including a test pattern with a contrast and a spatial frequency, said test pattern replacing said background pattern;
        said contrasts being within a range which stimulates the visual cortical movement system of the subject;
        said spatial frequencies being within a range which stimulates the visual cortical movement system of the subject;
    (d) configuring the computer to move said test pattern within said test window in either a first direction or a second direction;
    (e) configuring the computer to receive, via an input device connected to the computer, from a subject a signal indicative of either said first direction or said second direction; and
    (f) configuring the computer to modify at least one of said contrasts or spatial frequencies in response to said signal; and
    (g) configuring said computer to repeat steps (a) through (f).

40. A method for improving contrast sensitivity for motion discrimination of a subject having a visual cortical movement system, said method comprising the steps of:
    (a) displaying a background with a contrast and a spatial frequency;
    (b) displaying a test window within said background, said test window including a test pattern with a contrast and a spatial frequency, said test pattern replacing said background;
        said contrasts being within a range which stimulates the visual cortical movement system of the subject;
        said spatial frequencies being within a range which stimulates the visual cortical movement system of the subject;
    (c) moving said test pattern within said test window in either a first direction or a second direction;
    (d) receiving a signal from the subject indicative of either said first direction or said second direction;
    (e) modifying at least one of said contrasts or said spatial frequencies in response to said signal;
    (f) repeating steps (a) through (e).

41. A method as claimed in claim 40, wherein said step of displaying a test window comprises the step of:
    displaying said test pattern with a spatial frequency selected from a predetermined range of spatial frequencies;
    said predetermined range of spatial frequencies of said test pattern including spatial frequencies ranging from about 0.25 cycle per degree to about 2 cycles per degree.

42. A method as claimed in claim 41, wherein said step of displaying a background comprises the step of:
    displaying said background with a spatial frequency selected from a predetermined range of spatial frequencies;
    said predetermined range of spatial frequencies of said background including spatial frequencies that are ¼, ½, 1, 2, and 4 times said spatial frequency at which said test pattern is displayed.

43. A method as claimed in claim 42, wherein said modifying step comprises the steps of:
    increasing said contrast of said test pattern if said signal is incorrect; and
    decreasing said contrast of said test pattern if said signal is correct.

44. A method as claimed in claim 43, wherein said step of modifying further comprises the steps of:
    varying said spatial frequency at which said background is displayed while maintaining constant said spatial frequency at which said test pattern is displayed.

45. A method as claimed in claim 44, wherein said step of modifying further comprises the steps of:

varying said spatial frequency at which said test pattern is displayed after said spatial frequency of said background is varied through each of said spatial frequencies of said predetermined range of spatial frequencies.

46. The method of claim 43, wherein the contrast of said test pattern is decreased only when a sequential number of signals are correct.

47. The method of claim 46, wherein the number is three.

48. The method of claim 47, wherein the contrast of said test pattern is decreased only when a sequential number of signals are correct.

49. The method of claim 48, wherein the number is three.

50. A method as claimed in claim 40, wherein:

said step of displaying a background comprises the step of displaying said background at a contrast selected from a predetermined range of contrasts; and said step of displaying a test window comprises the step of displaying said test pattern at a contrast selected from a predetermined range of contrasts;

said predetermined ranges of contrasts including contrasts of less than about 10%.

51. A method as claimed in claim 50, wherein said step of displaying a background comprises the step of:

displaying said background at a contrast of about 5%.

52. A method as claimed in claim 40, wherein:

said step of displaying a test window comprises the step of displaying said test pattern at an initial position within said test window for a predetermined period; and said step of moving comprises the step of displaying said test pattern at a final position within said test window for a predetermined period.

53. A method as claimed in claim 52, wherein:

said step of displaying a background comprises the step of displaying said background as substantially vertical stripes which alternate sinusoidally between light and dark at said spatial frequency; and said step of displaying a test window comprises the step of displaying said test pattern as substantially vertical stripes which alternate sinusoidally between light and dark at said spatial frequency.

54. A method as claimed in claim 53, wherein said step of moving comprises the step of displaying said test pattern at said final position, said second position being either to the right or to the left of said first position;

said predetermined periods at which said test pattern is displayed at said initial and final positions being of a duration to induce in the subject an apparent sense of motion of said stripes moving right or left from said initial position to said final position.

55. A method as claimed in claim 52, wherein:

said step of displaying said test pattern at an initial position comprises the step of displaying said test pattern for less than about 0.2 second; and said step of displaying said test pattern at a final position comprises the step of displaying said test pattern for less than about 0.2 second.

56. A method for improving reading speed of a subject having a visual cortical movement system, said method comprising the steps of:

(a) displaying a background with a contrast and a spatial frequency;

(b) displaying a test window within said background, said test window including a test pattern with a contrast and a spatial frequency, said test pattern replacing said background;

said contrasts being within a range which stimulates the visual cortical movement system of the subject;

said spatial frequencies being within a range which stimulates the visual cortical movement system of the subject;

(c) moving said test pattern within said test window in either a first direction or a second direction;

(d) receiving a signal from the subject indicative of either said first direction or said second direction;

(e) modifying at least one of said contrasts or said spatial frequencies in response to said signal; and (f) repeating steps (a) through (e).

57. A method as claimed in claim 56, wherein said step of displaying a test window comprises the step of:

displaying said test pattern with a spatial frequency selected from a predetermined range of spatial frequencies;

said predetermined range of spatial frequencies of said test pattern including spatial frequencies ranging from about 0.25 cycle per degree to about 2 cycles per degree.

58. A method as claimed in claim 57, wherein said step of displaying a background comprises the step of:

displaying said background with a spatial frequency selected from a predetermined range of spatial frequencies;

said predetermined range of spatial frequencies of said background including spatial frequencies that are ¼, ½, 1, 2, and 4 times said spatial frequency at which said test pattern is displayed.

59. A method as claimed in claim 58, wherein said modifying step comprises the steps of:

increasing said contrast of said test pattern if said signal is incorrect; and decreasing said contrast of said test pattern if said signal is correct.

60. A method as claimed in claim 59, wherein said step of modifying further comprises the steps of:

varying said spatial frequency at which said background is displayed while maintaining constant said spatial frequency at which said test pattern is displayed.

61. A method as claimed in claim 60, wherein said step of modifying further comprises the steps of:

varying said spatial frequency at which said test pattern is displayed after said spatial frequency of said background is varied through each of said spatial frequencies of said predetermined range of spatial frequencies.

62. A method as claimed in claim 56, wherein:

said step of displaying a background comprises the step of displaying said background at a contrast selected from a predetermined range of contrasts; and said step of displaying a test window comprises the step of displaying said test pattern at a contrast selected from a predetermined range of contrasts;

said predetermined ranges of contrasts including contrasts of less than about 10%.

63. A method as claimed in claim 62, wherein said step of displaying a background comprises the step of:

displaying said background at a contrast of about 5%.

64. A method as claimed in claim 56, wherein:

said step of displaying a test window comprises the step of displaying said test pattern at an initial position within said test window for a predetermined period; and said step of moving comprises the step of displaying said test pattern at a final position within said test window for a predetermined period.

65. A method as claimed in claim 64, wherein:

said step of displaying said test pattern at an initial position comprises the step of displaying said test pattern for less than about 0.2 second; and said step of displaying said test pattern at a final position comprises the step of displaying said test pattern for less than about 0.2 second.

66. A method as claimed in claim 64, wherein:

said step of displaying a background comprises the step of displaying said background as substantially vertical stripes which alternate sinusoidally between light and dark at said spatial frequency; and said step of displaying a test window comprises the step of displaying said test pattern as substantially vertical stripes which alternate sinusoidally between light and dark at said spatial frequency.

67. A method as claimed in claim 66, wherein said step of moving comprises the step of displaying said test pattern at said final position, said second position being either to the right or to the left of said first position;

said predetermined periods at which said test pattern is displayed at said initial and final positions being of a duration to induce in the subject an apparent sense of motion of said stripes moving right or left from said initial position to said final position.

68. Apparatus for diagnosing dyslexia by measuring contrast sensitivity for movement discrimination of a subject having a visual cortical movement system, said apparatus comprising:

a monitor; and a computer connected to said monitor, said computer being configured to:

(a) display a background with a contrast and a spatial frequency;

(b) display a test window within said background, said test window including a test pattern with a contrast and a spatial frequency, said test pattern replacing said background;

said contrasts being within a range which stimulates the visual cortical movement system of the subject;

said spatial frequencies being within a range which stimulates the visual cortical movement system of the subject;

(c) move said test pattern within said test window in either a first direction or a direction;

(d) receive a signal from the subject indicative of either said first direction or said second direction;

(e) modify at least one of said contrasts and/or said spatial frequencies in response to said signal;

(f) repeat steps (a) through (e) a plurality of times; and (g) use the signals from the subject as criteria for forming a diagnosis of dyslexia.

69. Apparatus as claimed in claim 68, wherein said computer is further configured to display said test pattern with a spatial frequency selected from a predetermined range of spatial frequencies;

said predetermined range of spatial frequencies of said test pattern including spatial frequencies ranging from about 0.25 cycle per degree to about 2 cycles per degree.

70. Apparatus as claimed in claim 69, wherein said computer is configured to display said background with a spatial frequency selected from a predetermined range of spatial frequencies;

said predetermined range of spatial frequencies of said background including spatial frequencies that are ¼, ½, 1, 2, and 4 times said spatial frequency at which said test pattern is displayed.

71. Apparatus as claimed in claim 68, wherein said computer is configured to:

display said background at a contrast selected from a predetermined range of contrasts; and display said test pattern at a contrast selected from a predetermined range of contrasts;

said predetermined ranges of contrasts including contrasts of less than about 10%.

72. Apparatus as claimed in claim 71, wherein said computer is configured to display said background at a contrast of about 5%.

73. Apparatus as claimed in claim 68, wherein said computer is configured to:

display said test pattern at an initial position within said test window for a predetermined period; and display said test pattern at a final position within said test window for a predetermined period.

74. Apparatus as claimed in claim 73, wherein said computer is configured to display said test pattern at both said positions for less than about 0.2 second.

75. Apparatus as claimed in claim 68, wherein said computer is configured to vary said contrast at which said test pattern is displayed.

76. Apparatus as claimed in claim 75, wherein said computer is configured to vary said spatial frequency at which said background is displayed.

77. Apparatus as claimed in claim 76, wherein said computer is configured to vary said spatial frequency at which said test pattern is displayed.

78. Apparatus as claimed in claim 68, wherein said computer is further configured to display a blank field on said monitor before displaying said background and after moving said test pattern.

79. Apparatus as claimed in claim 68, wherein said test window is substantially circular.

80. Apparatus as claimed in claim 68, wherein said background is substantially larger than said test window.

81. Apparatus as claimed in claim 68, wherein said computer is configured to display said field such that said test is about 20% as large as said background.

82. Apparatus as claimed in claim 68 wherein dyslexia is diagnosed by measuring an absolute value of the contrast sensitivity for motion discrimination.

83. Apparatus as claimed in claim 68, wherein dyslexia is diagnosed by measuring contrast sensitivity for motion discrimination to yield a contrast sensitivity function with a shape.

84. The apparatus of claim 68 wherein the contrast of the test pattern is increased if the signal is incorrect, and wherein the contrast of the test pattern is decreased if the signal is correct.

85. The apparatus of claim 84, wherein the contrast of said test pattern is decreased only when a sequential number of signals are correct.

86. The apparatus of claim 85, wherein the number is three.

* * * * *